US008660801B2

(12) United States Patent
Torres-Roca et al.

(10) Patent No.: US 8,660,801 B2
(45) Date of Patent: Feb. 25, 2014

(54) GENE SIGNATURE FOR THE PREDICTION OF RADIATION THERAPY RESPONSE

(75) Inventors: Javier F. Torres-Roca, St Petersburg, FL (US); Steven Eschrich, Lakeland, FL (US)

(73) Assignee: University of South Florida, Tampa, FL (US)

( * ) Notice: Subject to any disclaimer, the term of this patent is extended or adjusted under 35 U.S.C. 154(b) by 6 days.

(21) Appl. No.: 13/037,153

(22) Filed: Feb. 28, 2011

(65) Prior Publication Data

US 2012/0053911 A1 Mar. 1, 2012

Related U.S. Application Data

(63) Continuation of application No. 12/210,135, filed on Sep. 12, 2008, now abandoned, and application No. 13/037,153, which is a continuation-in-part of application No. 12/053,796, filed on Mar. 24, 2008, now abandoned.

(60) Provisional application No. 60/972,544, filed on Sep. 14, 2007, provisional application No. 60/896,550, filed on Mar. 23, 2007, provisional application No. 60/896,350, filed on Mar. 22, 2007.

(51) Int. Cl.
*G01N 33/50* (2006.01)
*G01N 33/48* (2006.01)

(52) U.S. Cl.
USPC .......................................................... 702/19

(58) Field of Classification Search
None
See application file for complete search history.

(56) References Cited

U.S. PATENT DOCUMENTS

| | | | |
|---|---|---|---|
| 6,100,243 A | 8/2000 | Frisch | |
| 6,342,217 B1 | 1/2002 | Link et al. | |
| 8,101,349 B2 | 1/2012 | Garcia et al. | |
| 2002/0128220 A1 | 9/2002 | Gleave et al. | |
| 2003/0175717 A1 | 9/2003 | Li et al. | |
| 2005/0123945 A1 | 6/2005 | Torres-Roca et al. | |
| 2005/0282766 A1 | 12/2005 | Wu et al. | |
| 2006/0210556 A1 | 9/2006 | Baldwin et al. | |
| 2009/0023149 A1 | 1/2009 | Knudsen | |
| 2009/0181384 A1 | 7/2009 | Nekarda et al. | |
| 2011/0039270 A1 | 2/2011 | Cowens et al. | |

FOREIGN PATENT DOCUMENTS

WO    WO 00/50643    8/2000

OTHER PUBLICATIONS

Eschrich et al., "Mathematical Modeling of Radiation Response," Oasis, The Online Abstract Submission System, Abstract #3804: American Association for Cancer Research (AACR) 98th Annual Meeting, Los Angeles, CA, Apr. 2007, 3 pages.
Eschrich et al., "Mathematical Modeling of the Radiation Response Network," Poster, American Association for Cancer Research (AACR) 98th Annual Meeting, Apr. 2007, 1 page.
Eschrich et al., "Mathematical Modeling of the Radiation Response Network,"Abstract #3804, American Association for Cancer Research (AACR) 98th Annual Meeting, Apr. 2007, 2 pages.
Eschrich et al., "Systems Biology Modeling of the Radiation Sensitivity Network: A Biomarker Discovery Platform," *International Journal of Radiation: Oncology Biology Physics, Pergamon Press*, USA, vol. 75, No. 2, pp. 497-505, Oct. 1, 2009.
Eschrich et al., "Towards Personalized Radiation Therapy: Translation of a Mathematical Model of Radiosensitivity Network to the Prediction of Clinical Radiation Response" International Journal of Radiation Oncology*Biology*Physics, vol. 69(3, Suppl):S595 (Abstract #2713, American Society for Radiation Oncology (ASTRO) 49th Annual Meeting, Oct. 2007.
Eschrich et al., "Towards Personalized Radiation Therapy: Translation of a Mathematical Model of the Radiation Sensitivity Network to the Prediction of Clinical Radiation Response," Poster, American Society for Radiation Oncology (ASTRO) 49th Annual Meeting, Oct. 2007, 1 page.
Extended European Search Report; Application No. 08831180.8-1408 / 2195005; mailed Mar. 11, 2013; Applicant: University of South Florida; 7 pages.
International Search Report and Written Opinion; Application No. PCT/US2008/076311; mailed May 19, 2009 (12 pages).
Pamment et al., "Regulation of the IRF-1 Tumour Modifier the Response to Genotoxic Stress Involves an ATM-Dependent Signalling Pathway," Oncogene, 21:7776-7785 (2002).
Sha et al. "Cell Cycle-Mediated Drug Resistance and Emerging Concept in Cancer Therapy," *Clin. Caner Res.*, pp. 2168-2181, Aug. 7, 2001.
Torres-Roca, "A Multi-Gene Expression Model to Predict Tumor Radiosensitivity," Talk, RTOG Semi Annual Meeting, GU TRP Committee, Philadelphia, PA, Jun. 2008, 15 pages.
Torres-Roca, "Mathematical Models, Molecular Signatures and the Prediction of Response to Radiation Therapy," Talk, National Functional Genomics Center (NFGC) 5th Annual External Advisory Board Meeting, Clearwater, FL, Oct. 2007, 32 pages.
Torres-Roca, "Predicting Clinical Response to Concurrent Radiochemotherapy Using a Systems Model of Radiosensitivity," Invited talk, City of Hope Medical Center, Duarte, CA), Jan. 2008, 32 pages.
Torres-Roca, "Prediction of Clinical Response to Concurrent Radiochemotherapy Using a Systems Model of Radiosensitivity," Talk, Radiation Therapy Oncology Group (RTOG) Semi Annual Meeting, Jan. 2008, 20 pages.
Torres-Roca; "Mathematical Models, Molecular Signatures and the Prediction of Response to Radiation Therapy," Talk, 1st Annual Total Cancer Care Summit, Paradise Island, Bahamas, Oct. 2007, 31 pages.
Voy et al., "Extracting Gene Networks for Low-Dose Radiation Using Graph Theorectical Algorithms," Computational Biology, vol. 2, Issue 7, pp. 0757-0768, Jul. 2006.
Zhang et al., "Biological Validation of a Linear Regression Mathematical Model of Gene Expression and Radiation Response," Poster, American Association for Cancer Research (AACR) 98th Annual Meeting, Los Angeles, CA, Apr. 2007, 1 page.

(Continued)

*Primary Examiner* — Jason Sims
(74) *Attorney, Agent, or Firm* — Fish & Richardson P.C.

(57) ABSTRACT

Described are mathematical models and method, e.g., computer-implemented methods, for predicting tumor sensitivity to radiation therapy, which can be used, e.g., for selecting a treatment for a subject who has a tumor.

8 Claims, 28 Drawing Sheets

(56) References Cited

OTHER PUBLICATIONS

Zhang et al., "Biological Validation of a Linear Regression Mathematical Model of Gene Express and Radiation Response" (Short title "Mathematical Model of Radiation Response"), Abstract #3804, American Association for Cancer Research (AACR) 98th Annual Meeting, Los Angeles, CA, Apr. 2007, 3 pages.

Albert et al., "Error and attack tolerance of complex networks," Nature, 406: 378-382 (2000).

Algan et al., "Management of adenocarcinoma of the esophagus with chemoradiation alone or chemoradiation followed by esophagectomy: results of sequential nonrandomized phase II studies," International journal of radiation oncology, biology, physics, 32:753-761 (1995).

Alizadeh et al., "Distinct types of diffuse large B-cell lymphoma identified by gene expression profiling," Nature, 403:503-511 (2000).

Al-Sarraf et al., "Chemoradiotherapy versus radiotherapy in patients with advanced nasopharyngeal cancer: phase III randomized Intergroup study 0099," J Clin Oncol, 16:1310-1317 (1998).

Al-Saaf et al., "Progress report of combined chemoradiotherapy versus radiotherapy alone in patients with esophageal cancer: an intergroup study," J Clin Oncol, 15:277-284 (1997).

Beer et al., "Gene-expression profiles predict survival of patients with lung adenocarcinoma," Nat Med, 8:816-824 (2002).

Begg et al., "The value of pretreatment cell kinetic parameters as predictors for radiotherapy outcome in head and neck cancer: a multicenter analysis," Radiother Oncol, 50:13-23 (1999).

Bild et al., "Oncogenic pathway signatures in human cancers as a guide to targeted therapies," Nature, 439:353-357 (2006).

Bjork-Eriksson et al., "Tumor radiosensitivity (SF2) is a prognostic factor for local control in head and neck cancers," (2000) Int J Radiat Oncol Biol Phys, 46(1):13-19 (2000).

Bolla et al., "Improved Survival in Patients with Locally Advanced Prostate Cancer Treated with Radiotherapy and Goserelin," N Engl J Med, 337:295-300 (1997).

Bolla et al., "Long-term results with immediate androgen suppression and external irradiation in patients with locally advanced prostate cancer (an EORTC study): a phase III randomised trial," The Lancet 360:103-108 (2002).

Bossett et al., "Chemotherapy with Preoperative Radiotherapy in Rectal Cancer," N Engl J Med, 355:1114-1123 (2006).

Bourhis et al., "Potential doubling time and clinical outcome in head and neck squamous cell carinoma treated with 70 GY in 7 weeks," Int J Radiat Oncol Biol Phys, 35:471-476 (1996).

Breiman et al., Classification and Regression Trees, Belmont: Wadsworth (1983).

Brizel et al., "Hyperfractionated Irradiation with or without Concurrent Chemotherapy for Locally Advanced Head and Neck Cancer," N Engl J Med, 338:1798-1804 (1998).

Browman et al., "Choosing a concomitant chemotherapy and radiotherapy regimen for squamous cell head and neck cancer: A systematic review of the published literature with subgroup analysis," Head & Neck, 23:579-589 (2001).

Bucci et al., "Advances in Radiation Therapy: Conventional to 3D, to IMRT, to 4D, and Beyond," CA Cancer J Clin, 55:117-134 (2005).

Buffa et al., "Incorporating biologic measurements (SF(2), CFE) into a tumor control probability model increases their prognostic significance: a study in cervical carcinoma treated with radiation therapy," Int J Radiat Oncol Biol Phys, 50(5):1113-1122 (2001).

Capirci et al., "Prognostic Value of Pathologic Complete Response After Neoadjuvant Therapy in Locally Advanced Rectal Cancer: Long-term Analysis of 566 ypCR Patients," International Journal of Radiation Oncology Biology Physics, 72(1):99-107 (2008).

Cerna et al., "Histone deacetylation as a target for radiosensitization," Curr Top Dev Biol, 73:173-204 (2006).

Chang et al., "GATHER: a systems approach to interpreting genomic signatures," Bioinformatics, 22:2926-2933 (2006).

Chen et al., "Downstaging of advanced rectal cancer following combined preoperative chemotherapy and high dose radiation," International Journal of Radiation Oncology, Biology, Physics, 30:169-175 (1994).

Chinnaiyan et al., "Modulation of radiation response by histone deacetylase inhibition," Int J Radiat Oncol Biol Phys, 62:223-229 (2005).

Chirieac et al., "Post therapy pathologic stage predicts survival in patients with esophageal carcinoma receiving preoperative chemoradiation," Cancer, 103:1347-1355 (2005).

Cho et al., "Topoisomerase I inhibitors in the combined-modality therapy of lung cancer," Oncology, 18:29-39 (2004).

Chung et al., "Molecular classification of head and neck squamous cell carcinomas using patterns of gene expression," Cancer Cell, 5:489-500 (2004).

Corvo et al., "In vivo cell kinetics in head and neck squamous cell carcinomas predicts local control and helps guide radiotherapy regimen," J Clin Oncol, 13:1843-1850 (1995).

Cox et al., "The dark side of Ras: regulation of apoptosis," Oncogene, 22:8999-9006 (2003).

Cuddihy et al., "The p53 protein family and radiation sensitivity: Yes or No?" Cancer Metastasis Rev, 23:237-257 (2004).

D'Amico et al., "6-Month Androgen Suppression Plus Radiation Therapy vs Radiation Therapy Alone for Patients With Clinically Localized Prostate Cancer: A Randomized Controlled Trial," JAMA, 292:821-827 (2004).

Dalton et al., "Cancer biomarkers—an invitation to the table," Science 312:1165-1168 (2006).

Deng et al., "Caenorhabditis Elegans ABL-1 Antogonizes P53-Mediated Germline Apoptosis After Ionizing Irradiation," Nature Genetics, 36:906-912 (2004).

Denis et al., "Final Results of the 94-01 French Head and Neck Oncology and Radiotherapy Group Randomized Trial Comparing Radiotherapy Alone With Concomitant Radiochemotherapy in Advanced-Stage Oropharynx Carcinoma," J Clin Oncol, 22:69-76 (2004).

Deschavanne et al., "A review of human cell radiosensitivity in vitro," Int J Radiat Oncol Biol Phys, 34(1):251-266 (1996).

Dobbin et al., "Interlaboratory comparability study of cancer gene expression analysis using oligonucleotide microarrays," Clin Cancer Res, 11:565-572 (2005).

Eifel et al., "Pelvic Irradiation With Concurrent Chemotherapy Versus Pelvic and Para-Aortic Irradiation for High-Risk Cervical Cancer: An Update of Radiation Therapy Oncology Group Trial (RTOG) 90-01," J Clin Oncol, 22:872-880 (2004).

El-Deiry, W. S., "The role of p53 in chemosensitivity and radiosensitivity," Oncogene, 22, 7486-7495 (2003).

Eschrich et al., "Molecular staging for survival prediction of colorectal cancer patients," J Clin Oncol, 23:3526-3535 (2005).

Eschwege et al., "Predictive assays of radiation response in patients with head and neck squamous cell carcinoma: a review of the Institute Gustave Roussy experience," Int J Radiat Oncol Biol Phys, 39:849-853 (1997).

Fertil et al., "Inherent cellular radiosensitivity as a basic concept for human tumor radiotherapy," Int J Radiat Oncol Biol Phys, 7(5):621-629 (1981).

Fertil et al., "Intrinsic radiosensitivity of human cell lines is correlated with radioresponsiveness of human tumors: analysis of 101 published survival curves," International Journal of Radiation Oncology, Biology, Physics, 11:1699-1707 (1985).

Fiorica et al., "Preoperative chemoradiotherapy for oesophageal cancer: a systematic review and meta-analysis," Gut, 53(7):925-930 (2004).

Fryknäs et al., "STAT1 signaling is associated with acquired crossresistance to doxorubicin and radiation in myeloma cell lines," International Journal of Cancer, 120:189-195 (2007).

Furuse et al., "Phase III Study of Concurrent Versus Sequential Thoracic Radiotherapy in Combination With Mitomycin, Vindesine, and Cisplatin in Unresectable Stage III Non-Small-Cell Lung Cancer," J Clin Oncol, 17:2692-2699 (1999).

Fyles et al., "Tumor hypoxia has independent predictor impact only in patients with node-negative cervix cancer," J Clin Oncol, 20:680-687 (2002).

Gavioli et al., "Incidence and Clinical Impact of Sterilized Disease and Minimal Residual Disease After Preoperative Radiochemotherapy for Rectal Cancer," Dis Colon Rectum, 48:1851-1857 (2005).

(56) References Cited

OTHER PUBLICATIONS

Giles et al., "Optimizing outcomes for patients with advanced disease in chronic myelogenous leukemia," Semin Oncol, 35:S1-17; quiz S18-20 (2008).

Gudkov et al., "The Role of p53 in Determining Sensitivity to Radiotherapy," Nature Reviews Cancer, 3:117-129 (2003).

Hallahan et al., "Prolonged c-jun expression in irradiated ataxia telangiectasia fibroblasts," International Journal of Radiation Oncology, Biology, Physics, 36:355-360 (1996).

Hallahan et al., "Radiation signaling mediated by Jun activation following dissociation from a cell type-specific repressor," J Biol Chem, 268:4903-4907 (1993).

Hanks et al., "Phase III Trial of Long-Term Adjuvant Androgen Deprivation After Neoadjuvant Hormonal Cytoreduction and Radiotherapy in Locally Advanced Carcinoma of the Prostate: The Radiation Therapy Oncology Group Protocol 92-02," J Clin Oncol, 21:3972-3978 (2003).

Hennequin et al., "Chemotherapy with cisplatinum, carboplatin and 5FU-folinic acid, followed by concomitant chemo-radiotherapy in unresectable esophageal carcinomas," Bull Cancer, 88(2):203-207 (2001).

Hennequin et al., "Impact on survival of surgery after concomitant chemoradiotherapy for locally advanced cancers of the esophagus," International Journal of Radiation Oncology, Biology, Physics, 49:657-664 (2001).

Herskovic et al., "Combined chemotherapy and radiotherapy compared with radiotherapy alone in patients with cancer of the esophagus," N Engl J Med, 326:1593-1598 (1992).

Hieronymus et al., "Gene expression signature-based chemical genomic prediction identifies a novel class of HSP90 pathway modulators," Cancer Cell, 10:321-330 (2006).

Hood et a., "Systems Biology and New Technologies Enable Predictive and Preventative Medicine," Science, 306:640-643 (2004).

Hood et al., "The impact of systems approaches on biological problems in drug discovery," Nat. Biotechnol., 10:1215-1217 (2004).

Irizarry et al., "Summaries of Affymetrix GeneChip probe level data," Nucleic Acids Res, 31:e15 (2003).

Janjan et al., "Improved Overall Survival Among Responders to Preoperative Chemoradiation for Locally Advanced Rectal Cancer," Am J Clin Oncol, 24:107-112 (2001).

Janjan et al., "Tumor downstaging and sphincter preservation with preoperative chemoradiation in locally advanced rectal cancer: the M. D. Anderson Cancer Center experience," International Journal of Radiation Oncology,Biology,Physics, 44:1027-1038 (1999).

Jassem, J., "Combined chemotherapy and radiation in locally advanced nonsmall-cell lung cancer," The Lancet Oncology, 2:335-342 (2001).

Jeong et al., "Lethality and centrality in protein networks," Nature, 411:41-42 (2001).

Jeong et al., "The large-scale organization of metabolic networks," Nature, 407(6804):651-654 (2000).

Jeremic et al., "Hyperfractionated radiation therapy with or without concurrent low-dose daily carboplatin/etoposide for stage III non-small-cell lung cancer: a randomized study," J Clin Oncol, 14:1065-1070 (1996).

Jeremic et al., "Hyperfractionated Radiation Therapy With or Without Concurrent Low-Dose Daily Cisplatin in Locally Advanced Squamous Cell Carcinoma of the Head and Neck: A Prospective Randomized Trial," J Clin Oncol, 18:1458-1464 (2000).

Jeremic et al., "Randomized trial of hyperfractionated radiation therapy with or without concurrent chemotherapy for stage III non-small-cell lung cancer," J Clin Oncol, 13:452-458 (1995).

Kaminski et al., "Effect of sequencing of androgen deprivation and radiotherapy on prostate cancer growth," International Journal of Radiation Oncology, Biology, Physics, 57:24-28 (2003).

Kao et al., "p34Cdc2kinase activity is excluded from the nucleus during the radiation-induced G2 arrest in HeLa cells," J Biol Chem, 274:34779-34784 (1999).

Keys et al., "Cisplatin, Radiation, and Adjuvant Hysterectomy Compared with Radiation and Adjuvant Hysterectomy for Bulky Stage IB Cervical Carcinoma," N Engl J Med, 340:1154-1161 (1999).

Khan et al., "Classification and diagnostic prediction of cancers using gene expression profiling and artificial neural networks," Nature Medicine, 7(6):673-679 (2001).

Kim et al., "The influence of Ras pathway signaling on tumor radiosensitivity," Cancer and Metastasis Reviews, 23:227-236 (2004).

Kitano, "Computational systems biology," Nature, 420(6912):206-210 (2002).

Kitano, H., "Systems Biology: A Brief Overview," Science, 295:1662-1664 (2002).

Lamb et al., "The Connectivity Map: Using Gene-Expression Signatures to Connect Small Molecules, Genes, and Disease," Science, 313:1929-1935 (2006).

Landry et al., "Preoperative irradiation and fluorouracil chemotherapy for locally advanced rectosigmoid carcinoma: phase I-II study," Radiology, 188:423-426 (1993).

Lawton et al., "Androgen suppression plus radiation versus radiation alone for patients with stage D1/pathologic node-positive adenocarcinoma of the prostate: updated results based on national prospective randomized trial Radiation Therapy Oncology Group 85-31," J Clin Oncol, 23:800-807 (2005).

Li et al., "AKT-independent protection of prostate cancer cells from apoptosis mediated through complex formation between the androgen receptor and FKHR," Mol Cell Biol, 23:104-118 (2003).

Li et al., "Ionizing radiation and short wavelength UV activate NF-kappa B through two distinct mechanisms," PNAS, 95:13012-13017 (1998).

Lindsay et al., "The genetic basis of tissue responses to ionizing radiation," Br J Radiol, 80:S2-6 (2007).

Liu et al., "NF-[kappa]B Is Required for UV-Induced JNK Activation via Induction of PKCδ," Molecular Cell, 21:467-480 (2006).

Lorvidhaya et al., "Concurrent mitomycin C, 5-fluorouracil, and radiotherapy in the treatment of locally advanced carcinoma of the cervix: a randomized trial," International Journal of Radiation Oncology,Biology,Physics, 55:1226-1232 (2003).

Ma et al., "Combined-Modality Treatment of Solid Tumors Using Radiotherapy and Molecular Targeted Agents," J Clin Oncol, 21:2760-2776 (2003).

Malaise et al., "Distribution of radiation sensitivities for human tumor cells of specific histological types: comparison of in vitro to in vivo data," International Journal of Radiation Oncology, Biology, Physics, 12:617-624 (1986).

Mao et al., "SUMO-1 conjugation to topoisomerase I: A possible repair response to topoisomerase-mediated DNA damage," Proc Natl Acad Sci U S, A97:4046-4051 (2000).

Marples et al., "Low-dose hyper-radiosensitivity: past, present, and future," Int J Radiat Oncol Biol Phys, 70:1310-13188 (2008).

Massague, J., "Sorting out breast-cancer gene signatures," N. Engl. J. Med., 356: 294-297 (2007).

Mialon et al., "DNA topoisomerase I is a cofactor for c-Jun in the regulation of epidermal growth factor receptor expression and cancer cell proliferation," Mol. Cell Biol., 25:5040-5051 (2005).

Milas et al., "Chemoradiotherapy: Emerging treatment improvement strategies" Head & Neck, 25:152-167 (2003).

Minsky et al., "Enhancement of radiation-induced downstaging of rectal cancer by fluorouracil and high-dose leucovorin chemotherapy," J. Clin. Oncol., 10:79-84 (1992).

Moeller et al., "Hypoxia and radiotherapy: opportunities for improved outcomes in cancer treatment," Cancer Metastasis Rev., 26:241-248 (2007).

Mohiuddin et al., "Preoperative chemoradiation in fixed distal rectal cancer: dose time factors for pathological complete response," International Journal of Radiation Oncology, Biology, Physics, 46:883-888 (2000).

Mohiuddin et al., "Prognostic significance of postchemoradiation stage following preoperative chemotherapy and radiation for advanced/recurrent rectal cancers," Int. J. Radiat. Oncol. Biol. Phys., 48(4):1075-1080 (2000).

(56) References Cited

OTHER PUBLICATIONS

Morris et al., "Pelvic Radiation with Concurrent Chemotherapy Compared with Pelvic and Para-Aortic Radiation for High-Risk Cervical Cancer," N. Engl. J. Med., 340:1137-1143 (1999).
Movsas et al., "Hypoxic prostate/muscle pO2 ratio predicts for biochemical failure in patients with prostate cancer: preliminary findings," Urology, 60:634-639 (2002).
Nahta et al., "Mechanisms of disease: understanding resistance to HER2-targeted therapy in human breast cancer," Nat. Clin. Pract. Oncol., 3:269-280 (2006).
Nakajima et al., "Involvement of protein kinase C-related anti-apoptosis signaling in radiation-induced apoptosis in murine thymic lymphoma(3SBH5) cells," Radiat. Res., 161:528-534 (2004).
Nakajima et al., "Regulation of radiation-induced protein kinase Cdelta activation in radiation-induced apoptosis differs between radiosensitive and radioresistant mouse thymic lymphoma cell lines," Mutat. Res., 595(1-2):29-36 (2006).
Narlikar et al., "Cooperation between Complexes that Regulate Chromatin Structure and Transcription," Cell, 108:475-487 (2002).
Office Action issued in U.S. Appl. No. 10/904,326 on Dec. 11, 2008.
Office Action issued in U.S. Appl. No. 10/904,326 on Dec. 12, 2007.
Office Action issued in U.S. Appl. No. 10/904,326 on May 22, 2007.
Office Action issued in U.S. Appl. No. 10/904,326 on May 29, 2008.
Pamment et al., "Regulation of the IRF-1 tumour modifier during the response to genotoxic stress involves an ATM-dependent signalling pathway," Oncogene, 21:7776-7785 (2002).
Peeters et al., "Acute and late complications after radiotherapy for prostate cancer: results of a multicenter randomized trial comparing 68 Gy to 78 Gy," Int. J. Radiat. Oncol. Biol. Phys., 61:1019-1034 (2005).
Perez, C., "Principles and Management of Radiation Therapy," Philadelphia-New York, Lippincott-Raven (1998).
Peters et al., "Concurrent Chemotherapy and Pelvic Radiation Therapy Compared With Pelvic Radiation Therapy Alone as Adjuvant Therapy After Radical Surgery in High-Risk Early-Stage Cancer of the Cervix," J. Clin. Oncol., 18:1606-1613 (2000).
Peters et al., "Predictive assays of tumor radiocurability," Am. J. Clin. Oncol., 11(3):275-287 (1988).
Peters, LJ, "The ESTRO Regaud lecture. Inherent radiosensitivity of tumor and normal tissue cells as a predictor of human tumor response," Radiother. Oncol., 17(3):177-190 (1990).
Pilepich et al., "Phase III radiation therapy oncology group (RTOG) trial 86-10 of androgen deprivation adjuvant to definitive radiotherapy in locally advanced carcinoma of the prostate," International Journal of Radiation Oncology, Biology, Physics, 50:1243-1252 (2001).
Potti et al., "Genomic signatures to guide the use of chemotherapeutics," Nat. Med., 12:1294-1300 (2006).
Pramana et al., "Gene expression profiling to predict outcome after chemoradiation in head and neck cancer," Int. J. Radiat. Oncol. Biol. Phys., 69:1544-1552 (2007).
Qiu et al., "Molecular prognostic factors in rectal cancer treated by radiation and surgery," Dis. Colon Rectum, 43(4):451-459 (2000).
Reboul, F., "Radiotherapy and chemotherapy in locally advanced non-small cell lung cancer: preclinical and early clinical data," Hematol. Oncol. Clin. North. Am., 18:41-53 (2004).
Rich et al., "Preoperative infusional chemoradiation therapy for stage T3 rectal cancer," International Journal of Radiation Oncology, Biology, Physics, 32:1025-1029 (1995).
Rose al., "Concurrent Cisplatin-Based Radiotherapy and Chemotherapy for Locally Advanced Cervical Cancer," N. Engl. J. Med., 340:1144-1153 (1999).
Rosen et al., "Biological Basis of Radiation Sensitivity. Part 2: Cellular and Molecular Determinants of Radiosensitivity," Oncology, 14:741-757 (2000).
Russell et al., "Gleevec-Mediated Inhibition of Rad51 Expression and Enhancement of Tumor Cell Radiosensitivity," Cancer Res., 63:7377-7383 (2003).
Sauer et al., "Preoperative versus postoperative chemoradiotherapy for rectal cancer," N. Engl. J. Med., 351(17):1731-1740 (2004).
Schaake-Koning et al., "Effects of concomitant cisplatin and radiotherapy on inoperable non-small-cell lung cancer," N. Engl. J. Med., 326:524-530 (1992).
Shedden et al., "Gene expression-based survival prediction in lung adenocarcinoma: a multi-site, blinded validation study," Nat. Med., 14:822-827 (2008).
Simon et al., "Pitfalls in the Use of DNA Microarray Data for Diagnostic and Prognostic Classification," J. Natl. Cancer. Inst., 95:14-18 (2003).
Staunton et al., "Chemosensitivity prediction by transcriptional profiling," Proc. Natl. Acad. Sci. USA, 98:10787-10792 (2001).
Stausbol-Gron et al., "Relationship between tumour cell in vitro radiosensitivity and clinical outcome after curative radiotherapy for squamous cell carcinoma of the head and neck," Radiother. Oncol., 50(1):47-55 (1999).
Taghian et al., "Intrinsic radiation sensitivity may not be the major determinant of the poor clinical outcome of glioblastoma multiforme," Int. J. Radiat. Oncol. Biol. Phys., 25(2):243-249 (1993).
Tannapfel et al., "Apoptosis, proliferation, bax, bcl-2 and p53 status prior to and after preoperative radiochemotherapy for locally advanced rectal cancer," Int. J. Radiat. Oncol. Biol. Phys., 41(3):585-91(1998).
Tepper et al., "Superiority of trimodality therapy to surgery alone in esophageal cancer: Results of CALGB 9781," In: ASCO. San Francisco, (2006).
Terzoudi et al., "Increased G2 chromosomal radiosensitivity in cancer patients: the role of cdk1/cyclin-B activity level in the mechanisms involved," Int. J. Radiat. Biol., 76:607-615 (2000).
Torres-Roca et al., "Prediction of radiation sensitivity using a gene expression classifier," Cancer Res., 65:7169-7176 (2005).
Tusher et al., "Significance analysis of microarrays applied to the ionizing radiation response," Proc. Natl. Acad. Science USA, 98(9):5116-5121 (2001).
Van de Vijver et al., "A gene-expression signature as a predictor of survival in breast cancer," N. Engl. J. Med., 347:1999-2009 (2002).
Van Gelder et al., "Amplified RNA synthesized from limited quantities of heterogeneous cDNA," Proc. Natl. Acad. Sci. USA, 87:1663-1667 (1990).
Van 'T Veer et al., "Gene expression profiling predicts clinical outcome of breast cancer," Nature, 415:530-536 (2002).
Wang et al., "DNA repair factor XPC is modified by SUMO-1 and ubiquitin following UV irradiation," Nucleic Acids Res., 33:4023-4034 (2005).
Wang et al., "Loss of Tumor Suppressor p53 Decreases PTEN Expression and Enhances Signaling Pathways Leading to Activation of Activator Protein 1 and Nuclear Factor {kappa}B Induced by UV Radiation," Cancer Res., 65:6601-6611 (2005).
Watanbe et al., "Prediction of sensitivity of rectal cancer cells in response to preoperative radiotherapy by DNA microarray analysis of gene expression profiles," Cancer Res., 66:3370-3374 (2006).
Wei et al., "Gene expression-based chemical genomics identifies rapamycin as a modulator of MCL1 and glucocorticoid resistance," Cancer Cell, 10:331-342 (2006).
Weichselbaum et al., "An interferon-related gene signature for DNA damage resistance is a predictive marker for chemotherapy and radiation for breast cancer," Proc. Natl. Acad. Sci. USA, 105(47):18490-18495 (2008).
Wendt et al., "Simultaneous radiochemotherapy versus radiotherapy alone in advanced head and neck cancer: a randomized multicenter study," J. Clin. Oncol., 16:1318-1324 (1998).
West et al., "Intrinsic radiosensitivity and prediction of patient response to radiotherapy for carcinoma of the cervix," Br. J. Cancer, 68:819-823 (1993).
West et al., "The independence of intrinsic radiosensitivity as a prognostic factor for patient response to radiotherapy of carcinoma of the cervix," British Journal of Cancer, 76:1184-1190 (1997).
Whitney et al., "Randomized Comparison of Fluorouracil Plus Cisplatin Versus Hydroxyurea as an Adjunct to Radiation Therapy in Stage IIB-IVA Carcinoma of the Cervix With Negative Para-Aortic Lymph Nodes: A Gynecologic Oncology Group and Southwest Oncology Group Study," J. Clin. Oncol., 17:1339-1348 (1999).
Wong et al., "Gene expression pattern associated with radiotherapy sensitivity in cervical cancer," Cancer J., 12:189-193 (2006).

(56) References Cited

OTHER PUBLICATIONS

Xu et al., "Merging microarray data from separate breast cancer studies provides a robust prognostic test," BMC Bioinformatics, 9:125 (2008).

Zelefsky et al., "High Dose Radiation Delivered by Intensity Modulated Conformal Radiotherapy Improves the Outcome of Localized Prostate Cancer," The Journal of Urology, 166:876-881 (2001).

Zhang et al., "FoxO1 regulates multiple metabolic pathways in the liver: effects on gluconeogenic, glycolytic, and lipogenic gene expression," J. Biol. Chem., 281(15):10105-10117 (2006).

FIG. 4A

| # in Subset | Combination | wilcox_topotecan | ttest_topotecan | wilcox_esophagus | ttest_esophagus | wilcox_all | ttest_all |
|---|---|---|---|---|---|---|---|
| 2 | cAbl_IRF1 | 0.005373 | 0.012516 | 0.029853 | 0.01501 | 0.00121 | 0.000477 |
| 3 | RelA_cAbl_IRF1 | 0.005373 | 0.012516 | 0.029853 | 0.01501 | 0.000492 | 0.0002229 |
| 3 | AR_cAbl_IRF1 | 0.005373 | 0.012516 | 0.029853 | 0.01501 | 0.00121 | 0.000477 |
| 3 | cAbl_CDK1_IRF1 | 0.005373 | 0.012516 | 0.029853 | 0.01501 | 0.00121 | 0.000477 |
| 3 | cAbl_HDAC_IRF1 | 0.005373 | 0.012516 | 0.029853 | 0.01501 | 0.00121 | 0.000477 |
| 3 | PKC_cAbl_IRF1 | 0.005373 | 0.012516 | 0.029853 | 0.01501 | 0.00121 | 0.000477 |
| 3 | cAbl_SUMO1_IRF1 | 0.035987 | 0.035436 | 0.031855 | 0.018255 | 0.003416 | 0.002409 |
| 3 | STAT1_cAbl_IRF1 | 0.012241 | 0.008824 | 0.05616 | 0.025671 | 0.004827 | 0.001529 |
| 3 | cjun_SUMO1_IRF1 | 0.062937 | 0.049913 | 0.217484 | 0.181384 | 0.047429 | 0.041273 |
| 3 | cjun_cAbl_IRF1 | 0.025036 | 0.013106 | 0.401552 | 0.214128 | 0.053627 | 0.04507 |
| 4 | AR_cAbl_CDK1_IRF1 | 0.005373 | 0.012516 | 0.029853 | 0.01501 | 0.000492 | 0.000248 |
| 4 | AR_RelA_cAbl_IRF1 | 0.005373 | 0.012516 | 0.029853 | 0.01501 | 0.000492 | 0.000523 |
| 4 | PKC_RelA_cAbl_IRF1 | 0.005373 | 0.012516 | 0.029853 | 0.01501 | 0.000492 | 0.000696 |
| 4 | RelA_cAbl_CDK1_IRF1 | 0.005373 | 0.012516 | 0.029853 | 0.01501 | 0.000492 | 0.000143 |
| 4 | RelA_cAbl_HDAC_IRF1 | 0.005373 | 0.012516 | 0.029853 | 0.01501 | 0.000492 | 0.000265 |
| 4 | STAT1_RelA_cAbl_IRF1 | 0.012328 | 0.010119 | 0.024243 | 0.016151 | 0.000699 | 0.000177 |
| 4 | PKC_cAbl_CDK1_IRF1 | 0.006254 | 0.012343 | 0.033537 | 0.014748 | 0.001178 | 0.00045 |
| 4 | AR_cAbl_HDAC_IRF1 | 0.005373 | 0.012516 | 0.029853 | 0.01501 | 0.00121 | 0.000477 |
| 4 | cAbl_CDK1_HDAC_IRF1 | 0.005373 | 0.012516 | 0.029853 | 0.01501 | 0.00121 | 0.000477 |
| 4 | PKC_cAbl_HDAC_IRF1 | 0.005373 | 0.012516 | 0.029853 | 0.01501 | 0.00121 | 0.000477 |
| 4 | cjun_RelA_cAbl_IRF1 | 0.005544 | 0.009993 | 0.161613 | 0.121041 | 0.001984 | 0.003274 |
| 4 | RelA_cAbl_SUMO1_IRF1 | 0.071803 | 0.045561 | 0.031855 | 0.02023 | 0.002509 | 0.002264 |
| 4 | AR_cAbl_SUMO1_IRF1 | 0.035987 | 0.050036 | 0.031855 | 0.020877 | 0.003416 | 0.004503 |
| 4 | cAbl_SUMO1_CDK1_IRF1 | 0.035987 | 0.035796 | 0.031855 | 0.01833 | 0.003416 | 0.002455 |
| 4 | cAbl_SUMO1_HDAC_IRF1 | 0.035987 | 0.03281 | 0.031855 | 0.01769 | 0.003416 | 0.002078 |
| 4 | STAT1_cAbl_CDK1_IRF1 | 0.012241 | 0.009894 | 0.05616 | 0.024981 | 0.004827 | 0.001584 |
| 4 | STAT1_cAbl_HDAC_IRF1 | 0.012241 | 0.008931 | 0.05616 | 0.02479 | 0.004827 | 0.001605 |
| 4 | PKC_cAbl_SUMO1_IRF1 | 0.035987 | 0.071565 | 0.031855 | 0.023852 | 0.005608 | 0.008201 |
| 4 | STAT1_cAbl_SUMO1_IRF1 | 0.027078 | 0.03267 | 0.05616 | 0.032111 | 0.006116 | 0.005202 |
| 4 | AR_STAT1_cAbl_IRF1 | 0.012241 | 0.010393 | 0.105 | 0.030559 | 0.006545 | 0.001432 |
| 4 | STAT1_PKC_cAbl_IRF1 | 0.012241 | 0.010287 | 0.105 | 0.029999 | 0.006545 | 0.001473 |
| 4 | AR_cjun_cAbl_IRF1 | 0.005544 | 0.010739 | 0.180301 | 0.147927 | 0.011731 | 0.020577 |
| 4 | cjun_cAbl_CDK1_IRF1 | 0.005544 | 0.003794 | 0.180301 | 0.093807 | 0.011731 | 0.008461 |
| 4 | cjun_STAT1_cAbl_IRF1 | 0.010946 | 0.006805 | 0.164081 | 0.085722 | 0.013228 | 0.009471 |
| 4 | AR_PKC_cAbl_IRF1 | 0.005373 | 0.012516 | 0.029853 | 0.01501 | 0.013696 | 0.000586 |
| 4 | cjun_cAbl_SUMO1_IRF1 | 0.033842 | 0.069441 | 0.161933 | 0.121554 | 0.023319 | 0.044378 |

FIG. 4B

| | | | | | | | |
|---|---|---|---|---|---|---|---|
| 4 | AR_cjun_SUMO1_IRF1 | 0.062987 | 0.049538 | 0.217484 | 0.182111 | 0.047429 | 0.041082 |
| 4 | cjun_SUMO1_CDK1_IRF1 | 0.062987 | 0.049186 | 0.217484 | 0.182858 | 0.047429 | 0.040902 |
| 4 | cjun_cAbl_HDAC_IRF1 | 0.025036 | 0.012992 | 0.402595 | 0.28402 | 0.050314 | 0.061527 |
| 4 | cjun_PKC_cAbl_IRF1 | 0.025036 | 0.013162 | 0.401552 | 0.215606 | 0.053627 | 0.045762 |
| 5 | STAT1_PKC_RelA_cAbl_IRF1 | 0.012328 | 0.01048 | 0.024243 | 0.016802 | 0.000401 | 0.000195 |
| 5 | AR_PKC_cAbl_CDK1_IRF1 | 0.066254 | 0.012197 | 0.033537 | 0.014537 | 0.000423 | 0.00027 |
| 5 | PKC_RelA_cAbl_CDK1_IRF1 | 0.006254 | 0.012438 | 0.033537 | 0.01489 | 0.000423 | 0.000226 |
| 5 | AR_cAbl_CDK1_HDAC_IRF1 | 0.005373 | 0.012516 | 0.029853 | 0.01501 | 0.000492 | 0.000188 |
| 5 | AR_PKC_RelA_cAbl_IRF1 | 0.005373 | 0.012516 | 0.029853 | 0.01501 | 0.000492 | 0.001008 |
| 5 | AR_RelA_cAbl_CDK1_IRF1 | 0.005373 | 0.012516 | 0.029853 | 0.01501 | 0.000492 | 0.000365 |
| 5 | AR_RelA_cAbl_HDAC_IRF1 | 0.005373 | 0.012516 | 0.029853 | 0.01501 | 0.000492 | 0.000438 |
| 5 | PKC_RelA_cAbl_HDAC_IRF1 | 0.005373 | 0.012516 | 0.029853 | 0.01501 | 0.000492 | 0.000764 |
| 5 | RelA_cAbl_CDK1_HDAC_IRF1 | 0.005373 | 0.012516 | 0.029853 | 0.01501 | 0.000492 | 0.000146 |
| 5 | AR_STAT1_RelA_cAbl_IRF1 | 0.012328 | 0.010513 | 0.059461 | 0.019991 | 0.000699 | 0.00021 |
| 5 | STAT1_RelA_cAbl_CDK1_IRF1 | 0.012328 | 0.010081 | 0.024243 | 0.016527 | 0.000699 | 0.000295 |
| 5 | STAT1_RelA_cAbl_HDAC_IRF1 | 0.012328 | 0.010226 | 0.035251 | 0.015236 | 0.000837 | 0.000293 |
| 5 | AR_cjun_RelA_cAbl_IRF1 | 0.005544 | 0.009512 | 0.181613 | 0.101933 | 0.000984 | 0.002298 |
| 5 | cjun_PKC_RelA_cAbl_IRF1 | 0.005544 | 0.011253 | 0.181613 | 0.158955 | 0.000994 | 0.006957 |
| 5 | PKC_cAbl_CDK1_HDAC_IRF1 | 0.006254 | 0.012164 | 0.033537 | 0.01449 | 0.001178 | 0.000424 |
| 5 | STAT1_RelA_cAbl_SUMO1_IRF1 | 0.034423 | 0.036802 | 0.024243 | 0.023999 | 0.001391 | 0.001695 |
| 5 | PKC_RelA_cAbl_SUMO1_IRF1 | 0.031347 | 0.067599 | 0.031855 | 0.022982 | 0.001515 | 0.005488 |
| 5 | AR_cAbl_SUMO1_CDK1_IRF1 | 0.035987 | 0.045044 | 0.031855 | 0.02006 | 0.00176 | 0.002975 |
| 5 | cjun_RelA_cAbl_CDK1_IRF1 | 0.005544 | 0.003292 | 0.181613 | 0.074044 | 0.001984 | 0.001061 |
| 5 | cjun_STAT1_RelA_cAbl_IRF1 | 0.00775 | 0.006488 | 0.171717 | 0.04288 | 0.00249 | 0.050468 |
| 5 | AR_RelA_cAbl_SUMO1_IRF1 | 0.071803 | 0.052182 | 0.031855 | 0.021335 | 0.002509 | 0.003609 |
| 5 | RelA_cAbl_SUMO1_CDK1_IRF1 | 0.071803 | 0.043714 | 0.031855 | 0.019832 | 0.002509 | 0.001974 |
| 5 | RelA_cAbl_SUMO1_HDAC_IRF1 | 0.071803 | 0.04079 | 0.031855 | 0.019511 | 0.002509 | 0.001853 |
| 5 | AR_cAbl_SUMO1_HDAC_IRF1 | 0.035987 | 0.045922 | 0.031855 | 0.020208 | 0.003416 | 0.003874 |
| 5 | cAbl_SUMO1_CDK1_HDAC_IRF1 | 0.035987 | 0.026992 | 0.031855 | 0.016298 | 0.003416 | 0.001414 |
| 5 | PKC_cAbl_SUMO1_HDAC_IRF1 | 0.035987 | 0.065218 | 0.031855 | 0.023045 | 0.003416 | 0.007044 |
| 5 | cjun_RelA_cAbl_SUMO1_IRF1 | 0.024978 | 0.050534 | 0.163226 | 0.077524 | 0.003684 | 0.088779 |
| 5 | AR_STAT1_cAbl_CDK1_IRF1 | 0.012241 | 0.010091 | 0.105 | 0.028862 | 0.004029 | 0.001136 |
| 5 | STAT1_cAbl_CDK1_HDAC_IRF1 | 0.012241 | 0.010324 | 0.05616 | 0.023879 | 0.004827 | 0.001772 |
| 5 | STAT1_cAbl_SUMO1_CDK1_IRF1 | 0.027078 | 0.03174 | 0.05616 | 0.031267 | 0.006116 | 0.005047 |
| 5 | STAT1_cAbl_SUMO1_HDAC_IRF1 | 0.027078 | 0.031937 | 0.05616 | 0.031378 | 0.006116 | 0.005087 |
| 5 | AR_STAT1_cAbl_HDAC_IRF1 | 0.012241 | 0.01002 | 0.105 | 0.02639 | 0.006545 | 0.001461 |
| 5 | STAT1_PKC_cAbl_HDAC_IRF1 | 0.012241 | 0.0099 | 0.105 | 0.027443 | 0.006545 | 0.001468 |
| 5 | PKC_cAbl_SUMO1_CDK1_IRF1 | 0.048608 | 0.049043 | 0.069516 | 0.020776 | 0.007122 | 0.004403 |

FIG. 4C

| | | | | | | |
|---|---|---|---|---|---|---|
| 5 | cjun_RelA_cAbl_HDAC_IRF1 | 0.005544 | 0.010005 | 0.230079 | 0.185056 | 0.008124 | 0.010078 |
| 5 | STAT1_PKC_cAbl_CDK1_IRF1 | 0.016187 | 0.009935 | 0.031867 | 0.026411 | 0.008371 | 0.001536 |
| 5 | cjun_PKC_cAbl_CDK1_IRF1 | 0.005135 | 0.008693 | 0.163226 | 0.119096 | 0.008862 | 0.013361 |
| 5 | AR_cjun_cAbl_CDK1_IRF1 | 0.005544 | 0.008881 | 0.180301 | 0.096098 | 0.009301 | 0.00587 |
| 5 | AR_STAT1_cAbl_SUMO1_IRF1 | 0.027078 | 0.035793 | 0.105 | 0.035736 | 0.010883 | 0.00584 |
| 5 | AR_cjun_cAbl_HDAC_IRF1 | 0.005544 | 0.010834 | 0.229678 | 0.222713 | 0.012743 | 0.03173 |
| 5 | AR_cjun_PKC_cAbl_IRF1 | 0.012241 | 0.011669 | 0.105 | 0.03646 | 0.012877 | 0.061831 |
| 5 | AR_PKC_cAbl_SUMO1_IRF1 | 0.039987 | 0.066176 | 0.031855 | 0.023169 | 0.013137 | 0.067223 |
| 5 | AR_cjun_STAT1_cAbl_IRF1 | 0.007692 | 0.007384 | 0.207578 | 0.03468 | 0.013228 | 0.00692 |
| 5 | cjun_STAT1_cAbl_HDAC_IRF1 | 0.010946 | 0.006737 | 0.164506 | 0.09287 | 0.013307 | 0.009431 |
| 5 | AR_PKC_cAbl_HDAC_IRF1 | 0.005373 | 0.012516 | 0.029853 | 0.01501 | 0.013698 | 0.000581 |
| 5 | STAT1_PKC_cAbl_SUMO1_IRF1 | 0.027078 | 0.048737 | 0.105 | 0.037432 | 0.014301 | 0.009521 |
| 5 | cjun_cAbl_CDK1_HDAC_IRF1 | 0.005544 | 0.0072 | 0.182909 | 0.053275 | 0.014624 | 0.093184 |
| 5 | AR_STAT1_cAbl_CDK1_IRF1 | 0.007692 | 0.006129 | 0.257239 | 0.053273 | 0.015109 | 0.004942 |
| 5 | cjun_STAT1_cAbl_CDK1_IRF1 | 0.010946 | 0.008103 | 0.207578 | 0.121362 | 0.015109 | 0.015116 |
| 5 | cjun_PKC_cAbl_SUMO1_IRF1 | 0.005544 | 0.011844 | 0.180301 | 0.179411 | 0.020871 | 0.031357 |
| 5 | AR_cjun_PKC_cAbl_IRF1 | 0.025754 | 0.038869 | 0.207578 | 0.063736 | 0.021231 | 0.017927 |
| 5 | cjun_STAT1_cAbl_SUMO1_IRF1 | 0.033842 | 0.052453 | 0.161933 | 0.103629 | 0.023319 | 0.029437 |
| 5 | AR_cjun_cAbl_SUMO1_IRF1 | 0.033842 | 0.036469 | 0.161933 | 0.061079 | 0.023319 | 0.011485 |
| 5 | cjun_cAbl_SUMO1_CDK1_IRF1 | 0.033842 | 0.064812 | 0.207167 | 0.173122 | 0.025699 | 0.051116 |
| 5 | cjun_cAbl_SUMO1_HDAC_IRF1 | 0.033842 | 0.07837 | 0.161933 | 0.144744 | 0.026402 | 0.058614 |
| 5 | cjun_PKC_cAbl_SUMO1_IRF1 | 0.025036 | 0.012951 | 0.402595 | 0.285581 | 0.050314 | 0.061851 |
| 5 | cjun_PKC_cAbl_HDAC_IRF1 | 0.012328 | 0.010183 | 0.024243 | 0.018468 | 0.004401 | 0.000193 |
| 6 | AR_STAT1_RelA_cAbl_HDAC_IRF1 | 0.012328 | 0.010253 | 0.024243 | 0.015029 | 0.004401 | 0.000159 |
| 6 | STAT1_PKC_RelA_cAbl_HDAC_IRF1 | 0.006254 | 0.012146 | 0.033537 | 0.014466 | 0.000423 | 0.000208 |
| 6 | AR_PKC_cAbl_CDK1_HDAC_IRF1 | 0.006254 | 0.012373 | 0.033537 | 0.014792 | 0.000423 | 0.000518 |
| 6 | AR_PKC_RelA_cAbl_CDK1_IRF1 | 0.006254 | 0.012423 | 0.033537 | 0.014867 | 0.000423 | 0.000138 |
| 6 | PKC_RelA_cAbl_CDK1_HDAC_IRF1 | 0.016289 | 0.01018 | 0.024848 | 0.016925 | 0.000458 | 0.000173 |
| 6 | STAT1_PKC_RelA_cAbl_CDK1_IRF1 | 0.005373 | 0.012516 | 0.029853 | 0.01501 | 0.000492 | 0.000909 |
| 6 | AR_PKC_RelA_cAbl_HDAC_IRF1 | 0.005373 | 0.012516 | 0.029853 | 0.01501 | 0.000492 | 0.000247 |
| 6 | AR_RelA_cAbl_CDK1_HDAC_IRF1 | 0.012328 | 0.011391 | 0.069461 | 0.022067 | 0.000699 | 0.000305 |
| 6 | AR_STAT1_PKC_RelA_cAbl_IRF1 | 0.012328 | 0.013371 | 0.069461 | 0.019948 | 0.000699 | 0.000208 |
| 6 | AR_cjun_PKC_RelA_cAbl_IRF1 | 0.005544 | 0.010787 | 0.181613 | 0.141533 | 0.000994 | 0.00526 |
| 6 | AR_cjun_RelA_cAbl_CDK1_IRF1 | 0.005544 | 0.00858 | 0.181613 | 0.077553 | 0.000994 | 0.001241 |
| 6 | STAT1_PKC_RelA_cAbl_SUMO1_IRF1 | 0.025625 | 0.049104 | 0.024243 | 0.025713 | 0.001171 | 0.002455 |
| 6 | STAT1_RelA_cAbl_CDK1_HDAC_IRF1 | 0.012328 | 0.010473 | 0.035251 | 0.015351 | 0.001191 | 0.000335 |
| 6 | AR_PKC_RelA_cAbl_SUMO1_IRF1 | 0.031347 | 0.064351 | 0.031855 | 0.022809 | 0.001515 | 0.005786 |
| 6 | PKC_RelA_cAbl_SUMO1_HDAC_IRF1 | 0.031347 | 0.069955 | 0.031855 | 0.0223 | 0.001515 | 0.004544 |

FIG. 4D

| | | | | | |
|---|---|---|---|---|---|
| 6 | STAT1_RelA_cAbl_SUMO1_CDK1_IRF1 | 0.034423 | 0.035618 | 0.035251 | 0.023496 | 0.001647 | 0.001711 |
| 6 | STAT1_RelA_cAbl_SUMO1_HDAC_IRF1 | 0.034423 | 0.033606 | 0.035251 | 0.022447 | 0.001647 | 0.001495 |
| 6 | AR_cAbl_SUMO1_CDK1_HDAC_IRF1 | 0.035987 | 0.032426 | 0.031855 | 0.017695 | 0.00176 | 0.001421 |
| 6 | AR_PKC_cAbl_SUMO1_HDAC_IRF1 | 0.035987 | 0.061502 | 0.031855 | 0.022549 | 0.00176 | 0.006293 |
| 6 | cjun_STAT1_RelA_cAbl_CDK1_IRF1 | 0.00775 | 0.00607 | 0.10101 | 0.033408 | 0.001793 | 0.000384 |
| 6 | PKC_RelA_cAbl_SUMO1_CDK1_IRF1 | 0.031807 | 0.056849 | 0.069516 | 0.021613 | 0.001962 | 0.003289 |
| 6 | cjun_RelA_cAbl_SUMO1_CDK1_IRF1 | 0.005544 | 0.007057 | 0.183338 | 0.046268 | 0.001997 | 0.000449 |
| 6 | AR_STAT1_cAbl_CDK1_HDAC_IRF1 | 0.012241 | 0.009818 | 0.05616 | 0.02584 | 0.002121 | 0.001012 |
| 6 | AR_STAT1_RelA_SUMO1_HDAC_IRF1 | 0.034423 | 0.038731 | 0.069461 | 0.027219 | 0.002292 | 0.001935 |
| 6 | cjun_STAT1_PKC_RelA_cAbl_IRF1 | 0.00775 | 0.00756 | 0.171717 | 0.067197 | 0.00249 | 0.000985 |
| 6 | cjun_STAT1_RelA_cAbl_HDAC_IRF1 | 0.00775 | 0.006331 | 0.171717 | 0.043571 | 0.00249 | 0.000547 |
| 6 | AR_RelA_cAbl_SUMO1_CDK1_IRF1 | 0.071803 | 0.049857 | 0.031855 | 0.020885 | 0.002509 | 0.003047 |
| 6 | AR_RelA_cAbl_SUMO1_HDAC_IRF1 | 0.071803 | 0.047364 | 0.031855 | 0.020697 | 0.002509 | 0.003038 |
| 6 | RelA_cAbl_SUMO1_CDK1_HDAC_IRF1 | 0.071803 | 0.030207 | 0.031855 | 0.017315 | 0.002509 | 0.001083 |
| 6 | AR_PKC_cAbl_SUMO1_CDK1_IRF1 | 0.048608 | 0.053942 | 0.069516 | 0.021485 | 0.002583 | 0.004352 |
| 6 | AR_cjun_RelA_cAbl_SUMO1_IRF1 | 0.024978 | 0.046139 | 0.163226 | 0.076913 | 0.002686 | 0.007784 |
| 6 | cjun_PKC_RelA_cAbl_CDK1_IRF1 | 0.011037 | 0.099387 | 0.206754 | 0.103253 | 0.002703 | 0.002193 |
| 6 | AR_cjun_STAT1_RelA_cAbl_IRF1 | 0.00775 | 0.007314 | 0.215909 | 0.052108 | 0.002922 | 0.000573 |
| 6 | cjun_STAT1_RelA_SUMO1_HDAC_IRF1 | 0.022576 | 0.034537 | 0.133838 | 0.041699 | 0.002969 | 0.002907 |
| 6 | STAT1_PKC_cAbl_CDK1_HDAC_IRF1 | 0.011498 | 0.009966 | 0.042689 | 0.024049 | 0.003337 | 0.001642 |
| 6 | cjun_PKC_RelA_cAbl_SUMO1_IRF1 | 0.024978 | 0.063469 | 0.163226 | 0.108402 | 0.004298 | 0.016925 |
| 6 | cjun_RelA_cAbl_SUMO1_HDAC_IRF1 | 0.024978 | 0.038872 | 0.163226 | 0.058253 | 0.004298 | 0.004779 |
| 6 | AR_cjun_RelA_cAbl_HDAC_IRF1 | 0.005544 | 0.009597 | 0.230079 | 0.170543 | 0.004467 | 0.008449 |
| 6 | cjun_PKC_RelA_cAbl_HDAC_IRF1 | 0.005544 | 0.01117 | 0.230079 | 0.225442 | 0.004467 | 0.019243 |
| 6 | AR_STAT1_PKC_cAbl_CDK1_IRF1 | 0.016187 | 0.010505 | 0.14345 | 0.030853 | 0.00525 | 0.001409 |
| 6 | AR_STAT1_cAbl_SUMO1_CDK1_IRF1 | 0.027078 | 0.034775 | 0.105 | 0.034158 | 0.005623 | 0.005105 |
| 6 | STAT1_cAbl_SUMO1_CDK1_HDAC_IRF1 | 0.027078 | 0.025757 | 0.05616 | 0.028858 | 0.006116 | 0.003744 |
| 6 | PKC_cAbl_SUMO1_CDK1_HDAC_IRF1 | 0.048608 | 0.035703 | 0.069516 | 0.018408 | 0.007122 | 0.002493 |
| 6 | AR_cjun_PKC_cAbl_CDK1_IRF1 | 0.005135 | 0.009658 | 0.163226 | 0.12472 | 0.007881 | 0.010218 |
| 6 | STAT1_PKC_cAbl_SUMO1_HDAC_IRF1 | 0.027078 | 0.044108 | 0.05616 | 0.035228 | 0.0082 | 0.008225 |
| 6 | AR_cjun_cAbl_CDK1_HDAC_IRF1 | 0.005544 | 0.007509 | 0.182909 | 0.064698 | 0.009364 | 0.002029 |
| 6 | cjun_STAT1_cAbl_CDK1_HDAC_IRF1 | 0.007692 | 0.006365 | 0.127395 | 0.033087 | 0.01013 | 0.003676 |
| 6 | AR_cjun_PKC_RelA_cAbl_IRF1 | 0.024978 | 0.047647 | 0.207578 | 0.118799 | 0.010315 | 0.014522 |
| 6 | cjun_RelA_SUMO1_CDK1_HDAC_IRF1 | 0.005135 | 0.009024 | 0.163655 | 0.069466 | 0.01036 | 0.005447 |
| 6 | cjun_PKC_cAbl_CDK1_HDAC_IRF1 | 0.027078 | 0.033598 | 0.105 | 0.034069 | 0.010863 | 0.005298 |
| 6 | AR_STAT1_PKC_SUMO1_HDAC_IRF1 | 0.028623 | 0.042587 | 0.081867 | 0.034391 | 0.012316 | 0.006062 |
| 6 | STAT1_PKC_cAbl_SUMO1_CDK1_IRF1 | 0.007692 | 0.006496 | 0.207578 | 0.066016 | 0.012629 | 0.003859 |
| 6 | AR_cjun_STAT1_cAbl_CDK1_IRF1 | 0.012241 | 0.010742 | 0.105 | 0.032282 | 0.012877 | 0.001566 |

FIG. 4E

| | | | | | | |
|---|---|---|---|---|---|---|
| 6 | cjun_STAT1_PKC_cAbl_HDAC_IRF1 | 0.010946 | 0.007323 | 0.164506 | 0.119822 | 0.013307 | 0.013075 |
| 6 | AR_cjun_STAT1_cAbl_HDAC_IRF1 | 0.007692 | 0.006711 | 0.257608 | 0.085066 | 0.015195 | 0.006388 |
| 6 | cjun_STAT1_PKC_cAbl_CDK1_IRF1 | 0.009594 | 0.006542 | 0.215909 | 0.07053 | 0.015453 | 0.007037 |
| 6 | AR_cjun_STAT1_PKC_cAbl_IRF1 | 0.007692 | 0.009583 | 0.257239 | 0.127366 | 0.016447 | 0.014161 |
| 6 | AR_cjun_STAT1_PKC_cAbl_IRF1 | 0.027078 | 0.044837 | 0.105 | 0.040217 | 0.017137 | 0.008466 |
| 6 | AR_STAT1_PKC_cAbl_SUMO1_IRF1 | 0.033842 | 0.022313 | 0.126559 | 0.030769 | 0.017598 | 0.003126 |
| 6 | cjun_cAbl_SUMO1_CDK1_HDAC_IRF1 | 0.005544 | 0.011795 | 0.229678 | 0.255512 | 0.018455 | 0.04568 |
| 6 | AR_cjun_PKC_cAbl_HDAC_IRF1 | 0.025754 | 0.029471 | 0.164081 | 0.046392 | 0.018716 | 0.010236 |
| 6 | cjun_STAT1_cAbl_SUMO1_CDK1_IRF1 | 0.033842 | 0.030099 | 0.161933 | 0.071591 | 0.02063 | 0.011614 |
| 6 | AR_cjun_PKC_cAbl_SUMO1_IRF1 | 0.033842 | 0.064144 | 0.161933 | 0.132742 | 0.02063 | 0.045129 |
| 6 | AR_cjun_STAT1_cAbl_SUMO1_IRF1 | 0.025754 | 0.031235 | 0.207578 | 0.067798 | 0.021231 | 0.013386 |
| 6 | cjun_STAT1_PKC_cAbl_SUMO1_IRF1 | 0.025754 | 0.047932 | 0.207578 | 0.095037 | 0.021231 | 0.031418 |
| 6 | cjun_cAbl_SUMO1_HDAC_IRF1 | 0.025754 | 0.035755 | 0.257608 | 0.063489 | 0.024062 | 0.015452 |
| 6 | AR_cjun_PKC_SUMO1_HDAC_IRF1 | 0.033842 | 0.050225 | 0.207167 | 0.153353 | 0.025699 | 0.035749 |
| 6 | cjun_PKC_cAbl_SUMO1_HDAC_IRF1 | 0.033842 | 0.075048 | 0.207167 | 0.20267 | 0.029014 | 0.069481 |
| 6 | cjun_PKC_cAbl_SUMO1_CDK1_IRF1 | 0.042499 | 0.045654 | 0.185036 | 0.031677 | 0.031556 | 0.02001 |
| 7 | AR_PKC_RelA_SUMO1_CDK1_HDAC_IRF1 | 0.006254 | 0.012392 | 0.033537 | 0.01482 | 0.000423 | 0.000335 |
| 7 | AR_STAT1_PKC_cAbl_SUMO1_CDK1_HDAC_IRF1 | 0.012328 | 0.01068 | 0.069461 | 0.01926 | 0.000698 | 0.000219 |
| 7 | AR_STAT1_RelA_cAbl_CDK1_HDAC_IRF1 | 0.013328 | 0.010031 | 0.024243 | 0.017542 | 0.000699 | 0.000201 |
| 7 | AR_STAT1_PKC_cAbl_CDK1_HDAC_IRF1 | 0.018289 | 0.01078 | 0.07052 | 0.021098 | 0.000793 | 0.000234 |
| 7 | AR_STAT1_PKC_RelA_cAbl_CDK1_IRF1 | 0.011579 | 0.019273 | 0.036008 | 0.014773 | 0.000793 | 0.000215 |
| 7 | STAT1_PKC_RelA_cAbl_SUMO1_CDK1_IRF1 | 0.005135 | 0.009473 | 0.163226 | 0.107099 | 0.000819 | 0.002659 |
| 7 | AR_cjun_PKC_RelA_cAbl_CDK1_IRF1 | 0.005544 | 0.007478 | 0.183338 | 0.057203 | 0.001001 | 0.000703 |
| 7 | STAT1_PKC_RelA_cAbl_SUMO1_CDK1_HDAC_IRF1 | 0.025754 | 0.044779 | 0.024848 | 0.024918 | 0.00118 | 0.002274 |
| 7 | cjun_STAT1_RelA_cAbl_CDK1_HDAC_IRF1 | 0.00775 | 0.066095 | 0.05303 | 0.019696 | 0.001279 | 0.000364 |
| 7 | AR_STAT1_RelA_SUMO1_CDK1_IRF1 | 0.034423 | 0.037737 | 0.024243 | 0.026474 | 0.001391 | 0.00184 |
| 7 | AR_STAT1_RelA_cAbl_SUMO1_CDK1_IRF1 | 0.034423 | 0.035309 | 0.024243 | 0.02531 | 0.001391 | 0.001625 |
| 7 | AR_STAT1_RelA_cAbl_SUMO1_HDAC_IRF1 | 0.034423 | 0.043897 | 0.024243 | 0.023424 | 0.001391 | 0.001943 |
| 7 | STAT1_PKC_RelA_cAbl_SUMO1_HDAC_IRF1 | 0.071803 | 0.03479 | 0.031855 | 0.01847 | 0.001515 | 0.001789 |
| 7 | AR_RelA_SUMO1_CDK1_HDAC_IRF1 | 0.025625 | 0.045942 | 0.069461 | 0.029308 | 0.001647 | 0.002624 |
| 7 | AR_STAT1_PKC_RelA_SUMO1_CDK1_IRF1 | 0.034423 | 0.02277 | 0.035251 | 0.020527 | 0.001647 | 0.0013 |
| 7 | AR_cjun_STAT1_RelA_cAbl_CDK1_IRF1 | 0.00775 | 0.03685 | 0.215909 | 0.016417 | 0.001793 | 0.000471 |
| 7 | AR_STAT1_RelA_SUMO1_HDAC_IRF1 | 0.031807 | 0.058474 | 0.069516 | 0.021983 | 0.001962 | 0.004093 |
| 7 | AR_STAT1_RelA_cAbl_SUMO1_HDAC_IRF1 | 0.00775 | 0.066576 | 0.171717 | 0.049132 | 0.002116 | 0.000516 |
| 7 | AR_PKC_RelA_cAbl_SUMO1_HDAC_IRF1 | 0.071803 | 0.05593 | 0.031855 | 0.022266 | 0.002509 | 0.005093 |
| 7 | cjun_STAT1_RelA_SUMO1_HDAC_IRF1 | 0.022576 | 0.031397 | 0.10101 | 0.037275 | 0.002531 | 0.002325 |
| 7 | AR_PKC_RelA_cAbl_SUMO1_CDK1_HDAC_IRF1 | 0.048608 | 0.04046 | 0.069516 | 0.019307 | 0.002583 | 0.002288 |
| 7 | AR_cjun_PKC_RelA_cAbl_SUMO1_IRF1 | 0.024978 | 0.056438 | 0.163226 | 0.104218 | 0.002686 | 0.014218 |

FIG. 4F

| | | | | | |
|---|---|---|---|---|---|
| 7 | cjun_PKC_RelA_cAbl_CDK1_HDAC_IRF1 | 0.011037 | 0.03803 | 0.207167 | 0.065821 | 0.002707 | 0.000838 |
| 7 | AR_cjun_STAT1_PKC_RelA_cAbl_IRF1 | 0.00775 | 0.006087 | 0.215909 | 0.082321 | 0.002922 | 0.001461 |
| 7 | cjun_STAT1_PKC_RelA_cAbl_HDAC_IRF1 | 0.00775 | 0.006934 | 0.215909 | 0.063091 | 0.002922 | 0.000907 |
| 7 | cjun_STAT1_RelA_PKC_cAbl_SUMO1_CDK1_IRF1 | 0.022576 | 0.02922 | 0.10101 | 0.036237 | 0.002969 | 0.002303 |
| 7 | cjun_STAT1_PKC_RelA_cAbl_CDK1_IRF1 | 0.009661 | 0.00667 | 0.171717 | 0.047645 | 0.00319 | 0.000591 |
| 7 | PKC_RelA_cAbl_SUMO1_CDK1_HDAC_IRF1 | 0.072502 | 0.036656 | 0.069516 | 0.019237 | 0.003197 | 0.00165 |
| 7 | AR_STAT1_PKC_cAbl_SUMO1_CDK1_HDAC_IRF1 | 0.016187 | 0.009878 | 0.081867 | 0.026367 | 0.003868 | 0.00135 |
| 7 | AR_STAT1_cAbl_SUMO1_CDK1_HDAC_IRF1 | 0.027078 | 0.028597 | 0.05616 | 0.030819 | 0.004151 | 0.003491 |
| 7 | AR_cjun_RelA_cAbl_SUMO1_CDK1_HDAC_IRF1 | 0.058409 | 0.093324 | 0.163226 | 0.063234 | 0.004298 | 0.005112 |
| 7 | AR_cjun_PKC_RelA_cAbl_HDAC_IRF1 | 0.085544 | 0.019755 | 0.230079 | 0.214721 | 0.004467 | 0.017079 |
| 7 | cjun_PKC_RelA_cAbl_SUMO1_CDK1_IRF1 | 0.025366 | 0.048188 | 0.185036 | 0.078328 | 0.005426 | 0.008649 |
| 7 | AR_cjun_STAT1_cAbl_HDAC_IRF1 | 0.058409 | 0.024893 | 0.126978 | 0.031879 | 0.005822 | 0.001447 |
| 7 | AR_RelA_cAbl_SUMO1_CDK1_HDAC_IRF1 | 0.022576 | 0.03117 | 0.215909 | 0.04912 | 0.006358 | 0.002903 |
| 7 | AR_cjun_STAT1_RelA_cAbl_SUMO1_IRF1 | 0.022576 | 0.041755 | 0.163909 | 0.061868 | 0.007349 | 0.005582 |
| 7 | AR_cjun_PKC_RelA_cAbl_CDK1_IRF1 | 0.065135 | 0.008286 | 0.163655 | 0.091635 | 0.00789 | 0.004051 |
| 7 | AR_STAT1_PKC_cAbl_CDK1_HDAC_IRF1 | 0.027078 | 0.043863 | 0.105 | 0.037454 | 0.008699 | 0.007017 |
| 7 | cjun_PKC_RelA_cAbl_SUMO1_CDK1_HDAC_IRF1 | 0.024978 | 0.063351 | 0.207578 | 0.156636 | 0.010315 | 0.02788 |
| 7 | STAT1_PKC_RelA_cAbl_SUMO1_CDK1_HDAC_IRF1 | 0.026623 | 0.039939 | 0.081867 | 0.031082 | 0.010742 | 0.005847 |
| 7 | AR_cjun_RelA_cAbl_SUMO1_CDK1_IRF1 | 0.058409 | 0.044277 | 0.207578 | 0.120193 | 0.011828 | 0.013925 |
| 7 | AR_cjun_STAT1_PKC_cAbl_CDK1_IRF1 | 0.066718 | 0.007408 | 0.215909 | 0.088238 | 0.0119 | 0.006443 |
| 7 | AR_STAT1_cAbl_CDK1_HDAC_IRF1 | 0.007692 | 0.005729 | 0.164506 | 0.041097 | 0.012641 | 0.002697 |
| 7 | AR_cjun_STAT1_cAbl_CDK1_HDAC_IRF1 | 0.009594 | 0.006427 | 0.171717 | 0.039677 | 0.015496 | 0.004802 |
| 7 | AR_cjun_cAbl_SUMO1_CDK1_HDAC_IRF1 | 0.033842 | 0.025812 | 0.163655 | 0.043897 | 0.016013 | 0.003737 |
| 7 | AR_cjun_STAT1_PKC_cAbl_HDAC_IRF1 | 0.007692 | 0.006167 | 0.257608 | 0.122578 | 0.016462 | 0.011719 |
| 7 | cjun_STAT1_cAbl_SUMO1_CDK1_HDAC_IRF1 | 0.025754 | 0.023383 | 0.096548 | 0.029309 | 0.016507 | 0.006024 |
| 7 | AR_STAT1_PKC_cAbl_SUMO1_CDK1_IRF1 | 0.026623 | 0.041336 | 0.14345 | 0.036431 | 0.017481 | 0.007555 |
| 7 | AR_cjun_PKC_cAbl_SUMO1_CDK1_IRF1 | 0.031807 | 0.046776 | 0.14473 | 0.092813 | 0.018538 | 0.019118 |
| 7 | cjun_PKC_cAbl_SUMO1_CDK1_HDAC_IRF1 | 0.025754 | 0.043603 | 0.164506 | 0.090624 | 0.018767 | 0.026601 |
| 7 | AR_cjun_STAT1_PKC_SUMO1_CDK1_IRF1 | 0.025754 | 0.026978 | 0.207578 | 0.054953 | 0.02006 | 0.008515 |
| 7 | AR_cjun_STAT1_RelA_cAbl_SUMO1_IRF1 | 0.025754 | 0.039205 | 0.257239 | 0.097387 | 0.022721 | 0.024095 |
| 7 | AR_cjun_PKC_cAbl_SUMO1_IRF1 | 0.033842 | 0.061801 | 0.207167 | 0.188762 | 0.023345 | 0.054635 |
| 7 | AR_cjun_PKC_cAbl_SUMO1_HDAC_IRF1 | 0.025754 | 0.026323 | 0.257608 | 0.066011 | 0.024082 | 0.011314 |
| 7 | cjun_STAT1_PKC_cAbl_SUMO1_CDK1_IRF1 | 0.026144 | 0.036562 | 0.265152 | 0.060792 | 0.025733 | 0.016539 |
| 7 | cjun_PKC_cAbl_SUMO1_CDK1_HDAC_IRF1 | 0.042499 | 0.030077 | 0.185457 | 0.046066 | 0.030209 | 0.00722 |
| 8 | AR_STAT1_PKC_RelA_cAbl_CDK1_HDAC_IRF1 | 0.016239 | 0.010145 | 0.024848 | 0.017279 | 0.000458 | 0.000185 |
| 8 | AR_cjun_PKC_RelA_cAbl_CDK1_HDAC_IRF1 | 0.005135 | 0.00832 | 0.163655 | 0.084205 | 0.00082 | 0.001617 |
| 8 | AR_cjun_STAT1_RelA_cAbl_CDK1_HDAC_IRF1 | 0.00775 | 0.005887 | 0.06303 | 0.027916 | 0.000903 | 0.000291 |
| 8 | AR_STAT1_RelA_cAbl_SUMO1_CDK1_HDAC_IRF1 | 0.034423 | 0.036058 | 0.035251 | 0.022593 | 0.001647 | 0.001231 |

FIG. 4G

| | | | | | | | |
|---|---|---|---|---|---|---|---|
| 8 | STAT1_PKC_RelA_cAbl_SUMO1_CDK1_HDAC_IRF1 | 0.034576 | 0.035445 | 0.036008 | 0.020993 | 0.001658 | 0.001649 |
| 8 | cjun_STAT1_RelA_cAbl_SUMO1_CDK1_HDAC_IRF1 | 0.030465 | 0.02203 | 0.036616 | 0.020386 | 0.001825 | 0.001244 |
| 8 | AR_STAT1_PKC_RelA_cAbl_SUMO1_CDK1_HDAC_IRF1 | 0.034423 | 0.041656 | 0.069461 | 0.026673 | 0.001945 | 0.002052 |
| 8 | AR_STAT1_PKC_RelA_cAbl_SUMO1_CDK1_IRF1 | 0.025754 | 0.043679 | 0.07052 | 0.027865 | 0.001958 | 0.002373 |
| 8 | cjun_STAT1_PKC_RelA_cAbl_SUMO1_CDK1_HDAC_IRF1 | 0.009661 | 0.006321 | 0.10101 | 0.025196 | 0.001967 | 0.000401 |
| 8 | AR_cjun_PKC_RelA_cAbl_SUMO1_CDK1_IRF1 | 0.025366 | 0.047363 | 0.185036 | 0.062853 | 0.002931 | 0.009875 |
| 8 | AR_cjun_STAT1_RelA_cAbl_SUMO1_CDK1_HDAC_IRF1 | 0.030465 | 0.028026 | 0.10101 | 0.044116 | 0.092969 | 0.002231 |
| 8 | AR_cjun_RelA_cAbl_SUMO1_CDK1_HDAC_IRF1 | 0.058109 | 0.02761 | 0.164081 | 0.049722 | 0.003159 | 0.002158 |
| 8 | AR_STAT1_PKC_RelA_cAbl_CDK1_IRF1 | 0.009661 | 0.007752 | 0.215909 | 0.065108 | 0.00319 | 0.000856 |
| 8 | AR_PKC_RelA_cAbl_SUMO1_CDK1_HDAC_IRF1 | 0.072502 | 0.042387 | 0.069516 | 0.019942 | 0.093197 | 0.002454 |
| 8 | AR_cjun_STAT1_PKC_RelA_cAbl_HDAC_IRF1 | 0.00775 | 0.007683 | 0.265152 | 0.075652 | 0.003422 | 0.001128 |
| 8 | cjun_STAT1_PKC_RelA_cAbl_SUMO1_CDK1_IRF1 | 0.021312 | 0.035229 | 0.133836 | 0.043366 | 0.00385 | 0.003831 |
| 8 | AR_STAT1_PKC_RelA_cAbl_SUMO1_HDAC_IRF1 | 0.022576 | 0.037773 | 0.171717 | 0.054436 | 0.094723 | 0.004185 |
| 8 | AR_cjun_STAT1_RelA_cAbl_SUMO1_CDK1_IRF1 | 0.022576 | 0.028307 | 0.215909 | 0.044477 | 0.005487 | 0.002342 |
| 8 | cjun_PKC_RelA_cAbl_SUMO1_CDK1_HDAC_IRF1 | 0.059027 | 0.031936 | 0.185457 | 0.045287 | 0.007282 | 0.002907 |
| 8 | AR_cjun_STAT1_PKC_RelA_cAbl_SUMO1_IRF1 | 0.022576 | 0.037143 | 0.215909 | 0.069659 | 0.007349 | 0.005366 |
| 8 | AR_cjun_PKC_RelA_cAbl_SUMO1_HDAC_IRF1 | 0.024978 | 0.054192 | 0.207578 | 0.154509 | 0.007737 | 0.024759 |
| 8 | AR_STAT1_PKC_cAbl_SUMO1_CDK1_HDAC_IRF1 | 0.028623 | 0.034391 | 0.081867 | 0.03255 | 0.009814 | 0.055593 |
| 8 | cjun_STAT1_PKC_cAbl_SUMO1_CDK1_HDAC_IRF1 | 0.009594 | 0.006081 | 0.133838 | 0.051547 | 0.0119 | 0.004367 |
| 8 | AR_cjun_STAT1_cAbl_SUMO1_CDK1_HDAC_IRF1 | 0.025754 | 0.020968 | 0.096548 | 0.056039 | 0.01554 | 0.005293 |
| 8 | cjun_STAT1_PKC_RelA_cAbl_SUMO1_CDK1_HDAC_IRF1 | 0.026144 | 0.029198 | 0.10101 | 0.035609 | 0.017732 | 0.009919 |
| 8 | AR_cjun_STAT1_PKC_cAbl_SUMO1_CDK1_HDAC_IRF1 | 0.042499 | 0.033596 | 0.185457 | 0.063779 | 0.018554 | 0.007542 |
| 8 | AR_cjun_PKC_RelA_cAbl_SUMO1_CDK1_IRF1 | 0.026144 | 0.032338 | 0.215909 | 0.068709 | 0.020146 | 0.013484 |
| 8 | AR_cjun_STAT1_PKC_RelA_SUMO1_HDAC_IRF1 | 0.025754 | 0.035138 | 0.257608 | 0.092676 | 0.022739 | 0.019513 |
| 9 | AR_STAT1_PKC_RelA_cAbl_SUMO1_CDK1_HDAC_IRF1 | 0.034578 | 0.035618 | 0.036308 | 0.023172 | 0.001658 | 0.001538 |
| 9 | AR_cjun_STAT1_PKC_cAbl_SUMO1_CDK1_HDAC_IRF1 | 0.030465 | 0.021804 | 0.036616 | 0.026969 | 0.001825 | 0.001187 |
| 9 | cjun_STAT1_PKC_RelA_cAbl_SUMO1_CDK1_HDAC_IRF1 | 0.029637 | 0.027548 | 0.05303 | 0.025315 | 0.001841 | 0.001859 |
| 9 | AR_cjun_STAT1_PKC_RelA_cAbl_CDK1_HDAC_IRF1 | 0.009661 | 0.006329 | 0.133838 | 0.036732 | 0.002317 | 0.000408 |
| 9 | AR_cjun_PKC_RelA_cAbl_SUMO1_CDK1_HDAC_IRF1 | 0.059027 | 0.034465 | 0.185457 | 0.058656 | 0.0040:3 | 0.004148 |
| 9 | AR_cjun_STAT1_PKC_RelA_cAbl_SUMO1_CDK1_IRF1 | 0.021312 | 0.033083 | 0.215909 | 0.056914 | 0.096386 | 0.003777 |
| 9 | AR_cjun_STAT1_PKC_RelA_cAbl_SUMO1_CDK1_HDAC | 0.022576 | 0.033295 | 0.265152 | 0.062515 | 0.007349 | 0.004032 |
| 9 | AR_cjun_STAT1_PKC_RelA_cAbl_SUMO1_CDK1_HDAC_IRF1 | 0.026144 | 0.025958 | 0.10101 | 0.042328 | 0.017747 | 0.008551 |
| 10 | AR_cjun_STAT1_PKC_RelA_cAbl_SUMO1_CDK1_HDAC_IRF1 | 0.029637 | 0.026072 | 0.05303 | 0.032947 | 0.001511 | 0.001769 |

FIG. 6A

| Probe Set ID | Gene Title | Gene Symbol |
|---|---|---|
| L03411_s_at | RD RNA binding protein | RDBP |
| AB000468_at | ring finger protein 4 | RNF4 |
| X90568_at | titin | TTN |
| HG2147-HT2217_at | — | — |
| X57152_rna1_s_at | casein kinase 2, beta polypeptide | CSNK2B |
| U67156_at | mitogen-activated protein kinase kinase kinase 5 | MAP3K5 |
| L01664_at | Charcot-Leyden crystal protein | CLC |
| HG3991-HT4261_r_at | — | — |
| U05012_s_at | neurotrophic tyrosine kinase, receptor, type 3 | NTRK3 |
| U34360_at | AF4/FMR2 family, member 3 | AFF3 |
| U14970_at | ribosomal protein S5 | RPS5 |
| X58401_at | (cell line: L3B6) Ig rearranged H-chain mRNA V-region | — |
| AF002224_at | ubiquitin protein ligase E3A (human papilloma virus E6-associated protein, Angelman syndrome) | UBE3A |
| U21556_at | integral membrane glycoprotein-like | LOC166994 |
| D49372_s_at | chemokine (C-C motif) ligand 11 | CCL11 |
| M38180_rna1_at | hydroxy-delta-5-steroid dehydrogenase, 3 beta- and steroid delta-isomerase 1 | HSD3B1 |
| S71824_at | neural cell adhesion molecule 1 | NCAM1 |
| J03600_at | arachidonate 5-lipoxygenase | ALOX5 |
| D26599_at | proteasome (prosome, macropain) subunit, beta type, 2 | PSMB2 |
| U58091_at | cullin 4B | CUL4B |
| S66541_s_at | growth associated protein 43 | GAP43 |
| S72008_at | septin 7 | 7-Sep |
| M16405_at | cholinergic receptor, muscarinic 4 | CHRM4 |
| U32849_at | N-myc (and STAT) interactor | NMI |
| D31897_at | double C2-like domains, alpha | DOC2A |
| M68519_rna1_at | surfactant, pulmonary-associated protein A2 | SFTPA2 |
| U18383_s_at | nuclear respiratory factor 1 | NRF1 |
| D87012_at | topoisomerase (DNA) III beta | TOP3B |
| U52155_at | potassium inwardly-rectifying channel, subfamily J, member 10 | KCNJ10 |
| D55643_s_at | — | — |
| X94703_at | RAB28, member RAS oncogene family | RAB28 |
| Z27113_at | polymerase (RNA) II (DNA directed) polypeptide F | POLR2F |

FIG. 6B

| Accession | Description | Gene |
|---|---|---|
| X54741_at | cytochrome P450, family 11, subfamily B, polypeptide 2 | CYP11B2 |
| D42138_at | phosphatidylinositol glycan, class B | PIGB |
| U24683_at | immunoglobulin heavy constant mu | IGHM |
| S66793_at | arrestin 3, retinal (X-arrestin) | ARR3 |
| J02888_at | NAD(P)H dehydrogenase, quinone 2 | NQO2 |
| X97302_at | Hypothetical protein MGC11242 | MGC11242 |
| L11672_at | zinc finger protein 91 (HPF7, HTF10) | ZNF91 |
| D50918_at | septin 6 | 6-Sep |
| L24893_s_at | myelin protein zero (Charcot-Marie-Tooth neuropathy 1B) | MPZ |
| HG3859-HT4129_at | --- | --- |
| U60665_at | chromosome 6 open reading frame 10 | C6orf10 |
| M19878_at | calbindin 1, 28kDa | CALB1 |
| Z26256_at | calcium channel, voltage-dependent, L type, alpha 1C subunit | CACNA1C |
| D49677_at | U2(RNU2) small nuclear RNA auxiliary factor 1-like 2 | U2AF1L2 |
| M28827_at | CD1C antigen, c polypeptide | CD1C |
| M96789_at | gap junction protein, alpha 4, 37kDa (connexin 37) | GJA4 |
| U96136_at | catenin (cadherin-associated protein), delta 2 (neural plakophilin-related arm-repeat protein) | CTNND2 |
| M82962_at | meprin A, alpha (PABA peptide hydrolase) | MEP1A |
| U72517_at | Putative protein similar to nessy (Drosophila) | C3F |
| J03507_at | complement component 7 | C7 |
| U68030_at | chemokine (C-C motif) receptor 6 | CCR6 |
| Z14978_at | ARP1 actin-related protein 1 homolog A, centractin alpha (yeast) | ACTR1A |
| U37690_at | polymerase (RNA) II (DNA directed) polypeptide L, 7.6kDa | POLR2L |
| | chorionic gonadotropin, beta polypeptide /// chorionic gonadotropin, beta polypeptide 5 /// chorionic gonadotropin, beta polypeptide 7 /// chorionic gonadotropin, | CGB /// CGB5 /// CGB7 /// CGB8 |
| K03183_f_at | beta polypeptide 8 /// chorionic gonadotropin, beta polypeptide 1 /// chorionic gonadotropin | /// CGB1 /// CGB2 |
| X97671_at | erythropoietin receptor | EPOR |
| HG3412-HT3593_s_at | --- | --- |
| M74290_at | tachykinin receptor 1 | TACR1 |
| HG742-HT742_at | --- | --- |
| L35251_rna1_at | microfibrillar-associated protein 3 | MFAP3 |
| D79993_at | enthoprotin | ENTH |
| X76302_at | putative nucleic acid binding protein RY-1 | RY1 |
| M14539_at | coagulation factor XIII, A1 polypeptide | F13A1 |

FIG. 6C

| | | |
|---|---|---|
| X96584_at | nephroblastoma overexpressed gene | NOV |
| U76992_at | HIV TAT specific factor 1 | HTATSF1 |
| U40391_rna1_at | arylalkylamine N-acetyltransferase | AANAT |
| M90359_at | A kinase (PRKA) anchor protein 5 | AKAP5 |
| Z29074_at | keratin 9 (epidermolytic palmoplantar keratoderma) | KRT9 |
| HG273-HT273_at | | — |
| L40401_at | acyl-CoA thioesterase 2 | ACOT2 |
| U26712_at | Cas-Br-M (murine) ecotropic retroviral transforming sequence b | CBLB |
| X99687_at | Methyl CpG binding protein 2 (Rett syndrome) | MECP2 |
| J05073_at | phosphoglycerate mutase 2 (muscle) | PGAM2 |
| Y07827_s_at | butyrophilin, subfamily 3, member A1 | BTN3A1 |
| L29433_at | coagulation factor X | F10 |
| S78187_at | cell division cycle 25B | CDC25B |
| HG4264-HT4534_s_at | | — |
| X66079_at | Spi-B transcription factor (Spi-1/PU.1 related) | SPIB |
| M62840_at | acyloxyacyl hydrolase (neutrophil) | AOAH |
| X74496_at | prolyl endopeptidase | PREP |
| X56667_at | calbindin 2, 29kDa (calretinin) | CALB2 |
| HG3187-HT3366_s_at | | — |
| L38929_at | protein tyrosine phosphatase, receptor type, D | PTPRD |
| U41068_cds2_s_at | collagen, type XI, alpha 2 | COL11A2 |
| M34715_at | pregnancy specific beta-1-glycoprotein 1 | PSG1 |
| X82240_rna1_at | T-cell leukemia/lymphoma 1A | TCL1A |
| U18088_s_at | phosphodiesterase 4A, cAMP-specific (phosphodiesterase E2 dunce homolog, Drosophila) | PDE4A |
| M91196_at | interferon regulatory factor 8 | IRF8 |
| HG363-HT363_at | | — |
| X70040_at | macrophage stimulating 1 receptor (c-met-related tyrosine kinase) | MST1R |
| X14008_rna1_f_at | lysozyme (renal amyloidosis) | LYZ |
| L10403_at | pro-platelet basic protein-like 2 | PPBPL2 |
| X69115_at | zinc finger protein 37a (KOX 21) | ZNF37A |
| U22322_s_at | fyn-related kinase | FRK |
| K03431_cds1_at | haptoglobin | HP |
| X16666_s_at | homeo box B1 | HOXB1 |

FIG. 6D

| | | |
|---|---|---|
| X83973_at | transcription termination factor, RNA polymerase I | TTF1 |
| D50919_at | tripartite motif-containing 14 | TRIM14 |
| U37408_at | C-terminal binding protein 1 | CTBP1 |
| HG3076-HT3238_s_at | --- | LOC392152 /// LOC442747 |
| L11239_at | similar to gastrulation brain homeobox 1 /// similar to gastrulation brain homeobox 1 | LOC442747 |
| U93091_at | toll-like receptor 4 | TLR4 |
| U86529_at | glutathione transferase zeta 1 (maleylacetoacetate isomerase) | GSTZ1 |
| U72936_s_at | alpha thalassemia/mental retardation syndrome X-linked (RAD54 homolog, S. cerevisiae) | ATRX |
| HG1153-HT1153_at | --- | --- |
| L05187_at | small proline-rich protein 1A | SPRR1A |
| HG3962-HT4232_at | --- | --- |
| AFFX-ThrX-3_at | --- | --- |
| M20786_at | serpin peptidase inhibitor, clade F (alpha-2 antiplasmin, pigment epithelium derived factor), member 2 | SERPINF2 |
| U32576_ma1_at | apolipoprotein C-IV | APOC4 |
| U72508_at | B7 gene | B7 |
| U01691_s_at | annexin A5 | ANXA5 |
| L12711_s_at | transketolase (Wernicke-Korsakoff syndrome) | TKT |
| S72024_s_at | eukaryotic translation initiation factor 5A (eIF-5A) (eIF-4D) (Rev-binding factor) /// similar to Eukaryotic translation initiation factor 5A (eIF-5A) (eIF-4D) (Rev-binding factor) | EIF5A /// LOC143243 /// LOC143244 |
| U05227_at | RAB40B, member RAS oncogene family | RAB40B |
| X53002_s_at | integrin, beta 5 | ITGB5 |
| U46006_s_at | cysteine and glycine-rich protein 2 | CSRP2 |
| U83239_s_at | chemokine (C-C motif) ligand 22 | CCL22 |
| U50523_at | actin related protein 2/3 complex, subunit 2, 34kDa | ARPC2 |
| HG2917-HT3061_f_at | --- | --- |
| U91932_at | adaptor-related protein complex 3, sigma 1 subunit | AP3S1 |
| U68063_at | splicing factor, arginine/serine-rich 10 (transformer 2 homolog, Drosophila) | SFRS10 |
| X67951_at | peroxiredoxin 1 | PRDX1 |
| U45973_at | skeletal muscle and kidney enriched inositol phosphatase | SKIP |
| L43631_at | scaffold attachment factor B | SAFB |
| S75463_at | Tu translation elongation factor, mitochondrial | TUFM |

FIG. 6E

| ID | Description | Symbol |
|---|---|---|
| D28473_s_at | isoleucine-tRNA synthetase | IARS |
| M27749_r_at | immunoglobulin lambda-like polypeptide 1 | IGLL1 |
| L13943_at | glycerol kinase | GK |
| D13315_at | glyoxalase I | GLO1 |
| D86956_at | heat shock 105kDa/110kDa protein 1 | HSPH1 |
| U81556_at | CTD (carboxy-terminal domain, RNA polymerase II, polypeptide A) small phosphatase 2 | CTDSP2 |
| AB000409_at | MAP kinase interacting serine/threonine kinase 1 | MKNK1 |
| L20010_at | host cell factor C1 (VP16-accessory protein) | HCFC1 |
| D38449_at | putative G protein coupled receptor | GPR |
| M94630_at | heterogeneous nuclear ribonucleoprotein D (AU-rich element RNA binding protein 1, 37kDa) | HNRPD |
| U59748_at | desert hedgehog homolog (Drosophila) | DHH |
| X15217_at | SKI-like | SKIL |
| Z26653_at | laminin, alpha 2 (merosin, congenital muscular dystrophy) | LAMA2 |
| U76764_s_at | CD97 antigen | CD97 |
| U11292_at | proteasome (prosome, macropain) activator subunit 3 (PA28 gamma; Ki) | PSME3 |
| X99268_at | twist homolog 1 (acrocephalosyndactyly 3; Saethre-Chotzen syndrome) (Drosophila) | TWIST1 |
| U09877_at | superkiller viralicidic activity 2-like (S. cerevisiae) | SKIV2L |
| X64877_at | complement factor H-related 2 | CFHL2 |
| X14445_at | fibroblast growth factor 3 (murine mammary tumor virus integration site (v-int-2) oncogene homolog) | FGF3 |
| X82324_at | POU domain, class 3, transcription factor 4 | POU3F4 |
| D38305_at | transducer of ERBB2, 1 | TOB1 |
| L77730_at | adenosine A3 receptor | ADORA3 |
| M14200_rna1_at | diazepam binding inhibitor (GABA receptor modulator, acyl-Coenzyme A binding protein) | DBI |
| S80343_at | arginyl-tRNA synthetase | RARS |
| U97188_at | IGF-II mRNA-binding protein 3 | IMP-3 |
| S39329_at | kallikrein 2, prostatic | KLK2 |
| L07033_at | 3-hydroxymethyl-3-methylglutaryl-Coenzyme A lyase (hydroxymethylglutaricaciduria) | HMGCL |
| D42045_at | DNA cross-link repair 1A (PSO2 homolog, S. cerevisiae) | DCLRE1A |
| U95006_at | stimulated by retinoic acid 13 homolog (mouse) | STRA13 |
| X98176_at | caspase 8, apoptosis-related cysteine peptidase | CASP8 |
| U63090_at | ST3 beta-galactoside alpha-2,3-sialyltransferase 2 | ST3GAL2 |
| HG1869-HT1904_at | --- | --- |
| L16862_at | G protein-coupled receptor kinase 6 | GRK6 |

FIG. 6F

| | | |
|---|---|---|
| U07349_at | mitogen-activated protein kinase kinase kinase 2 | MAP4K2 |
| X12447_at | aldolase A, fructose-bisphosphate | ALDOA |
| D13627_at | chaperonin containing TCP1, subunit 8 (theta) | CCT8 |
| D80003_at | nuclear receptor coactivator 6 | NCOA6 |
| D30655_at | eukaryotic translation initiation factor 4A, isoform 2 | EIF4A2 |
| X06323_at | mitochondrial ribosomal protein L3 | MRPL3 |
| S46622_at | protein phosphatase 3 (formerly 2B), catalytic subunit, gamma isoform (calcineurin A gamma) | PPP3CC |
| D50405_at | histone deacetylase 1 | HDAC1 |
| D00596_at | thymidylate synthetase | TYMS |
| HG1996-HT2044_at | | — |
| L08485_at | gamma-aminobutyric acid (GABA) A receptor, alpha 5 | GABRA5 |
| U31248_at | zinc finger protein 174 | ZNF174 |
| U51432_at | SNW domain containing 1 | SNW1 |
| Y00796_at | integrin, alpha L (antigen CD11A (p180), lymphocyte function-associated antigen 1; alpha polypeptide) | ITGAL |
| U06643_s_at | lectin, galactoside-binding, soluble, 7 (galectin 7) | LGALS7 |
| L15189_s_at | heat shock 70kDa protein 9B (mortalin-2) | HSPA9B |
| J04760_at | troponin I type 1 (skeletal, slow) | TNNI1 |
| M75106_at | carboxypeptidase B2 (plasma, carboxypeptidase U) | CPB2 |
| HG3255-HT3432_at | | — |
| M95929_at | sideroflexin 3 | SFXN3 |
| D31846_at | aquaporin 2 (collecting duct) | AQP2 |
| HG3578-HT3781_at | | — |
| D63475_at | adaptor-related protein complex 2, mu 1 subunit | AP2M1 |
| M59830_at | heat shock 70kDa protein 1B | HSPA1B |
| Z70219_at | jumonji domain containing 2A | JMJD2A |
| L33799_at | procollagen C-endopeptidase enhancer | PCOLCE |
| AFFX-HUMGAPDH/M33197_3_at | glyceraldehyde-3-phosphate dehydrogenase | GAPDH |
| L34075_at | FK506 binding protein 12-rapamycin associated protein 1 | FRAP1 |
| M28213_s_at | RAB2, member RAS oncogene family | RAB2 |
| X16416_at | v-abl Abelson murine leukemia viral oncogene homolog 1 | ABL1 |
| M92439_at | leucine-rich PPR-motif containing | LRPPRC |

FIG. 6G

| | | |
|---|---|---|
| X75756_at | protein kinase D1 | PRKD1 |
| U69141_at | glutaryl-Coenzyme A dehydrogenase | GCDH |
| L27213_s_at | solute carrier family 4, anion exchanger, member 3 | SLC4A3 |
| X57129_at | histone 1, H1c | HIST1H1C |
| X81882_at | cullin 5 | CUL5 |
| Z33642_at | immunoglobulin superfamily, member 2 | IGSF2 |
| M27492_at | interleukin 1 receptor, type I | IL1R1 |
| U89916_at | claudin 10 | CLDN10 |
| D85423_at | CDC5 cell division cycle 5-like (S. pombe) | CDC5L |
| U90547_at | tripartite motif-containing 38 | TRIM38 |
| M54914_s_at | follicle stimulating hormone, beta polypeptide | FSHB |
| S62696_s_at | complement component (3d/Epstein Barr virus) receptor 2 | CR2 |
| D17461_at | --- | --- |
| D13897_rna2_at | peptide YY | PYY |
| Z35278_at | runt-related transcription factor 3 | RUNX3 |
| J03161_at | serum response factor (c-fos serum response element-binding transcription factor) | SRF |
| HG4169-HT4439_s_at | --- | --- |
| D63879_at | squamous cell carcinoma antigen recognised by T cells 3 | SART3 |
| AB000467_at | chromosome 4 open reading frame 9 | C4orf9 |
| U28811_at | golgi apparatus protein 1 | GLG1 |
| HG4116-HT4386_s_at | --- | --- |
| X89430_at | methyl CpG binding protein 2 (Rett syndrome) | MECP2 |
| D12625_at | neurofibromin 1 (neurofibromatosis, von Recklinghausen disease, Watson disease) | NF1 |
| D13631_s_at | Rac/Cdc42 guanine nucleotide exchange factor (GEF) 6 | ARHGEF6 |
| X71129_at | electron-transfer-flavoprotein, beta polypeptide | ETFB |
| Z49254_at | mitochondrial ribosomal protein L23 | MRPL23 |
| U79734_at | huntingtin interacting protein 1 | HIP1 |
| U25789_at | ribosomal protein L21 | RPL21 |
| X52947_at | gap junction protein, alpha 1, 43kDa (connexin 43) | GJA1 |
| HG4417-HT4687_f_at | --- | --- |
| U40371_at | phosphodiesterase 1C, calmodulin-dependent 70kDa | PDE1C |
| AFFX-HUMISGF3A/M97935_MA_at | signal transducer and activator of transcription 1, 91kDa | STAT1 |
| Z83802_at | dynein, axonemal, heavy polypeptide 12 | DNAH12 |

FIG. 6H

| Probe ID | Description | Gene |
|---|---|---|
| L21893_at | solute carrier family 10 (sodium/bile acid cotransporter family), member 1 | SLC10A1 |
| Z84483_at | klotho | KL |
| X83535_s_at | matrix metallopeptidase 14 (membrane-inserted) | MMP14 |
| M73548_at | adenomatosis polyposis coli | APC |
| X64037_at | general transcription factor IIF, polypeptide 1, 74kDa | GTF2F1 |
| HG1595-HT4788_s_at | --- | --- |
| U90552_s_at | butyrophilin, subfamily 3, member A3 /// butyrophilin, subfamily 3, member A2 /// butyrophilin, subfamily 3, member A1 | BTN3A3 /// BTN3A2 /// BTN3A1 |
| S78432_xpt1_at | --- | --- |
| D63851_at | syntaxin binding protein 1 | STXBP1 |
| HG651-HT4201_at | --- | --- |
| U15782_at | cleavage stimulation factor, 3' pre-RNA, subunit 3, 77kDa | CSTF3 |
| U57094_at | RAB27A, member RAS oncogene family | RAB27A |
| M31932_at | Fc fragment of IgG, low affinity IIa, receptor (CD32) | FCGR2A |
| U92971_at | coagulation factor II (thrombin) receptor-like 2 | F2RL2 |
| U51711_at | desmocollin 2 | DSC2 |
| D78012_at | collapsin response mediator protein 1 | CRMP1 |
| L07515_at | chromobox homolog 5 (HP1 alpha homolog, Drosophila) | CBX5 |
| L24774_s_at | dodecenoyl-Coenzyme A delta isomerase (3,2 trans-enoyl-Coenzyme A isomerase) | DCI |
| X54232_at | glypican 1 | GPC1 |
| X86428_s_at | protein phosphatase 2A, regulatory subunit B' (PR 53) | PPP2R4 |
| S71043_rna1_s_at | immunoglobulin heavy constant alpha 1 /// immunoglobulin heavy constant alpha 2 (A2m marker) /// hypothetical protein MGC27165 | IGHA1 /// IGHA2 /// MGC27165 |
| M29932_s_at | adrenergic, beta-3-, receptor | ADRB3 |
| Z47553_at | flavin containing monooxygenase 5 | FMO5 |
| U45982_at | chemokine (C-C motif) receptor 9 | CCR9 |
| X90857_at | chromosome 16 open reading frame 35 | C16orf35 |
| M31667_f_at | cytochrome P450, family 1, subfamily A, polypeptide 2 | CYP1A2 |
| J05068_at | transcobalamin I (vitamin B12 binding protein, R binder family) | TCN1 |
| U12779_at | mitogen-activated protein kinase-activated protein kinase 2 | MAPKAPK2 |
| X54667_s_at | cystatin SN /// cystatin S | CST1 /// CST4 |
| Y07829_xpt3_at | tripartite motif-containing 40 | TRIM40 |
| U48697_at | RAP1A, member of RAS oncogene family | RAP1A |

FIG. 6I

| | | |
|---|---|---|
| J03934_s_at | NAD(P)H dehydrogenase, quinone 1 | NQO1 |
| D38537_s_at | protoporphyrinogen oxidase | PPOX |
| J00287_at | pepsinogen 5, group I (pepsinogen A) | PGA5 |
| X81892_at | G protein-coupled receptor 64 | GPR64 |
| M98539_at | prostaglandin D2 synthase 21kDa (brain) | PTGDS |
| M69238_at | aryl hydrocarbon receptor nuclear translocator | ARNT |
| D97120_at | family with sequence similarity 3, member C | FAM3C |
| U66711_rna1_s_at | lymphocyte antigen 6 complex, locus E | LY6E |
| M96956_at | teratocarcinoma-derived growth factor 1 | TDGF1 |
| M83088_at | phosphoglucomutase 1 | PGM1 |
| J03592_at | solute carrier family 25 (mitochondrial carrier; adenine nucleotide translocator), member 6 | SLC25A6 |
| D88795_at | protocadherin beta 11 | PCDHB11 |
| U67934_at | RNA pseudouridylate synthase domain containing 2 | RPUSD2 |
| M77144_rna1_at | hydroxy-delta-5-steroid dehydrogenase, 3 beta- and steroid delta-isomerase 2 | HSD3B2 |
| M18185_at | gastric inhibitory polypeptide | GIP |
| U83843_at | chaperonin containing TCP1, subunit 7 (eta) | CCT7 |
| U58048_at | procollagen (type III) N-endopeptidase | PCOLN3 |
| X79353_at | GDP dissociation inhibitor 1 | GDI1 |
| U88726_at | symplekin | SYMPK |
| M84739_at | calreticulin | CALR |
| X55990_rna1_at | ribonuclease, RNase A family, 3 (eosinophil cationic protein) | RNASE3 |
| U58090_at | cullin 4A | CUL4A |
| D37931_at | ribonuclease, RNase A family, 4 | RNASE4 |
| X05360_at | cell division cycle 2, G1 to S and G2 to M | CDC2 |
| U79280_at | cold shock domain containing C2, RNA binding | CSDC2 |
| AC000062_at | hypothetical protein CG003 | 13CDNA73 |
| X66114_rna1_at | solute carrier family 25 (mitochondrial carrier; oxoglutarate carrier), member 11 | SLC25A11 |
| L27479_at | chromosome 9 open reading frame 61 | C9orf61 |
| D50931_at | KIAA0141 | KIAA0141 |
| J05036_s_at | cathepsin E | CTSE |
| L00352_at | low density lipoprotein receptor (familial hypercholesterolemia) | LDLR |
| L05072_s_at | interferon regulatory factor 1 | IRF1 |
| Z47727_at | polymerase (RNA) II (DNA directed) polypeptide K, 7.0kDa | POLR2K |

FIG. 6J

| | | |
|---|---|---|
| S78234_at | cell division cycle 27 | CDC27 |
| X05309_at | complement component (3b/4b) receptor 1, including Knops blood group system | CR1 |
| X76104_at | death-associated protein kinase 1 | DAPK1 |
| U06233_at | POU domain, class 4, transcription factor 2 | POU4F2 |
| X70297_at | cholinergic receptor, nicotinic, alpha polypeptide 7 /// CHRNA7 (cholinergic receptor, nicotinic, alpha polypeptide 7, exons 5-10) and FAM7A (family with sequence similarity 7A, exons A-E) fusion | CHRNA7 /// CHRFAM7A |
| U90065_s_at | potassium channel, subfamily K, member 1 | KCNK1 |
| U51095_at | caudal type homeo box transcription factor 1 | CDX1 |
| M37435_at | colony stimulating factor 1 (macrophage) | CSF1 |
| X12556_at | MCF.2 cell line derived transforming sequence | MCF2 |
| U20158_at | lymphocyte cytosolic protein 2 (SH2 domain containing leukocyte protein of 76kDa) | LCP2 |
| U38276_at | sema domain, immunoglobulin domain (Ig), short basic domain, secreted, (semaphorin) 3F | SEMA3F |
| HG4433-HT4703_at | — | — |
| J05037_at | serine dehydratase | SDS |
| U49974_f_at | — | — |
| X16866_at | cytochrome P450, family 2, subfamily D, polypeptide 6 | CYP2D6 |
| Z29077_xpt1_at | cell division cycle 25C | CDC25C |
| HG4606-HT5011_at | — | — |
| D42044_at | KIAA0090 | KIAA0090 |
| X06318_at | Protein kinase C, beta 1 | PRKCB1 |
| X15376_at | gamma-aminobutyric acid (GABA) A receptor, gamma 2 | GABRG2 |
| L25441_at | protein geranylgeranyltransferase type I, beta subunit | PGGT1B |
| M63582_at | thyrotropin-releasing hormone | TRH |
| M62843_at | ELAV (embryonic lethal, abnormal vision, Drosophila)-like 4 (Hu antigen D) | ELAVL4 |
| M77016_at | tropomodulin 1 | TMOD1 |
| U03494_at | transcription factor CP2 | TFCP2 |
| X06661_at | calbindin 1, 28kDa | CALB1 |
| D86331_s_at | matrix metallopeptidase 15 (membrane-inserted) | MMP15 |
| X03072_at | wingless-type MMTV integration site family, member 1 | WNT1 |
| Y00477_at | elastase 2, neutrophil | ELA2 |
| M21388_at | immunoglobulin heavy constant delta /// immunoglobulin heavy constant gamma 1 (G1m marker) /// immunoglobulin heavy constant mu /// hypothetical protein MGC27165 | IGHD /// IGHG1 /// IGHM /// MGC27165 |

FIG. 6K

| | | |
|---|---|---|
| L13852_at | ubiquitin-activating enzyme E1-like | UBE1L |
| U24153_at | p21 (CDKN1A)-activated kinase 2 | PAK2 |
| D38251_s_at | polymerase (RNA) II (DNA directed) polypeptide E, 25kDa | POLR2E |
| D83785_at | mastermind-like 1 (Drosophila) | MAML1 |
| D55638_at | B-cell PABL (pseudoautosomal boundary-like sequence) mRNA, clone Bc4 | --- |
| X16105_at | RD RNA binding protein | RDBP |
| HG3319-HT3496_s_at | | --- |
| M11567_rna1_at | angiogenin, ribonuclease, RNase A family, 5 /// ribonuclease, RNase A family, 4 | ANG /// RNASE4 |
| X93017_at | solute carrier family 8 (sodium-calcium exchanger), member 3 | SLC8A3 |
| L19314_at | hairy and enhancer of split 1, (Drosophila) | HES1 |
| U52518_at | GRB2-related adaptor protein | GRAP |
| M64554_rna1_at | coagulation factor XIII, B polypeptide | F13B |
| S81893_at | | --- |
| M21389_at | keratin 5 (epidermolysis bullosa simplex, Dowling-Meara/Kobner/Weber-Cockayne types) | KRT5 |
| M24594_at | interferon-induced protein with tetratricopeptide repeats 1 | IFIT1 |
| U00957_at | A kinase (PRKA) anchor protein 10 | AKAP10 |
| AFFX-ThrX-M_at | | --- |
| D00762_at | proteasome (prosome, macropain) subunit, alpha type, 3 | PSMA3 |
| U66669_at | 3-hydroxyisobutyryl-Coenzyme A hydrolase | HIBCH |
| U73738_at | calcium/calmodulin-dependent protein kinase (CaM kinase) II delta | CAMK2D |
| J03171_at | interferon (alpha, beta and omega) receptor 1 | IFNAR1 |
| D88613_at | glial cells missing homolog 1 (Drosophila) | GCM1 |
| S79267_at | CD4 antigen (p55) | CD4 |
| U64871_at | G protein-coupled receptor 19 | GPR19 |
| S66427_at | AT rich interactive domain 4A (RBP1-like) | ARID4A |
| L39064_rna1_at | interleukin 9 receptor /// similar to interleukin 9 receptor | IL9R /// LOC400481 |
| U52969_at | Purkinje cell protein 4 | PCP4 |
| HG270-HT270_at | | --- |
| L00190_s_at | serpin peptidase inhibitor, clade C (antithrombin), member 1 | SERPINC1 |
| Y10205_at | Leucine rich repeat containing 16 | LRRC16 |
| X55889_at | ciliary neurotrophic factor /// zinc finger protein 91 homolog (mouse) | CNTF /// ZFP91 |
| L38487_at | estrogen-related receptor alpha | ESRRA |
| U33841_at | ataxia telangiectasia mutated (includes complementation groups A, C and D) | ATM |

FIG. 6L

| Probe ID | Description | Gene |
|---|---|---|
| M34455_at | indoleamine-pyrrole 2,3 dioxygenase | INDO |
| L10378_at | THAP domain containing 11 | THAP11 |
| M77829_s_at | aquaporin 1 (channel-forming integral protein, 28kDa) | AQP1 |
| U37426_at | kinesin family member 11 | KIF11 |
| U18914_at | tumor protein D52 | TPD52 |
| M37457_at | ATPase, Na+/K+ transporting, alpha 3 polypeptide | ATP1A3 |
| U48865_s_at | CCAAT/enhancer binding protein (C/EBP), epsilon | CEBPE |
| X86570_at | keratin, hair, acidic, 1 | KRTHA1 |
| D85939_at | craniofacial development protein 1 | CFDP1 |
| X95404_at | cofilin 1 (non-muscle) | CFL1 |
| M27749_at | immunoglobulin lambda-like polypeptide 1 /// similar to bK246H3.1 (immunoglobulin lambda-like polypeptide 1, pre-B-cell specific) /// similar to omega protein | IGLL1 /// LOC91316 /// LOC91353 |
| L24783_at | replication factor C (activator 1) 1, 145kDa | RFC1 |
| U18985_at | triadin | TRDN |
| K03460_at | tubulin, alpha 2 /// similar to alpha tubulin /// alpha-tubulin isotype H2-alpha | TUBA2 /// LOC112714 /// H2-ALPHA |
| Z72499_at | ubiquitin specific peptidase 7 (herpes virus-associated) | USP7 |
| L27841_at | pericentriolar material 1 | PCM1 |
| D63998_at | mannosidase, alpha, class 2A, member 1 | MAN2A1 |
| U40572_at | syntrophin, beta 2 (dystrophin-associated protein A1, 59kDa, basic component 2) | SNTB2 |
| U83246_at | copine I | CPNE1 |
| D89859_at | zinc finger protein 161 homolog (mouse) | ZFP161 |
| U49188_at | tumor differentially expressed 1 | TDE1 |
| M61764_at | tubulin, gamma 1 | TUBG1 |
| U80226_s_at | 4-aminobutyrate aminotransferase | ABAT |
| M89796_rna1_at | membrane-spanning 4-domains, subfamily A, member 2 (Fc fragment of IgE, high affinity I, receptor for; beta polypeptide) | MS4A2 |
| X89894_at | nuclear receptor subfamily 4, group A, member 3 | NR4A3 |
| HG4740-HT5187_at | — | — |
| U45448_s_at | purinergic receptor P2X, ligand-gated ion channel, 1 | P2RX1 |
| M37815_cds1_at | CD28 antigen (Tp44) | CD28 |
| U85267_at | Down syndrome critical region gene 1 | DSCR1 |

FIG. 6M

| | | |
|---|---|---|
| X91117_rna1_at | solute carrier family 6 (neurotransmitter transporter, noradrenalin), member 2 | SLC6A2 |
| X76105_at | death-associated protein | DAP |
| U43916_s_at | epithelial membrane protein 1 | EMP1 |
| D87464_at | KIAA0274 | KIAA0274 |
| U57057_at | coronin, actin binding protein, 2A | CORO2A |
| U57450_at | serpin peptidase inhibitor, clade F (alpha-2 antiplasmin, pigment epithelium derived factor), member 1 | SERPINF1 |
| X94563_xpt2_r_at | diazepam binding inhibitor (GABA receptor modulator, acyl-Coenzyme A binding protein) | DBI |
| U63312_at | — | — |
| X97303_at | zinc finger, matrin type 2 | ZMAT2 |
| D21205_at | tripartite motif-containing 25 | TRIM25 |
| X99393_s_at | chemokine (C-C motif) receptor 5 | CCR5 |
| X60484_at | histone 1, H4k /// histone 1, H4j | HIST1H4K /// HIST1H4J |
| X82200_at | tripartite motif-containing 22 | TRIM22 |
| U14910_at | retinal G protein coupled receptor | RGR |
| HG1733-HT1748_at | — | — |
| U00802_s_at | drebrin 1 | DBN1 |
| U19180_at | B melanoma antigen | BAGE |
| U62966_at | solute carrier family 28 (sodium-coupled nucleoside transporter), member 1 | SLC28A1 |
| J04111_at | v-jun sarcoma virus 17 oncogene homolog (avian) | JUN |
| X63717_at | Fas (TNF receptor superfamily, member 6) | FAS |
| X78686_at | chemokine (C-X-C motif) ligand 5 | CXCL5 |
| J05614_at | proliferating cell nuclear antigen | PCNA |
| U03642_at | angiotensin II receptor-like 1 | AGTRL1 |
| M37075_at | myosin, light polypeptide 4, alkali, atrial, embryonic | MYL4 |
| L20320_at | cyclin-dependent kinase 7 (MO15 homolog, Xenopus laevis, cdk-activating kinase) | CDK7 |
| U16812_s_at | BCL2-antagonist/killer 1 | BAK1 |
| L11066_at | heat shock 70kDa protein 9B (mortalin-2) | HSPA9B |
| D90042_at | N-acetyltransferase 2 (arylamine N-acetyltransferase) | NAT2 |
| HG1828-HT1857_at | — | — |
| U79718_at | nth endonuclease III-like 1 (E. coli) | NTHL1 |
| M87860_at | lectin, galactoside-binding, soluble, 2 (galectin 2) | LGALS2 |
| M37457_s_at | ATPase, Na+/K+ transporting, alpha 3 polypeptide | ATP1A3 |

FIG. 6N

| Accession | Description | Gene |
|---|---|---|
| U43522_at | PTK2B protein tyrosine kinase 2 beta | PTK2B |
| D86983_at | peroxidasin homolog (Drosophila) | PXDN |
| M29551_at | protein phosphatase 3 (formerly 2B), catalytic subunit, beta isoform (calcineurin A beta) | PPP3CB |
| U20758_ma1_at | secreted phosphoprotein 1 (osteopontin, bone sialoprotein I, early T-lymphocyte activation 1) | SPP1 |
| X77584_at | thioredoxin | TXN |
| U61262_at | neogenin homolog 1 (chicken) | NEO1 |
| J03925_at | integrin, alpha M (complement component receptor 3, alpha; also known as CD11b (p170), macrophage antigen alpha polypeptide) | ITGAM |
| L25851_at | integrin, alpha E (antigen CD103, human mucosal lymphocyte antigen 1; alpha polypeptide) | ITGAE |
| M34041_at | adrenergic, alpha-2B-, receptor | ADRA2B |
| U33838_at | v-rel reticuloendotheliosis viral oncogene homolog A, nuclear factor of kappa light polypeptide gene enhancer in B-cells 3, p65 (avian) | RELA |
| L40392_at | RNA binding motif protein 25 | RBM25 |
| U26424_at | serine/threonine kinase 3 (STE20 homolog, yeast) | STK3 |
| U75968_at | DEAD/H (Asp-Glu-Ala-Asp/His) box polypeptide 11 (CHL1-like helicase homolog, S. cerevisiae) | DDX11 |
| X71125_at | glutaminyl-peptide cyclotransferase (glutaminyl cyclase) | QPCT |
| Y07847_at | RAS-related on chromosome 22 | RRP22 |
| U83117_at | SMT3 suppressor of mif two 3 homolog 1 (yeast) | SUMO1 |
| D79983_at | ring finger protein 144 | RNF144 |
| M68874_at | phospholipase A2, group IVA (cytosolic, calcium-dependent) | PLA2G4A |
| L40027_at | glycogen synthase kinase 3 alpha | GSK3A |
| Z71389_at | defensin, beta 4 | DEFB4 |
| X15729_s_at | DEAD (Asp-Glu-Ala-Asp) box polypeptide 5 | DDX5 |
| L35475_at | olfactory receptor, family 2, subfamily H, member 1 | OR2H1 |
| Z49878_at | guanidinoacetate N-methyltransferase | GAMT |
| U73328_at | distal-less homeobox 4 | DLX4 |
| X04688_at | interleukin 5 (colony-stimulating factor, eosinophil) | IL5 |
| X99140_at | keratin, hair, basic, 5 | KRTHB5 |
| Z14000_at | ring finger protein 1 | RING1 |
| D23662_at | neural precursor cell expressed, developmentally down-regulated 8 | NEDD8 |
| M29927_at | ornithine aminotransferase (gyrate atrophy) | OAT |
| L15388_at | G protein-coupled receptor kinase 5 | GRK5 |
| X13451_s_at | CD79A antigen (immunoglobulin-associated alpha) | CD79A |

FIG. 60

| | | |
|---|---|---|
| HG1428-HT1428_s_at | — | — |
| S52028_s_at | cystathionase (cystathionine gamma-lyase) | CTH |
| L37043_at | casein kinase 1, epsilon | CSNK1E |
| U20980_at | chromatin assembly factor 1, subunit B (p60) | CHAF1B |
| U33838_s_at | v-rel reticuloendotheliosis viral oncogene homolog A, nuclear factor of kappa light polypeptide gene enhancer in B-cells 3, p65 (avian) | RELA |
| U82613_at | transient receptor potential cation channel, subfamily V, member 6 | TRPV6 |
| D80012_at | Ubiquitin specific peptidase 10 | USP10 |
| J04611_at | X-ray repair complementing defective repair in Chinese hamster cells 6 (Ku autoantigen, 70kDa) | XRCC6 |
| S73149_at | — | — |
| L13977_at | prolylcarboxypeptidase (angiotensinase C) | PRCP |
| D25539_at | KIAA0040 | KIAA0040 |
| U67674_at | solute carrier family 10 (sodium/bile acid cotransporter family), member 2 | SLC10A2 |
| U52111_rna3_at | ATP-binding cassette, sub-family D (ALD), member 1 | ABCD1 |
| | androgen receptor (dihydrotestosterone receptor; testicular feminization; | |
| M23263_at | spinal and bulbar muscular atrophy; Kennedy disease) | AR |
| Z14244_at | cytochrome c oxidase subunit VIIb | COX7B |
| Z37976_at | latent transforming growth factor beta binding protein 2 | LTBP2 |
| M64929_at | protein phosphatase 2 (formerly 2A), regulatory subunit B (PR 52), alpha isoform | PPP2R2A |
| U80457_at | single-minded homolog 2 (Drosophila) | SIM2 |
| M55131_at | cystic fibrosis transmembrane conductance regulator, ATP-binding cassette (sub-family C, member 7) | CFTR |
| X74874_rna1_s_at | polymerase (RNA) II (DNA directed) polypeptide A, 220kDa | POLR2A |
| D80005_at | chromosome 9 open reading frame 10 | C9orf10 |
| X97160_rna1_at | transcription factor binding to IGHM enhancer 3 | TFE3 |
| U97502_rna1_at | butyrophilin, subfamily 3, member A2 | BTN3A2 |
| S73840_at | myosin, heavy polypeptide 2, skeletal muscle, adult | MYH2 |
| M90354_at | — | — |
| X73113_at | myosin binding protein C, fast type | MYBPC2 |
| D89050_at | oxidised low density lipoprotein (lectin-like) receptor 1 | OLR1 |
| D10523_at | oxoglutarate (alpha-ketoglutarate) dehydrogenase (lipoamide) | OGDH |
| U01923_at | heterogeneous nuclear ribonucleoprotein H2 (H') | HNRPH2 |
| U19517_at | lipoprotein, Lp(a)-like 2 | LPAL2 |
| J02923_at | lymphocyte cytosolic protein 1 (L-plastin) | LCP1 |
| D42038_at | KIAA0087 gene product | KIAA0087 |

FIG. 6P

| | | |
|---|---|---|
| HG4462-HT4731_at | — | — |
| U55764_at | sulfotransferase family 1E, estrogen-preferring, member 1 | SULT1E1 |
| L14269_at | solute carrier family 18 (vesicular monoamine), member 2 | SLC18A2 |
| M21985_at | nuclear receptor subfamily 2, group C, member 1 | NR2C1 |
| L12350_at | thrombospondin 2 | THBS2 |
| M80482_at | proprotein convertase subtilisin/kexin type 6 | PCSK6 |
| M91670_at | ubiquitin-conjugating enzyme E2S | UBE2S |
| D32202_at | adrenergic, alpha-1A-, receptor | ADRA1A |
| X78678_at | ketohexokinase (fructokinase) | KHK |
| U19247_ma1_s_at | interferon gamma receptor 1 | IFNGR1 |
| K03474_at | anti-Mullerian hormone | AMH |
| M80563_at | S100 calcium binding protein A4 (calcium protein, calvasculin, metastasin, murine placental homolog) | S100A4 |
| L20298_at | core-binding factor, beta subunit | CBFB |
| M84349_at | CD59 antigen p18-20 (antigen identified by monoclonal antibodies 16.3A5, EJ16, EJ30, EL32 and G344) | CD59 |
| K02882_cds1_s_at | immunoglobulin heavy constant delta | IGHD |
| J05213_at | integrin-binding sialoprotein (bone sialoprotein, bone sialoprotein II) | IBSP |
| X66171_at | CD300C antigen | CD300C |
| U30930_at | UDP glycosyltransferase 8 (UDP-galactose ceramide galactosyltransferase) | UGT8 |
| M91083_at | Ras association (RalGDS/AF-6) domain family 7 | RASSF7 |
| D50928_at | scaffold attachment factor B2 | SAFB2 |
| AB000450_at | vaccinia related kinase 2 | VRK2 |
| AJ001487_at | — | — |
| D38081_at | thromboxane A2 receptor | TBXA2R |
| AC002086_at | zinc finger and BTB domain containing 33 | ZBTB33 |
| D29677_at | helicase with zinc finger | HELZ |

Control Genes

| NCBI RefSeq Acc No. | LocusLink Gene Name |
|---|---|
| NM_021009.4 | ubiquitin C, Gene hCG1744180 Celera Annotation |
| NM_000190.3 | hydroxymethylbilane synthase, Gene hCG39398 Celera Annotation |
| NM_003406.2 | tyrosine 3-monooxygenase/tryptophan 5-monooxygenase activation protein, zeta polypeptide, Gene hCG2009146 Celera Annotation |
| NM_000937.2 | polymerase (RNA) II (DNA directed) polypeptide A, 220kDa, Gene hCG42013 Celera Annotation |
| NM_006390.2 | importin 8, Gene hCG37269 Celera Annotation |
| NM_000194.1 | hypoxanthine phosphoribosyltransferase 1 (Lesch-Nyhan syndrome), Gene hCG15412 Celera Annotation |
| NM_053275.3, NM_001002.3 | ribosomal protein, large, P0, Gene hCG2016152 Celera Annotation |
| NM_021130.3 | peptidylprolyl isomerase A (cyclophilin A), Gene hCG2014648 Celera Annotation |
| NM_001101.2 | actin, beta, Gene hCG15971 Celera Annotation |
| NM_000181.2 | glucuronidase, beta, Gene hCG18478 Celera Annotation |
| NM_004048.2 | beta-2-microglobulin, Gene hCG1786707 Celera Annotation |
| NM_000291.2 | phosphoglycerate kinase 1, Gene hCG20034 Celera Annotation |
| NM_002046.3 | glyceraldehyde-3-phosphate dehydrogenase, Gene hCG2005673 Celera Annotation |
| NM_003234.1 | transferrin receptor (p90, CD71), Gene hCG22086 Celera Annotation |
| NM_003194.3 | TATA box binding protein, Gene hCG2029691 Celera Annotation |
| NM_004168.2 | subunit A gene of the succinate dehydrogenase complex |
|  | 18s ribosomal RNA |

FIG. 7

GENE SIGNATURE FOR THE PREDICTION OF RADIATION THERAPY RESPONSE

CLAIM OF PRIORITY

This application is a continuation of U.S. patent application Ser. No. 12/210,135, filed on Sep. 12, 2008, which claims the benefit of U.S. Provisional Patent Application Ser. No. 60/972,544, filed on Sep. 14, 2007, and is a continuation in part of U.S. patent application Ser. No. 12/053,796, filed on Mar. 24, 2008, which claims the benefit of U.S. Provisional Patent Application Ser. No. 60/896,550, filed on Mar. 23, 2007, and U.S. Provisional Patent Application Ser. No. 60/896,350, filed on Mar. 22, 2007. The entire contents of the foregoing are hereby incorporated by reference.

FEDERALLY SPONSORED RESEARCH OR DEVELOPMENT

This invention was made with Government support under Grant No. 5 K08 CA108926-03, NCI Grant R21CA101355, Department of Defense, National Functional Genomics Center—DAMD 17-02-2-0051. The Government has certain rights in the invention.

TECHNICAL FIELD

This invention relates to mathematical models and methods for predicting tumor sensitivity to radiation therapy using biological assay data, which can be used, e.g., for selecting a treatment for a subject who has a tumor.

BACKGROUND

Personalized medicine holds the promise that the diagnosis, prevention and treatment of cancer will be based on individual assessment of risk (Dalton and Friend, Science 2006; 312(5777):1165-8). The delivery of this promise in radiation oncology is dependent on the ability to define the variables that define response to clinical radiotherapy. Although most strategies in personalized medicine have focused on specific disease sites and/or drug therapies (van 't Veer et al., Nature 2002; 415(6871):530-6; Beer et al., Nat Med 2002; 8(8):816-24; Chung et al., Cancer Cell 2004; 5(5):489-500; Eschrich et al., J Clin Oncol 2005; 23(15): 3526-35; Giles et al., Semin Oncol 2008; 35 (1 Suppl 1):S1-17), the impact of individualizing radiation therapy is significant. Approximately 60% of cancer patients are treated with radiation therapy during their diagnosis (Perez, Principles and Management of Radiation Therapy. Philadelphia-New York: Lippincott-Raven; 1998). Thus, radiation therapy provides a common denominator in cancer therapeutics.

Significant advances towards personalized radiation therapy have been largely achieved by physical advances in radiotherapy treatment planning and delivery (Bucci et al., CA Cancer J Clin 2005; 55(2):117-34). In contrast, the efforts in understanding the biological parameters that define intrinsic radiosensitivity have not met the same success. Thus, radiotherapy is prescribed without considering the potential individual differences in tumor and patient radiosensitivity. However there is evidence to suggest that differences in intrinsic radiosensitivity exist (Zelefsky et al., J. Urology 2001; 166(3):876-81) and understanding their biological basis could significantly impact clinical practice. Thus, a successful radiosensitivity predictive assay would be central to the development of biologically-guided personalized treatment strategies in radiation oncology. However, although a number of promising approaches have been developed in the past (e.g., determination of ex-vivo tumor SF2, (Bjork-Eriksson et al., Int J Radiat Oncol Biol Phys 2000; 46(1):13-9; Buffa et al., Int J Radiat Oncol Biol Phys 2001; 50(5):1113-22; Eschwege et al., Int J Radiat Oncol Biol Phys 1997; 39(4):849-53; Taghian et al., Int J Radiat Oncol Biol Phys 1993; 25(2):243-9; West et al., British Journal of Cancer 1997; 76(9):1184-90; West et al., Br J Cancer 1993; 68(4): 819-23); the use of electrodes to measure tumor hypoxia (Fyles et al., J Clin Oncol 2002; 20(3):680-7; Movsas et al., Urology 2002; 60(4):634-9); and determination of tumor proliferative potential (Tpot) (Begg et al., Radiother Oncol 1999; 50(1):13-23; Bourhis et al., Int J Radiat Oncol Biol Phys 1996; 35(3):471-6; Corvo et al., J Clin Oncol 1995; 13(8): 1843-50), none has become routine in the clinic.

SUMMARY

At least in part, the inventions described herein are based on the development of methods and models that predict intrinsic sensitivity of a tumor to radiation therapy based on a gene expression profile.

In one aspect, the invention provides methods, e.g., computer-implemented methods, for predicting the sensitivity of a cell, i.e., a living cell, e.g., a tumor cell or a normal (non-tumor) cell, or a cultured cell, to a selected dose of radiation therapy. The methods include assigning a radiation sensitivity index to the cell based on expression levels of two or more signature genes in the cell, wherein the radiation sensitivity index indicates whether the cell is sensitive to radiation therapy.

In an additional aspect, the invention provides methods for predicting the effect of radiation therapy on a tumor. The methods include assigning a radiation sensitivity index to the tumor based on expression levels of two or more signature genes in a cell from the tumor, wherein the radiation sensitivity index indicates whether the radiation therapy is likely to be effective.

In yet another aspect, the invention provides methods for assessing a tumor in a subject for a radiation therapy regimen. The methods include assigning a radiation sensitivity index to the tumor based on expression levels of two or more signature genes in a cell from the tumor, wherein the radiation sensitivity index indicates whether the tumor in the subject should be treated with radiation therapy.

In a further aspect, the invention provides methods for selecting a treatment regimen for a subject having a tumor. The methods include assigning a radiation sensitivity index to the tumor based on expression levels of two or more signature genes in a cell from the tumor, and selecting a treatment regimen for the subject based on the radiation sensitivity index. In general, a radiation sensitivity index below a threshold indicates that radiation therapy is likely to be effective in treating the tumor, and the method includes selecting a treatment regimen including radiation therapy. Conversely, a radiation sensitivity index above a threshold indicates that radiation therapy is not likely to be effective in treating the tumor, and the method includes selecting a treatment regimen excluding radiation therapy, or a treatment regime including a high dose of radiation therapy.

In another aspect, the invention provides methods for selecting a dose of radiation to be administered to a subject having a tumor. The methods include assigning to the tumor a radiation sensitivity index for a preselected dose of radiation based on expression levels of two or more signature genes in a cell from the tumor, and selecting a dose of radiation for the subject based on the radiation sensitivity index at the preselected dose of radiation. In some embodiments, the methods include selecting a dose of radiation that is the same as or less than the preselected dose of radiation, if the radiation sensitivity index is below a threshold. In some embodiments, the methods include selecting a dose of radiation that is the greater than the preselected dose of radiation, if the radiation sensitivity index is above a threshold.

In some embodiments of the methods described herein, assigning a radiation sensitivity index comprises applying a linear regression model to the gene expression levels, e.g., a rank-based linear regression model. In some embodiments, the expression levels of the two or more signature genes are weighted.

In some embodiments, the linear regression model is represented by the following algorithm:

$$RSI = k_1 \cdot AR + k_2 \cdot c\text{-jun} + k_3 \cdot STAT1 + k_4 \cdot PKC + k_5 \cdot RelA + k_6 \cdot cAbl + k_7 \cdot SUMO1 + k_8 \cdot PAK2 + k_9 \cdot HDAC + k_{10} \cdot IRF1. \qquad \text{I}$$

In some embodiments of the methods described herein, assigning a radiation sensitivity index can include determining a level of expression of two or more signature genes in a cell.

In some embodiments of the methods described herein, the signature genes are selected from the group consisting of Androgen receptor (AR); Jun oncogene (c-Jun); Signal transducer and activator of transcription 1 (STAT1); Protein kinase C, beta (PRKCB or PKC); V-rel reticuloendotheliosis viral oncogene homolog A (avian) (RELA or p65); c-Abl oncogene 1, receptor tyrosine kinase (ABL1 or c-Abl); SMT3 suppressor of mif two 3 homolog 1 (*S. cerevisiae*) (SUMO1); PAK2; Histone deacetylase 1 (HDAC1); and Interferon regulatory factor 1 (IRF1). In some embodiments, the signature genes comprise a subset of the genes as listed in Table 10, 11, or 12. Optionally, assigning a radiation sensitivity index can also include using gene expression levels of one or more genes listed in FIGS. 6A-6P.

In another aspect, the invention provides computer-implemented method of identifying genes associated with radiation sensitivity. The methods include assigning a radiation sensitivity value to one or more populations of cells, wherein the radiation sensitivity value represents the sensitivity of the cells to a selected dose of radiation; determining a level of gene expression in the one or more populations of cells for each of a plurality of genes; and identifying a subset comprising two or more genes, the expression of which is correlated with the radiation sensitivity value. In some embodiments, the subset of the genes is identified by a method including applying a model representing gene expression and radiosensitivity, e.g., a multivariate linear regression model. The model can include, e.g., at least one coefficient representing one, two, or all three of: tissue of origin, ras status, or p53 status. In addition, the model can include information regarding the dose of radiation administered and the presence of any additional treatment or factors relevant to the cell.

In some embodiments, the methods further include associating a classifier representing biological importance with each gene in the subset of genes, expression of which is correlated with the radiation sensitivity value, and selecting a second subset comprising two or more genes wherein the classifier representing biological importance is above a preselected threshold, thereby selecting a subset of biologically important genes. In some embodiments, the classifier representing biological importance is based on a review of relevant scientific literature. In some embodiments, the model also includes a variable representing an effect of administration of a treatment on expression of each gene in the subset of biologically important genes.

In some embodiments, the methods further include selecting a third subset comprising one or more genes based on the effect of administration of the treatment, thereby identifying a subset of therapeutic target genes, e.g., genes the expression of which may be usefully manipulated to alter (i.e., increase or decrease) sensitivity to radiation. In some embodiments, the effect of the treatment is an increase or decrease in radiosensitivity. In some embodiments, the methods further include selecting a treatment that has an effect on radiosensitivity in the model.

In yet another aspect, the invention provides databases including a plurality of records, wherein each record includes data on the expression of at least two signature genes in a cell, and a value representing sensitivity of the cell to a selected dose of radiation. In some embodiments, the database also includes data regarding the administration of a treatment, e.g., chemotherapy, to the cell. In some embodiments, the database is in computer readable form.

Also provided herein are microarrays including a substrate and a plurality of individually addressable hybridisable array elements arranged thereon, wherein the individually addressable hybridisable array elements are selective for at least two signature genes, and optionally at least one hybridisable array element selective for an internal normalization control gene. In some embodiments, the plurality of hybridisable array elements consists of at least one element selective for each of AR; c-Jun; STAT1; PKC; RelA (p65); c-Abl; SUMO-1; PAK2; HDAC1; and IRF1.

In an additional aspect, the invention provides microfluidic devices including a substrate and a plurality of reaction chambers with reagents for selective quantification of at least two signature genes; and optionally at least one reaction chamber comprising reagents for selective quantification of an internal normalization control gene. In some embodiments, the devices include duplicate sets of the reaction chambers, e.g., to allow processing of multiple samples simultaneously.

In a further aspect, the invention provides a medium, e.g., computer-readable medium, bearing instructions to cause a computer to perform a method described herein. For example, the medium can bear instructions to cause a computer to assign a radiation sensitivity index to a cell based on expression levels of two or more signature genes in the cell. In some embodiments, assigning a radiation sensitivity index comprises applying a linear regression model to the gene expression levels, e.g., a rank-based linear regression model, e.g., wherein the two or more signature genes are weighted.

In an additional aspect, the invention provides a medium, e.g., computer-readable medium, bearing instructions to cause a computer to assign a radiation sensitivity value to one or more populations of cells, wherein the radiation sensitivity value represents the sensitivity of the cells to a selected dose of radiation; assign a level of gene expression in the one or more populations of cells for each of a plurality of genes; and identify a subset comprising two or more genes, the expression of which is correlated with the radiation sensitivity value. In some embodiments, identifying a subset of the genes comprises applying a model representing gene expression and radiosensitivity, e.g., a multivariate linear regression model. In some embodiments, the model includes at least one coefficient representing one, two, or all three of: tissue of origin, ras status, or p53 status.

In some embodiments, the medium further comprises instructions to cause a computer to associate a classifier representing biological importance with each gene in the subset of genes, expression of which is correlated with the radiation sensitivity value, and selecting a second subset comprising two or more genes wherein the classifier representing biological importance is above a preselected threshold, thereby selecting a subset of biologically important genes.

In some embodiments, the model further comprises a variable representing an effect of administration of a treatment on expression of each gene in the subset of biologically important genes. In some embodiments, the medium further includes instructions to cause a computer to select a third subset comprising two or more genes based on the effect of administration of the treatment, thereby identifying a subset of therapeutic target genes.

Also provided by the present invention are kits including reagents for the specific quantification of gene expression levels of two or more signature genes in a cell, and instructions for carrying out a method as described herein. In some embodiments, the kits include a medium as described herein.

The present invention has a number of advantages. The models and methods described herein provide an opportunity to individualize radiation dose parameters based on intrinsic radiosensitivity. Since higher doses of radiation therapy are associated with higher toxicity rate (Peeters et al., Int J Radiat Oncol Biol Phys 2005; 61(4):1019-34), dose personalization would result in a therapeutic ratio benefit. In addition the model may provide a unique framework to understand the differences between responders and non-responders that share a predicted radioresistant phenotype. This may allow the accurate identification of patients that benefit from the addition of concurrent chemotherapy.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 4A-4H is a list setting forth gene combinations (profiles) that were evaluated and demonstrated significant association with radiosensitivity in the Rectal+Esophagus cohorts described herein. The gene symbols are joined by '_' and the p-values from tests of significance between responders and non-responders are also given.

FIGS. 6A-6P is a list setting forth 500 genes identified as being correlated with radiosensitivity using a systems network model as described herein.

FIG. 7 is a list of exemplary control genes useful in the methods described herein.

DETAILED DESCRIPTION

Figure 1A:
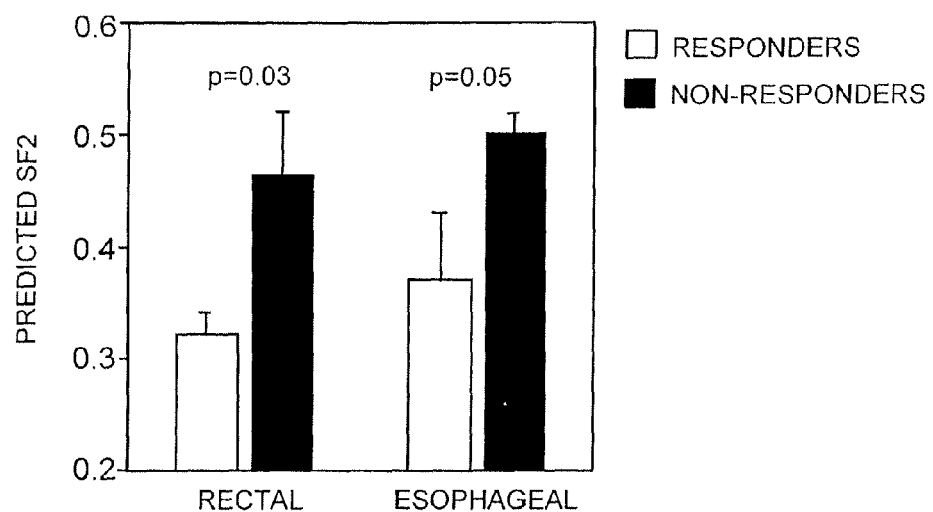
FIGS. 1A and B are bar graphs showing that the predicted tumor radiosensitivity is correlated with clinical response to concurrent radiochemotherapy in rectal and esophageal cancer patients. Predicted radiosensitivity indices (RSI) for each patient were generated using a ten-gene, rank-based linear regression model built from the cell line data as described herein. Statistical significance was determined using a one-sided Mann-Whitney test for differences. (1A) The mean predicted RSI of responders is significantly lower than in non-responders in both clinical cohorts (esophageal: p=0.05, rectal: p=0.03). (1B) Predicted RSI of each individual patient in both cohorts is significantly different relative to response (combined: p=0.001511).

The advent of high dimensional and high-throughput technologies has provided an opportunity to address the development of biomarkers from a different perspective. For example, gene expression signatures have been shown to be prognostic in breast (van 't Veer et al., Nature 2002; 415 (6871):530-6), lung (Beer et al., Nat Med 2002; 8(8):816-24), head and neck (Chung et al., Cancer Cell 2004; 5(5):489-500) and colon cancer (Eschrich et al., J Clin Oncol 2005; 23(15): 3526-35). Recent studies have identified biomarkers predictive of patient response to drug treatment, including response to Gleevec in Chronic Myelogenous Leukemia (CML) (Giles et al., Semin Oncol 2008; 35 (1 Suppl 1):S1-17). In addition, gene expression can predict cellular intrinsic radiosensitivity (Torres-Roca et al., Cancer Res. 65(16):7169-76 (2005)). The present inventors have developed a gene expression model to predict radiosensitivity in patients.

Described herein is a novel multi-gene expression model of intrinsic tumor radiosensitivity in a database of 48 human cancer cell lines. The model is based on the expression of sets of signature genes, which predicts a radiosensitivity index (RSI) that is directly proportional to tumor radioresistance. The model was clinically validated as a predictive factor of pathological response in two independent cohorts of esophageal (n=12) and rectal (n=14) cancer patients treated with preoperative concurrent chemoradiation in prospective clinical trials at Moffitt Cancer Center. In addition, RSI calculated by a method described herein was of prognostic value in a third external dataset of head and neck cancer patients (n=92) treated with definitive concurrent chemoradiation within Phase 2 and 3 clinical trials at the Netherlands Cancer Institute. Thus this model can be used to individualize therapy in clinical radiation oncology. For example, the model provides an opportunity to individualize radiation dose parameters based on intrinsic radiosensitivity. Since higher doses of radiation therapy are associated with higher toxicity rate, dose personalization would result in a therapeutic ratio benefit. In addition the model provides a unique framework to understand the differences between responders and non-responders that share a predicted radioresistant phenotype. This allows more accurate identification of patients that benefit from the addition of concurrent chemotherapy.

In the molecular medicine era, high-throughput technologies (e.g., microarrays and proteomics) have led to the identification of numerous molecular signatures of prognostic and/or predictive significance (van 't Veer et al., Nature 2002; 415(6871):530-6; Beer et al., Nat Med 2002; 8(8):816-24; Chung et al., Cancer Cell 2004; 5(5):489-500; Eschrich et al., J Clin Oncol 2005; 23(15):3526-35; Alizadeh et al., Nature 2000; 403(6769):503-11; Bild et al., Nature 2006; 439(7074): 353-7; van de Vijver et al., New Eng. J. Med. 2002; 347(25): 1999-2009; Shedden et al., Nat Med 2008; 14(8):822-7). However the initial enthusiasm that these signatures would lead to personalized medicine has been dampened by their frequent lack of robustness (Simon et al., J Natl Cancer Inst 2003; 95(1):14-8).

The robustness of the radiosensitivity model described herein is supported by several lines of evidence. First, the algorithm was validated in three independent prospectively collected datasets in three different diseases. Second, the model was valid across different gene expression platforms. Gene expression data in the esophageal and rectal cancer cohorts were derived from Affymetrix U-133 Plus microarrays. However, gene expression in the head and neck dataset was derived from NKI arrays, which is a two channel based cDNA microarray platform. The observation that the algorithm is transferable across platforms is important as it demonstrates transferability to other clinical platforms (e.g., using RT-PCR/Formalin-fixed tissue). Third, all patients in the validating clinical cohorts were treated with concurrent chemoradiation, since we were unable to obtain a dataset of patients treated with radiation alone. However the algorithm was based on cellular radiosensitivity. Thus, in spite of this potential source of inaccuracy, the model was still validated. Finally, the model showed both predictive and prognostic value.

The model described herein is designed to predict tumor radiosensitivity. RSI was prognostic in the head and neck cancer dataset, suggesting that the biological factors that determine radiosensitivity are related to disease prognosis after treatment. This is consistent with the observation that complete pathological response in both esophageal and rectal cancer has strong prognostic significance in several studies (Janjan et al., Am J Clin Oncol 2001; 24(2):107-12; Chirieac et al., Cancer 2005; 103(7):1347-55; Gavioli et al., Dis Colon Rectum 2005; 48(10):1851-7; Capirci et al., Int J Radiat Oncol Biol Phys. 2008 Sep. 1; 72(1):99-107. Epub Apr. 11, 2008). Thus a model that can identify complete responders would indeed be desirable. Using the current model, 6/8 complete responders fall below the threshold suggested by the ROC analysis (SF2=0.46) suggesting that this model successfully identifies this population.

In addition, there is a role for identifying patients that are likely to be downstaged, particularly in rectal cancer. For example, this knowledge might lead to better counseling of patients with low-lying rectal tumors where sphincter-sparing surgery is being considered. Patients that have low lying rectal cancer are generally patients that have a tumor within 5 cm of the anal sphincter. Classically, these patients when operated were treated with an abdomino-perineal resection (APR), which removes the anal sphincter and thus requires the patient to have a permanent colostomy bag, which generally adversely affects the patient's quality of life. In order to address this, protocols were developed about 10-15 years ago to test whether using a course of preoperative radiation or chemoradiation would improve the ability of the surgeon to spare the sphincter; shrinking the tumor improves the chances that the surgeon can remove the cancer and reconnect the rectum and keep the normal sphincter mechanism intact. This approach has been successful, but the likelihood of sphincter-sparing surgery is related to the amount of downstaging achieved by chemoradiation. Thus, the model described herein can improve patient counseling before a treatment decision is made. For example, if the patient is likely to respond to preoperative treatment because the model determines that the rectal tumor is radiosensitive, then the chances of success are high. However, if the tumor is radioresistant, success is unlikely, and the patient can be counseled to go directly to surgery and thereby be spared the side effects of a treatment that is unlikely to be successful, or if preoperative treatment is still pursued then higher doses of radiation therapy could be prescribed to increase the chances of success.

Determination of Radiosensitivity Index (RSI) of a Tumor

The methods described herein use a rank-based linear algorithm to assign a radiosensitivity index (RSI) to a cell, i.e., a living cell, e.g., a tumor cell from a patient, a normal cell from a patient, or a cultured cell. In general, the methods are applicable to any mammal, particularly humans. The methods include determining expression levels of signature genes in a cell or cells of the tumor, and determining a RSI based on the expression levels. In some embodiments, the methods include the use of two or more, e.g., three, four, five, six, seven, eight, nine, or all ten signature genes, as follows: Androgen receptor (AR); Jun oncogene (c-Jun); Signal transducer and activator of transcription 1 (STAT1); Protein kinase C, beta (PRKCB or PKC); V-rel reticuloendotheliosis viral oncogene homolog A (avian) (RELA or p65); c-Abl oncogene 1, receptor tyrosine kinase (ABL1 or c-Abl); SMT3 suppressor of mif two 3 homolog 1 (*S. cerevisiae*) (SUMO1); PAK2; Histone deacetylase 1 (HDAC1); and Interferon regulatory factor 1 (IRF1).

TABLE A

Exemplary Sequences of Signature Genes - Human

| Gene Name | Gene Symbol | Refseq Identifiers | Probe Design Identifier |
|---|---|---|---|
| Androgen Receptor | AR | NM_000044.2<br>NM_001011645.1 | M23263.1 |
| Jun oncogene | | NM_002228.3 | J04111.1 |
| Signal transducer and activator of transcription 1 | STAT1 | NM_007315.2<br>NM_139266.1 | M97935.1 |
| Protein kinase C, beta | PRKCB<br>PKC | NM_002738.5<br>NM_212535.1 | X06318.1 |
| v-rel reticulo-endotheliosis viral oncogene homolog A (avian) | RELA<br>P65 | NM_021975.2 | U33838.1 |
| c-Abl oncogene 1, receptor tyrosine kinase | ABL1<br>c-Abl | NM_007313.2<br>NM_005157.3 | X16416.1 |
| SMT3 suppressor of mif two 3 homolog 1 (*S. cerevisiae*) | SUMO1 | NM_001005781.1<br>NM_001005782.1<br>NM_003352.4 | U83117.1 |
| P21 protein (Cdc42/Rac)- activated kinase 2 | PAK2 | NM_002577.3 | U24153.1 |
| Histone deacetylase 1 | HDAC1<br>HDAC | NM_004964.2 | D50405.1 |
| Interferon regulatory factor 1 | IRF1 | NM_002198.2 | L05072.1 |

Although the exemplary gene sequences set forth above are for the human genes, and thus are best suited for use in human cells, one of skill in the art could readily identify mammalian homologs using database searches (for known sequences) or routine molecular biological techniques (to identify additional sequences). In general, genes are considered homologs if they show at least 80%, e.g., 90%, 95%, or more, identity in conserved regions (e.g., biologically important regions).

In some embodiments, the profile includes the signature genes listed in a profile shown in Table 10, Table 11, Table 12, or FIGS. 4A-4G. In some embodiments, the profile includes at least c-jun, STAT1, cAbl, and IRF1. In some embodiments, the profile includes at least IRF1.

A linear regression model useful in the methods described herein includes gene expression levels and coefficients, or weights, for combining expression levels. The coefficients can be calculated using a least-squares fit of the proposed model to a measure of cellular radiation sensitivity. One example described herein used the survival fraction at 2 Gy (SF2) although other measures at other dose levels (e.g., SF8) can be considered with different coefficients being determined from each. The functional form of the algorithm is given below, wherein each of the $k_i$ coefficients will be determined by fitting expression levels to a particular RSI measure.

$$RSI = k_1*AR + k_2*c\text{-jun} + k_3*STAT1 + k_4*PKC + k_5*RelA + k_6*cAbl + k_7*SUMO1 + k_8*PAK2 + k_9*HDAC + k_{10}*IRF1 \qquad I$$

In some embodiments, the methods include applying an algorithm to expression level data determined in a cell; e.g., a rank-based linear regression algorithm as described herein. In some embodiments, the algorithm includes weighting coefficients for each of the genes.

Methods of Use

The methods described herein can be used to identify a radiation sensitivity index to a selected dose of radiation for any solid tumor in a subject. A solid tumor is an abnormal mass of hyperproliferative or neoplastic cells from a tissue other than blood, bone marrow, or the lymphatic system, which may be benign or cancerous. In general, the tumors treated by the methods described herein are cancerous. As used herein, the terms "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of solid cancerous growths, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair. Examples of solid tumors are sarcomas, carcinomas, and lymphomas. Leukemias (cancers of the blood) generally do not form solid tumors.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the disease is lung carcinoma, rectal carcinoma, colon carcinoma, esophageal carcinoma, prostate carcinoma, head and neck carcinoma, or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

In some embodiments, the tumors treated by a method described herein are of epithelial cell origin. In some embodiments, the tumors originate from lung, colon, rectal, esophageal, prostate, or head/neck tissues (e.g., originating from the upper aerodigestive tract, including the lip, oral cavity, nasal cavity, paranasal sinuses, pharynx, and larynx, e.g., squamous cell carcinomas originating from the mucosal lining (epithelium)). In some embodiments, the tumors are metastatic, and originate from an epithelial tissue (and are thus epithelial in origin) but have spread to another tissue, e.g., epithelial-origin prostate cancer that has spread to the bones of the pelvis, spine and/or ribs, or lung carcinoma that has metastasized to the adrenal glands, liver, brain, or bones.

The methods described herein can identify tumors that are sensitive to radiation therapy, and thereby identify subjects who would benefit from administration of radiation therapy having, or who would benefit from concurrent administration of radiation therapy and radiation sensitizing chemotherapy. For example, once a RSI has been determined for a tumor, if the RSI is low and thus indicates that the tumor is sensitive to radiation (and thus is likely to be effectively treated with radiation), then a course of radiation alone can be prescribed for the patient, or radiation and possibly less invasive surgical removal methods, e.g., laparoscopic methods. Alternatively, if the RSI is high and thus indicates that the tumor is less sensitive or is not sensitive to radiation therapy, then a course of chemotherapy, e.g., radiation sensitizing chemotherapy, can be prescribed in combination with radiation therapy, and optionally more invasive or radical surgical resection. Thus the methods can be used to predict a subject's response to radiation therapy. In some embodiments, the threshold for sensitivity using an RSI as defined in esophageal and rectal cancer as 0.46.

As one example, the methods can be used for identifying patients that are likely to be downstaged, particularly in rectal cancer. For example, this knowledge might lead to better counseling of patients with low-lying rectal tumors where sphincter-sparing surgery is being considered, as described above.

In some embodiments, a subject having a tumor is identified (methods for diagnosing the presence of a tumor are well known in the art and need not be repeated herein). A test sample is obtained from the tumor and the level of signature protein or nucleic acid (e.g., mRNA) is evaluated, wherein the level of signature protein or nucleic acid is indicative of the sensitivity of the tumor to radiation therapy. As used herein, a "test sample" refers to a biological sample obtained from a subject of interest including a cell or cells, e.g., tissue, from the tumor.

The assays described herein can also be used to determine whether a subject should be administered one or more of radiation therapy, chemotherapy, or surgical resection to treat a solid tumor, e.g., to select a therapy or therapeutic regime for a subject. For example, such methods can be used to determine whether a subject can be effectively treated with radiation therapy alone or radiation therapy with a second, non-radiation treatment modality, e.g., surgery or chemotherapy, or will need radiation, surgery, and chemotherapy.

In addition, the methods described herein can be used on normal cells, i.e., non-tumor cells, to determine their sensitivity to radiation therapy. This allows the use of the model to predict the likelihood of radiation therapy-related toxicity or other side effects.

The network system models described herein can also be used to select genes to target for agents, e.g., radiosensitizing or radioprotective agents. In these methods, the network models are modified to model the effects of modulating various genes. One such approach is to simulate the effects of biological targeting of one or more of the identified network hubs. This type of in silico perturbation of the developed model can provide additional information on the hubs most likely to effect radiation phenotype. The model can be perturbed by systematically reducing (using computer simulations) the rank or weight of each hub gene to the lowest possible value, in effect "knocking" the gene out. The altered expression pattern will be used to predict patient radiosensitivity using the same model previously constructed.

Differences from the unaltered SF2 predictions will be recorded. These changes in SF2 will be examined and averaged over the entire patient cohort to estimate the impact of individual gene knockout.

Radiation therapies, chemotherapies, surgical resection techniques, and methods that can be used to select specific therapies appropriate for a given tumor, are known in the art, see, e.g., "Practical Radiotherapy Planning," Dobbs, Barrett, and Ash (1999) Arnold; "Walter & Miller's Textbook of Radiotherapy," Bomford and Kunkler (2002) Churchill Livingstone; "Cancer Chemotherapy and Biotherapy: Principles and Practice," Chabner and Longo (2005) Lippincott Williams & Wilkins; "Regional Chemotherapy: Theory and Practice," Kerr and McArdle (2000) Informa Healthcare; and "Textbook of Surgery," Tjandra et al. (2006) Wiley-Blackwell.

Assays for Determining Expression Levels

Any method known in the art for obtaining a sample comprising at least one living cell (preferably a plurality of cells), e.g., a cell from a tumor (e.g., from a biopsy), or a normal cell, or a cultured cell, can be used. Commonly used methods to obtain tumor cells include surgical (the use of tissue taken from the tumor after removal of all or part of the tumor) and needle biopsies. The samples should be treated in any way that preserves intact the gene expression levels of the living cells as much as possible, e.g., flash freezing or chemical fixation, e.g., formalin fixation.

Any method known in the art can be used to extract material, e.g., protein or nucleic acid (e.g., mRNA) from the sample. For example, mechanical or enzymatic cell disruption can be used, followed by a solid phase method (e.g., using a column) or phenol-chloroform extraction, e.g., guanidinium thiocyanate-phenol-chloroform extraction of the RNA. A number of kits are commercially available for use in isolation of mRNA. Purification can also be used if desired. See, e.g., Peirson and Butler, Methods Mol. Biol. 2007; 362: 315-27. A number of methods are also known in the art to obtain proteins from cells, see, e.g., "Protein Methods," 2nd Edition by Bollag et al., Wiley Pub. (1996). Optionally, cDNA can be transcribed from the mRNA.

Gene expression levels can be determined in many different ways, including the quantification of fluorescence of hybridized mRNA on glass slides, Northern blot analysis, real-time reverse transcription PCR(RT-PCR) or other measures of gene expression abundance. Each of these ways provides a different scale, however each approach is proportional to the abundance of a particular mRNA transcript.

A number of assays suitable for the determination of expression levels of the signature genes in a biological sample are known in the art. For example, expression levels can be evaluated by obtaining a biological sample from tumor of a test subject and contacting the biological sample with a compound or an agent capable of detecting mRNA for the signature genes, or protein encoded by the signature genes, such that the level of the protein or nucleic acid is detected in the biological sample. The term "biological sample" includes tissues, cells and fluids comprising cells or tissues isolated from tumor of a subject, as well as tissues and cells and fluids present within a subject. A preferred biological sample is a biopsy sample taken from the tumor. The level of expression of the signature genes can be measured in a number of ways, including, but not limited to: measuring the mRNA encoded by the signature genes; measuring the amount of protein encoded by the signature genes; or measuring the activity of the protein encoded by the signature genes.

The level of mRNA corresponding to the signature gene in a cell can be determined both by in situ and by in vitro formats.

The isolated mRNA can be used in hybridization or amplification assays that include, but are not limited to, Southern or Northern analyses, polymerase chain reaction analyses and probe arrays. One exemplary diagnostic method for the detection of mRNA levels involves contacting the isolated mRNA with a nucleic acid molecule (probe) that can hybridize to the mRNA encoded by the gene being detected. The nucleic acid probe can be, for example, a full-length nucleic acid or an oligonucleotide of at least 7, 15, 30, 50, 100, 250 or 500 nucleotides in length and sufficient to specifically hybridize under stringent conditions to mRNA for a signature gene. Other suitable probes for use in the diagnostic assays are known in the art.

In one format, mRNA (or cDNA) from the sample is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) from the sample is contacted with the probes, for example, in a two-dimensional gene chip array. A skilled artisan can adapt known mRNA detection methods for use in detecting the level of mRNA encoded by the signature genes.

The level of mRNA in a sample that is encoded by one of signature can be evaluated with nucleic acid amplification, e.g., by rtPCR (Mullis (1987) U.S. Pat. No. 4,683,202), ligase chain reaction (Barany (1991) Proc. Natl. Acad. Sci. USA 88:189-193), self sustained sequence replication (Guatelli et al., (1990) Proc. Natl. Acad. Sci. USA 87:1874-1878), transcriptional amplification system (Kwoh et al., (1989), Proc. Natl. Acad. Sci. USA 86:1173-1177), Q-Beta Replicase (Lizardi et al., (1988) Bio/Technology 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

A preferred method is the use of microfluidic devices, e.g., for high-throughput real time-polymerase chain reaction (RT-PCR), e.g., as described herein.

For in situ methods, a cell or tissue sample can be prepared/processed and immobilized on a support, typically a glass slide, and then contacted with a probe that can hybridize to mRNA that encodes the signature gene being analyzed.

In another embodiment, the methods further contacting a control sample with a compound or agent capable of detecting signature mRNA, and comparing the presence of signature mRNA in the control sample with the presence of signature mRNA in the test sample.

A variety of methods can be used to determine the levels of proteins encoded by the selected signature genes. In general, these methods include contacting an agent that selectively binds to the protein, such as an antibody, with a sample, and evaluating the level of protein in the sample. In a preferred embodiment, the antibody bears a detectable label. Antibodies can be polyclonal, or more preferably, monoclonal. An intact antibody, or a fragment thereof (e.g., Fab or F(ab')2) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are known in the art, as are methods of quantifying levels of proteins detected thereby.

The detection methods can be used to detect signature protein in a biological sample in vitro as well as in vivo. In vitro techniques for detection of signature protein include enzyme linked immunosorbent assays (ELISAs), immunoprecipitations, immunofluorescence, enzyme immunoassay (EIA), radioimmunoassay (RIA), and Western blot analysis. In vivo techniques for detection of signature protein include introducing into a subject a labeled anti-signature antibody. For example, the antibody can be labeled with a radioactive marker whose presence and location in a subject can be detected by standard imaging techniques.

In another embodiment, the methods further include contacting a control sample with a compound or agent capable of detecting signature protein, quantifying the level of signature protein, and comparing the level of signature protein in the control sample with the level of signature protein in the test sample.

In some embodiments, the sensitivity of a tumor to radiation therapy can be predicted by determining a gene expression profile including expression levels for two or more of the signature genes described herein, and comparing that expression profile to a reference profile, e.g., a reference profile representing a tumor that is sensitive to radiation; in that case, substantial similarity between the reference profile and the profile of expression from the tumor would indicate that the tumor was sensitive to radiation. Methods for performing such methods are known in the art, e.g., as described in U.S. Pat. No. 7,148,008.

Kits

The invention also includes kits for detecting and quantifying the selected signature genes (e.g., mRNA or protein corresponding to the signature genes) in a biological sample. For example, the kit can include a compound or agent capable of detecting mRNA or protein corresponding to the signature genes in a biological sample; and a standard; and optionally one or more reagents necessary for performing detection, quantification, or amplification. The compounds, agents, and/or reagents can be packaged in a suitable container. The kit can further comprise instructions for using the kit to detect and quantify signature protein or nucleic acid.

For antibody-based kits, the kit can include: (1) a first antibody (e.g., attached to a solid support) which binds to a polypeptide corresponding to a signature gene; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence corresponding to a signature gene or (2) a pair of primers useful for amplifying a nucleic acid molecule corresponding to a signature gene. The kit can also includes a buffering agent, a preservative, and/or a protein stabilizing agent. The kit can also include components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

In some embodiments, the kits include reagents specific for the quantification of the signature genes listed in a profile shown in Table 10, Table 11, Table 12, or FIGS. 4A-4G. In some embodiments, the kits include primers or antibodies selective for at least c-jun, STAT1, cAbl, and IRF1. In some embodiments, the kits include primers or antibodies selective for at least IRF1 and one additional signature gene. microfluidic devices for RT-PCR. In some embodiments, the kits also include primers or antibodies selective for a housekeeping or control gene, e.g., as listed in FIG. 7.

Microarrays/Microfluidic Devices

Also described herein are microarrays useful for detecting and quantifying levels of mRNA or protein corresponding to the signature genes. The microarray comprises a substrate and hybridisable array elements. For the detection of mRNA, the microarray will include a plurality of individually addressable areas including hybridizable array elements selective for the selected signature genes. For the detection of protein, the microarray will include a plurality of individually addressable areas including reagents for the detection of one or more proteins encoded by the signature genes, e.g., antibodies.

In some embodiments, the microarrays include hybridisable array elements selective for the signature genes listed in a profile shown in Table 10, Table 11, Table 12, or FIGS. 4A-4G. In some embodiments, the microarrays include hybridisable array elements selective for at least c-jun, STAT1, cAbl, and IRF1. In some embodiments, the microarrays include hybridisable array elements selective for at least IRF1 and one additional signature gene.

The term "microarray" refers to a substrate having an ordered arrangement of hybridisable array elements arranged thereon. In some embodiments, the array elements are arranged so that there are preferably at least about 10 different array elements, on a 1 cm.sup.2 substrate surface. The maximum number of array elements is unlimited, but can be upwards of at least 100,000 array elements. Furthermore, a hybridization signal from each of the array elements is individually distinguishable. In a preferred embodiment, the array elements comprise polynucleotide probes.

Hybridization causes a denatured polynucleotide probe and a denatured complementary target to form a stable duplex through base pairing. Hybridization methods are well known to those skilled in the art (See, e.g., Laboratory Techniques in Biochemistry and Molecular Biology, Vol. 24: Hybridization With Nucleic Acid Probes, P. Tijssen, ed. Elsevier Science, New York, N.Y. (1993)). Conditions can be selected for hybridization where exactly complementary target and polynucleotide probe can hybridize, i.e., each base pair must interact with its complementary base pair. Alternatively, conditions can be selected where target and polynucleotide probes have mismatches but are still able to hybridize. Suitable conditions can be selected, for example, by varying the concentrations of salt or formamide in the prehybridization, hybridization and wash solutions, or by varying the hybridization and wash temperatures.

Hybridization can be performed at low stringency with buffers, such as 6×SSPE with 0.005% Triton X-100 at 37° C., which permits hybridization between target and polynucleotide probes that contain some mismatches to form target polynucleotide/probe complexes. Subsequent washes are performed at higher stringency with buffers, such as 0.5× SSPE with 0.005% Triton X-100 at 50° C., to retain hybridization of only those target/probe complexes that contain exactly complementary sequences. Alternatively, hybridization can be performed with buffers, such as 5×SSC/0.2% SDS at 60° C. and washes are performed in 2×SSC/0.2% SDS and then in 0.1×SSC. Stringency can also be increased by adding agents such as formamide. Background signals can be reduced by the use of detergent, such as sodium dodecyl sulfate, Sarcosyl or Triton X-100, or a blocking agent, such as sperm DNA.

Hybridization specificity can be evaluated by comparing the hybridization of specificity-control polynucleotide probes to specificity-control target polynucleotides that are added to a sample in a known amount. The specificity-control target polynucleotides may have one or more sequence mismatches compared with the corresponding polynucleotide probes. In this manner, whether only complementary target polynucleotides are hybridizing to the polynucleotide probes or whether mismatched hybrid duplexes are forming is determined.

After hybridization, the microarray is washed to remove non-hybridized nucleic acids and complex formation between the hybridisable array elements and the target polynucleotides is detected.

Methods for detecting complex formation are known in the art. In some embodiments, the target polynucleotides are labeled with a fluorescent label and measurement of levels and patterns of fluorescence indicative of complex formation is accomplished by fluorescence microscopy, preferably confocal fluorescence microscopy. An argon ion laser excites the fluorescent label, emissions are directed to a photomultiplier and the amount of emitted light detected and quantitated. The detected signal should be proportional to the amount of probe/target polynucleotide complex at each position of the microarray. The fluorescence microscope can be associated with a computer-driven scanner device to generate a quantitative two-dimensional image of hybridization intensity. The scanned image is examined to determine the abundance/expression level of each hybridized target polynucleotide.

Typically, microarray fluorescence intensities can be normalized to take into account variations in hybridization intensities when more than one microarray is used under similar test conditions. In a preferred embodiment, individual polynucleotide probe/target complex hybridization intensities are normalized using the intensities derived from internal normalization controls contained on each microarray, e.g., control genes, e.g., ubiquitin C; hydroxymethylbilane synthase; tyrosine 3-monooxygenase/tryptophan 5-monooxygenase activation protein, zeta polypeptide; polymerase (RNA) II (DNA directed) polypeptide A, 220 kDa; importin 8; hypoxanthine phosphoribosyltransferase 1 (Lesch-Nyhan syndrome); ribosomal protein, large P0 (RLP0); peptidylprolyl isomerase A (cyclophilin A); beta actin; beta glucuronidase; beta-2-microglobulin; phosphoglycerate kinase 1; glyceraldehyde-3-phosphate dehydrogenase; transferrin receptor (p90; CD71); TATA box binding protein; subunit A of the succinate dehydrogenase complex; and the 18s ribosomal RNA (see FIG. 7).

The microarrays described herein include (or consist of) individually addressable hybridisable array elements selective for the signature genes as described herein, or a subset thereof listed in any of Tables 10-12 or FIGS. 4A-4G. In some embodiments, the microarrays also include one or more hybridisable array elements selective for an internal normalization control, e.g., as described herein. In some embodiments, the microarrays do not include hybridisable array elements selective for other genes.

In some embodiments, a microfluidic RT-PCR/paraffin-preserved tissue platform can be used. There are several advantages to the use of this platform. First, this platform is practical to use for routine diagnostic application. For example, OncotypeDX, a multi-gene model for risk assessment in breast cancer is in an RT-PCR/paraffin-preserved tissue platform. Further, the RT-PCR approach is cost-efficient. In addition, a standardized and optimized test could readily be tested in banked tissue (paraffin-preserved), e.g., from cooperative group trials (e.g., the Radiation Therapy Oncology Group (RTOG)), for development into routine clinical use.

Custom-design microfluidics cards can be obtained, e.g., from Applied Biosystems (ABI), that include all 10 genes in the hub model, or a subset thereof (e.g., as described herein), along with the standard 16 housekeeping genes recommended by ABI, or a subset thereof. Additional genes, e.g., 20, 30, 40, 50, 60, 70, 80, 90, or 100 genes, e.g., genes selected from the larger network model consisting of 500 genes (listed in FIGS. 6A-6P), can also be included in the cards. In some embodiments, all genes will be present at least in duplicate, e.g., in duplicate or triplicate, enabling the analysis of two or more samples per card. As one example, if an ABI card is used, the microarray probeset targets identified using a method described herein will be sequence-aligned with the ABI probeset to determine the ABI probes closest to the microarray target.

As one example, the microfluidics assays can be performed substantially as follows. Briefly, THE ABI TAQMAN LOW DENSITY ARRAY (TLDA) cards profile gene expression using the Comparative CT Method of relative quantification. Each card consists of a series of 384 interconnected wells divided into eight sets of assays. Each well contains dried Applied Biosystems TaqMan primers and probes for one mRNA target. Each of the 8 ports of the card is loaded with 100 μL of sample-specific PCR mix (Each 100-μL PCR mix should contain 1 ng to 100 ng of total RNA converted to cDNA. Once the card is loaded with samples, it is centrifuged to distribute the PCR mix throughout the 48 wells of each port. The TLDA card is run in the AB 7900HT using relative quantification analysis.

General methods for making and using microfluidic devices are known in the art, see, e.g., U.S. Pat. Nos. 6,960, 437 and 7,250,260.

Databases

In another aspect, the invention features a database comprising a plurality of records. Each record includes data on the expression of at least two signature genes in a tumor cell, and at least one, two or preferably all of the following: data on tissue of origin of the cell; data on ras status of the cell; and data on p53 status of the cell, and optionally data on a preselected factor relating to a subject who has the tumor. In some embodiments, the preselected factor can be one or more of: the presence of a treatment (e.g., the administration of a compound, e.g., a drug (e.g., chemotherapy), vitamin, food or dietary supplement); the presence of an environmental factor (e.g., the presence of a substance in the environment); the presence of a genetic factor or physical factor such as age.

In some embodiments, the database includes at least two records, and the preselected factor in each of the records differs form the other record. For example, in one embodiment, the preselected factor can be administration of a compound and in one record the preselected factor includes administration of the compound and in the other record the compound is not administered, is administered at a different dose and/or a different compound is administered. In another embodiment, the preselected factor can be an environmental factor and in one record the factor is present and in the other record the environmental factor is not present or is present at a different level. In yet another embodiment, the preselected factor can be a physical factor such as age and the age in one record varies from the age in the other record, e.g., a difference in age of at least 5, 10, 15, 20 years or more.

In some embodiments, each record of the database includes data on at least two preselected factors relating to the subject. In one embodiment, the database includes at least two records, and at least one preselected factor in each of the records differs from the other record. Preferably, the database includes at least two records and at least one preselected factor in the records differ and at least one of the other preselected factors is the same. In other embodiments, the database can include at least two records and each record includes at least one preselected factor and at least one preselected condition.

In some embodiments, the database includes at least two records, wherein each record includes information regarding a cell including expression levels of a subset or all of the 10 signature genes as described herein, dose of radiation administered, and survival fraction in response to that dose of radiation (e.g., for a dose of 2 Gy, the survival fraction is referred to as SF2).

The database can be any kind of storage system capable of storing the various data for each of the records as described herein. For example, the database may be a flat file, a relational database, a table in a database, an object in a computer readable volatile or non-volatile memory, data accessible by computer program, such as data stored in a resource fork of an application program file on a computer readable storage medium. Preferably, the database is in a computer readable medium (e.g., a computer memory or storage device).

In some embodiments, each record can further include data on the expression of at least one internal control gene, e.g., as listed in FIG. 7.

The information obtained by evaluating the efficacy of radiation therapy in treating a tumor can also be used to evaluate the effects that various factors and conditions, e.g., environmental conditions, can have on tumor treatment. In some embodiments, the information can be stored in a database as described herein.

In another aspect, the invention features a method of evaluating the likelihood that radiation therapy will be effective in treating a tumor, using a database as described herein.

The database can be any kind of storage system capable of storing various data for each of the records as described herein. In preferred embodiments, the database is a computer medium having a plurality of digitally encoded data records. The data record can be structured as a table, e.g., a table that is part of a database such as a relational database (e.g., a SQL database of the Oracle or Sybase database environments).

As used herein, "machine-readable media" refers to any medium that can be read and accessed directly by a machine, e.g., a digital computer or analogue computer. Non-limiting examples of a computer include a desktop PC, laptop, mainframe, server (e.g., a web server, network server, or server farm), handheld digital assistant, pager, mobile telephone, and the like. The computer can be stand-alone or connected to a communications network, e.g., a local area network (such as a VPN or intranet), a wide area network (e.g., an Extranet or the Internet), or a telephone network (e.g., a wireless, DSL, or ISDN network). Machine-readable media include, but are not limited to: magnetic storage media, such as floppy discs, hard disc storage medium, and magnetic tape; optical storage media such as CD-ROM; electrical storage media such as RAM, ROM, EPROM, EEPROM, flash memory, and the like; and hybrids of these categories such as magnetic/optical storage media.

A variety of data storage structures are available to a skilled artisan for creating a machine-readable medium having recorded thereon the data described herein. The choice of the data storage structure will generally be based on the means chosen to access the stored information. In addition, a variety of data processor programs and formats can be used to store the information of the present invention on computer readable medium.

Computer Software/Hardware

Figure 5:
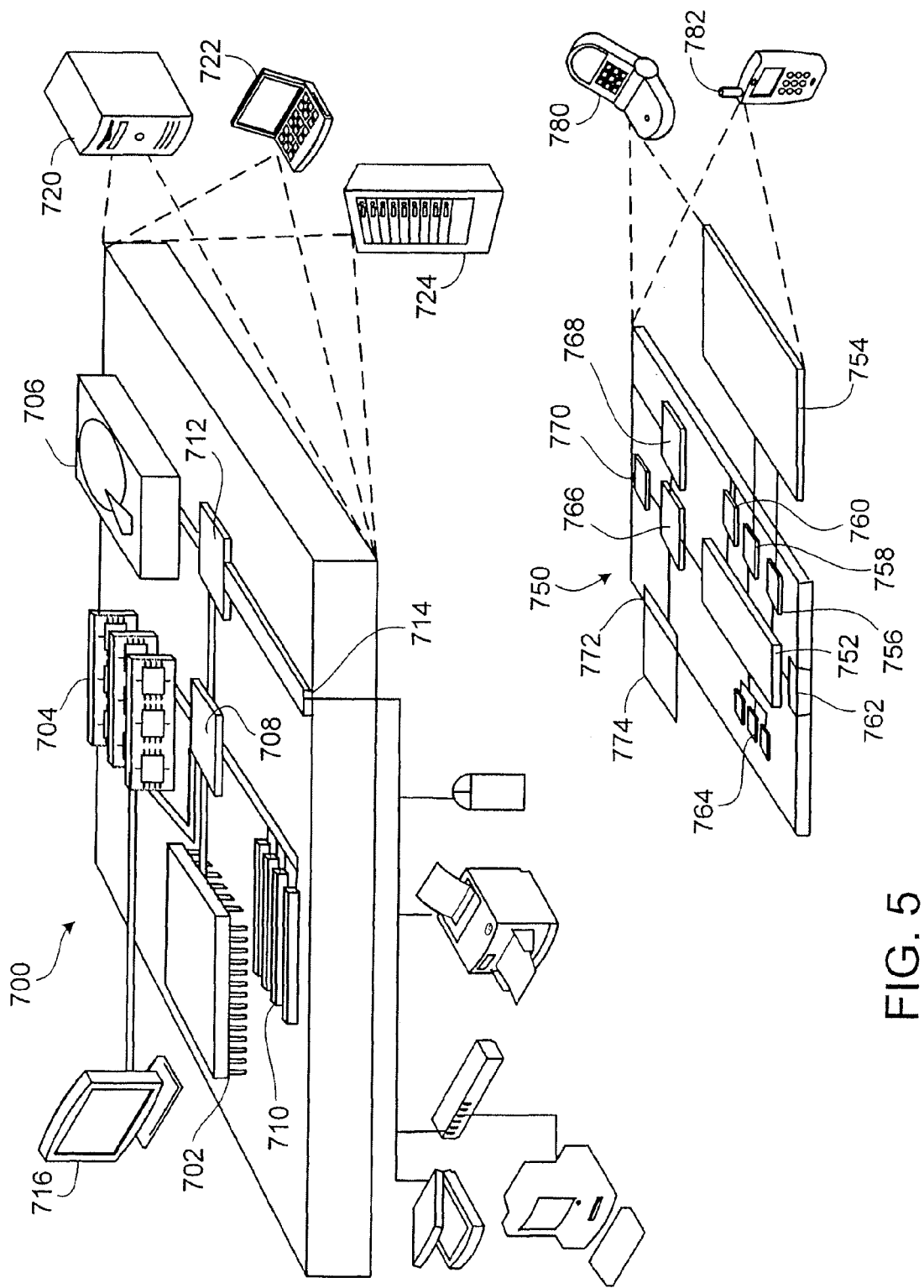
FIG. 5 is a block diagram of computing devices and systems.

FIG. 5 is a block diagram of computing devices and systems 700, 750 that may be used and implemented to perform operations associated with the audio file toolbox 404. Computing device 700 is intended to represent various forms of digital computers, such as laptops, desktops, workstations, personal digital assistants, servers, blade servers, mainframes, and other appropriate computers. Computing device 750 is intended to represent various forms of mobile devices, such as personal digital assistants, cellular telephones, smartphones, and other similar computing devices. The components shown here, their connections and relationships, and their functions, are meant to be exemplary only, and are not meant to limit implementations of the inventions described and/or claimed in this document.

Computing device 700 includes a processor 702, memory 704, a storage device 706, a high-speed interface 708 connecting to memory 704 and high-speed expansion ports 710, and a low speed interface 712 connecting to low speed bus 714 and storage device 706. Each of the components 702, 704, 706, 708, 710, and 712, are interconnected using various busses, and can be mounted on a common motherboard or in other manners as appropriate. The processor 702 can process instructions for execution within the computing device 700, including instructions stored in the memory 704 or on the storage device 706 to display graphical information for a GUI on an external input/output device, such as display 716 coupled to high speed interface 708. In other implementations, multiple processors and/or multiple buses can be used, as appropriate, along with multiple memories and types of memory. Also, multiple computing devices 700 can be connected, with each device providing portions of the operations (e.g., as a server bank, a group of blade servers, or a multi-processor system).

The memory 704 stores information within the computing device 700. In one implementation, the memory 704 is a computer-readable medium. In one implementation, the memory 704 is a volatile memory unit or units. In another implementation, the memory 704 is a non-volatile memory unit or units.

The storage device 706 is capable of providing mass storage for the computing device 700. In one implementation, the storage device 706 is a computer-readable medium. In various different implementations, the storage device 706 can be a floppy disk device, a hard disk device, an optical disk device, or a tape device, a flash memory or other similar solid state memory device, or an array of devices, including devices in a storage area network or other configurations. In one implementation, a computer program product is tangibly embodied in an information carrier. The computer program product contains instructions that, when executed, perform one or more methods, such as those described above. The information carrier is a computer- or machine-readable medium, such as the memory 704, the storage device 706, memory on processor 702, or a propagated signal.

The high speed controller 708 manages bandwidth-intensive operations for the computing device 700, while the low speed controller 712 manages lower bandwidth-intensive operations. Such allocation of duties is exemplary only. In one implementation, the high-speed controller 708 is coupled to memory 707, display 716 (e.g., through a graphics processor or accelerator), and to high-speed expansion ports 710, which can accept various expansion cards (not shown). In the implementation, low-speed controller 712 is coupled to storage device 706 and low-speed expansion port 714. The low-speed expansion port, which can include various communication ports (e.g., USB, Bluetooth, Ethernet, wireless Ethernet) can be coupled to one or more input/output devices, such as a keyboard, a pointing device, a scanner, or a networking device such as a switch or router, e.g., through a network adapter.

The computing device 700 can be implemented in a number of different forms, as shown in the figure. For example, it can be implemented as a standard server 720, or multiple times in a group of such servers. It can also be implemented as part of a rack server system 724. In addition, it can be implemented in a personal computer such as a laptop computer 722. Alternatively, components from computing device 700 can be combined with other components in a mobile device (not shown), such as device 750. Each of such devices can contain one or more of computing device 700, 750, and an entire system can be made up of multiple computing devices 700, 750 communicating with each other.

Computing device 750 includes a processor 752, memory 764, an input/output device such as a display 754, a communication interface 766, and a transceiver 768, among other components. The device 750 can also be provided with a storage device, such as a microdrive or other device, to provide additional storage. Each of the components 750, 752, 764, 754, 766, and 768, are interconnected using various buses, and several of the components can be mounted on a common motherboard or in other manners as appropriate.

The processor 752 can process instructions for execution within the computing device 750, including instructions stored in the memory 764. The processor can also include separate analog and digital processors. The processor can provide, for example, for coordination of the other components of the device 750, such as control of user interfaces, applications run by device 750, and wireless communication by device 750.

Processor 752 can communicate with a user through control interface 758 and display interface 756 coupled to a display 754. The display 754 can be, for example, a TFT LCD display or an OLED display, or other appropriate display technology. The display interface 756 can comprise appropriate circuitry for driving the display 754 to present graphical and other information to a user. The control interface 758 can receive commands from a user and convert them for submission to the processor 752. In addition, an external interface 762 can be provide in communication with processor 752, so as to enable near area communication of device 750 with other devices. External interface 762 can provide, for example, for wired communication (e.g., via a docking procedure) or for wireless communication (e.g., via Bluetooth or other such technologies).

The memory 764 stores information within the computing device 750. In one implementation, the memory 764 is a computer-readable medium. In one implementation, the memory 764 is a volatile memory unit or units. In another implementation, the memory 764 is a non-volatile memory unit or units. Expansion memory 774 can also be provided and connected to device 750 through expansion interface 772, which can include, for example, a SIMM card interface. Such expansion memory 774 can provide extra storage space for device 750, or can also store applications or other information for device 750. Specifically, expansion memory 774 can include instructions to carry out or supplement the processes described above, and can include secure information also. Thus, for example, expansion memory 774 can be provide as a security module for device 750, and can be programmed with instructions that permit secure use of device 750. In addition, secure applications can be provided via the SIMM cards, along with additional information, such as placing identifying information on the SIMM card in a non-hackable manner.

The memory can include for example, flash memory and/or MRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 764, expansion memory 774, memory on processor 752, or a propagated signal.

Device 750 can communicate wirelessly through communication interface 766, which can include digital signal processing circuitry where necessary. Communication interface 766 can provide for communications under various modes or protocols, such as GSM voice calls, SMS, EMS, or MMS messaging, CDMA, TDMA, PDC, WCDMA, CDMA2000, or GPRS, among others. Such communication can occur, for example, through radio-frequency transceiver 768. In addition, short-range communication can occur, such as using a Bluetooth, WiFi, or other such transceiver (not shown). In addition, GPS receiver module 770 can provide additional wireless data to device 750, which can be used as appropriate by applications running on device 750.

Device 750 can also communication audibly using audio codec 760, which can receive spoken information from a user and convert it to usable digital information. Audio codex 760 can likewise generate audible sound for a user, such as through a speaker, e.g., in a handset of device 750. Such sound can include sound from voice telephone calls, can include recorded sound (e.g., voice messages, music files, etc.) and can also include sound generated by applications operating on device 750.

The computing device 750 can be implemented in a number of different forms, as shown in the figure. For example, it can be implemented as a cellular telephone 780. It can also be implemented as part of a smartphone 782, personal digital assistant, or other similar mobile device.

Where appropriate, the systems and the functional operations described in this specification can be implemented in digital electronic circuitry, or in computer software, firmware, or hardware, including the structural means disclosed in this specification and structural equivalents thereof, or in combinations of them. The techniques can be implemented as one or more computer program products, i.e., one or more computer programs tangibly embodied in an information carrier, e.g., in a machine readable storage device or in a propagated signal, for execution by, or to control the operation of, data processing apparatus, e.g., a programmable processor, a computer, or multiple computers. A computer program (also known as a program, software, software application, or code) can be written in any form of programming language, including compiled or interpreted languages, and it can be deployed in any form, including as a stand alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub programs, or portions of code). A computer program can be deployed to be executed on one computer or on multiple computers at one site or distributed across multiple sites and interconnected by a communication network.

The processes and logic flows described in this specification can be performed by one or more programmable processors executing one or more computer programs to perform the described functions by operating on input data and generating output. The processes and logic flows can also be performed by, and apparatus can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, the processor will receive instructions and data from a read only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Information carriers suitable for embodying computer program instructions and data include all forms of non volatile memory, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, aspects of the described techniques can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The techniques can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation, or any combination of such back-end, middleware, or front-end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

One computer-implemented modeling algorithm is described herein (namely, the linear and quadratic analysis), although such algorithms themselves are generally outside the scope of the present invention. Other software-based modeling algorithms can also be utilized, alone or in combination, such as the classification or decision trees, support vector machines or neural networks.

EXAMPLES

The invention is further described in the following examples, which do not limit the scope of the invention described in the claims.

Example 1

A Radiosensitivity Systems Model Captures Central Regulatory Pathways in Radiation Response The model used in the methods described herein was developed in 48 cancer cell lines from the NCI panel of 60 (listed in Table 1). Radiosensitivity measurements (as determined by clonogenic survival at 2 Gy, SF2) were either determined using known methods (Gupta et al., Cancer Res 2001; 61:4278-82; Torres-Roca et al., Cancer Res 2005; 65(16): 7169-76) (25 cell lines) or obtained from the literature (23 cell lines). SF2 results for each cell line are presented in Table 1.

TABLE 1

48 cell lines and measured SF2 values.

| Cell Line | Recorded SF2 |
|---|---|
| BREAST_HS578T | 0.79 |
| BREAST_MDAMB231 | 0.82 |
| COLON_HCT116 | 0.38 |
| COLON_HCT15 | 0.4 |
| COLON_SW620 | 0.62 |
| LEUK_CCRFCEM | 0.185 |
| LEUK_HL60 | 0.315 |
| LEUK_MOLT4 | 0.05 |
| MELAN_SKMEL2 | 0.66 |
| NSCLC_A549ATCC | 0.61 |
| NSCLC_H460 | 0.84 |
| NSCLC_HOP62 | 0.164 |
| NSCLC_NCIH23 | 0.086 |
| OVAR_OVCAR5 | 0.408 |
| RENAL_SN12C | 0.62 |
| BREAST_BT549 | 0.632 |
| BREAST_MCF7 | 0.576 |
| BREAST_MDAMB435 | 0.1795 |
| BREAST_T47D | 0.52 |
| CNS_SF268 | 0.45 |
| CNS_SF539 | 0.82 |
| CNS_SNB19 | 0.43 |
| CNS_SNB75 | 0.55 |
| CNS_U251 | 0.57 |
| COLON_COLO205 | 0.69 |
| COLON_HCC-2998 | 0.44 |
| COLON_HT29 | 0.79 |
| COLON_KM12 | 0.42 |
| MELAN_LOXIMVI | 0.68 |

TABLE 1-continued 48 cell lines and measured SF2 values.

| Cell Line | Recorded SF2 |
|---|---|
| MELAN_M14 | 0.42 |
| MELAN_MALME3M | 0.8 |
| MELAN_SKMEL28 | 0.74 |
| MELAN_SKMEL5 | 0.72 |
| MELAN_UACC257 | 0.48 |
| MELAN_UACC62 | 0.52 |
| NSCLC_EKVX | 0.7 |
| NSCLC_HOP92 | 0.43 |
| OVAR_OVCAR3 | 0.55 |
| OVAR_OVCAR4 | 0.29 |
| OVAR_OVCAR8 | 0.6 |
| OVAR_SKOV3 | 0.9 |
| PROSTATE_DU145 | 0.52 |
| PROSTATE_PC3 | 0.484 |
| RENAL_7860 | 0.66 |
| RENAL_A498 | 0.61 |
| RENAL_ACHN | 0.72 |
| RENAL_CAKI1 | 0.37 |
| RENAL_UO31 | 0.62 |

Gene expression profiles for all cell lines at baseline were from Affymetrix HU6800 chips (7,129 genes) from a previously published study (Staunton et al., Proc Natl Acad Sci USA 2001; 98(19):10787-92). These are publicly available as supplemental data to the published study (Staunton et al., 2001). The gene expression data had been previously preprocessed using the Affymetrix MAS 4.0 algorithm in average difference units. Negative expression values were set to zero and the chips were normalized to the same mean intensity.

From the total of 7,129, a subset of genes of interest was selected by a linear regression algorithm where radiosensitivity was modeled based on survival fraction at 2 Gy (SF2) in the 48 cancer cell line database. Gene expression profiles and SF2 for all cell lines in the database had been previously determined, as described above.

A general linear model was created for each gene in the cell line dataset to model the SF2 values. Independent variables used within the linear model were gene expression, p53 mutation status (17 lines were wt, 31 were mutant), ras mutation status (33 wt, 15 mutant) and tissue of origin (TO), see Tables 2 and 3 for additional details on the numbers of cell lines within each category. Tissue of origin, p53 mutation and ras mutation were coded using "dummy" variables (0/1).

TABLE 2

Cell line characteristics for TO (Tissue of Origin)

| Tissue of Origin | Number of Cell lines |
|---|---|
| Melanoma | 8 |
| Colon | 7 |
| Breast | 6 |
| Renal | 6 |
| Non-Small Cell Carcinoma (NSCLC) | 6 |
| CNS | 5 |
| Ovarian | 5 |
| Leukemia | 3 |
| Prostate | 2 |
| TOTAL | 48 |

TABLE 3

Cell line characteristics by each biological variable.

| Tissue of Origin | ras wt | ras mut |
|---|---|---|
| p53 wt | | |
| Renal | 5 | 0 |
| Breast | 0 | 0 |
| CNS | 0 | 0 |
| Colon | 0 | 0 |
| Leukemia | 0 | 0 |
| Melanoma | 4 | 0 |
| NSCLC | 2 | 0 |
| Ovarian | 4 | 0 |
| Prostate | 2 | 0 |
| P53 mut | | |
| Renal | 0 | 1 |
| Breast | 4 | 2 |
| CNS | 5 | 0 |
| Colon | 4 | 3 |
| Leukemia | 0 | 3 |
| Melanoma | 3 | 1 |
| NSCLC | 0 | 4 |
| Ovarian | 0 | 1 |
| Prostate | 0 | 0 |

The linear model format initially considered all terms (9 TO, ras wt/mut, p53 wt/mut) and 2-, 3- and 4-way interactions among these terms. Without accounting for linearly dependent terms, there are 180 terms total, far more than the number of observations (i.e., 48). These include an intercept, 14 terms involving a single variable (gene expression, 9 TO, 2 p53, 2 ras), 53 paired terms, 76 triples and 36 terms with four variables interacting. However, the number of non-singular terms was far less due to the sample size (Table 3) and linearly dependent variables (typically interactions with no effect) are dropped from the model. Interactions of larger numbers of variables were dropped in favor of fewer in the case of linearly dependent variables. Thus there are only 29 terms in the linear model (an intercept, gene expression, 9 TO, p53, ras, 15 two-way interactions and 2 three-way interactions). When considering biological states, the intercept was not used thus producing 28 biological states. This model is expected to overfit the data significantly; however the model was used to describe the relationships in the data in an exploratory fashion as opposed to statistically determining a significant relationship.

TABLE 4

Terms used in linear modeling. The term (y) represents gene expression. The operator x represents an interaction term between two or more variables.

Terms y (Gene expression )
TissueTypeBREAST
TissueTypeCNS
TissueTypeCOLON
TissueTypeLEUK
TissueTypeMELAN
TissueTypeNSCLC
TissueTypeOVAR
TissueTypePROSTATE
RASmut
P53mut
y x TissueTypeBREAST
y x TissueTypeCNS
y x TissueTypeCOLON
y x TissueTypeLEUK
y x TissueTypeMELAN
y x TissueTypeNSCLC TABLE 4-continued Terms used in linear modeling. The term (y) represents gene expression. The operator x represents an interaction term between two or more variables.

Terms y x TissueTypeOVAR
y x TissueTypePROSTATE
y x RASmut
y x P53mut
TissueTypeBREAST x RASmut
TissueTypeCOLON x RASmut
TissueTypeMELAN x RASmut
TissueTypeNSCLC x RASmut
TissueTypeOVAR x RASmut
y x TissueTypeBREAST x RASmut
y x TissueTypeCOLON x RASmut A model based on the description above was constructed for each gene in the dataset using a least-squares fit. The best fitting genes were selected, as measured by the sum of squares of residuals. The gene-based linear models were compared to the fit expected simply from the biological characteristics (tissue of origin, ras status (mut vs. wild-type) and p53 status (mut vs. wild-type)). This simpler model used 28 terms and resulted in a sum of squared error of residuals of 1.208211.

The Resulting Model:

$$SF2 = k_0 + k_1(y_x) + k_2(TO) + k_3(\text{ras status}) + k_4(\text{p53 status}) + k_5(y_x)(TO) + k_6(y_x)(\text{ras status}) + k_7(TO)(\text{ras status}) + k_8(y_x)(\text{p53 status}) + k_9(TO)(\text{p53}) + k_{10}(\text{ras status})(\text{p53 status}) + k_{11}(y_x)(TO)(\text{ras status}) + k_{12}(y_x)(\text{ras status})(\text{p53 status}) + k_{13}(TO)(\text{ras status})(\text{p53 status}) + k_{14}(y_x)(TO)(\text{ras status})(\text{p53 status})$$

500 gene-based models were chosen (threshold ssq=0.5416959) corresponding to at most 45% of the sum squared error from the biological characteristics model. The 500 genes, which are listed in FIGS. 6A-6P, represent 7% of the total number of probesets on the chip.

Next, pathway analysis was performed to examine the biological significance of the genes identified. 500 probesets representing these genes were loaded into GeneGO Meta-Core software (GeneGO, Encinitas, Calif.) and analyzed for significant over-representation in various pathways; the primary edges (interconnections) were plotted using literature-based annotations and the model was reduced by identifying all genes (network hubs) with more than 5 edges and less than 50% of edges hidden within the network. 485 probesets were recognized in GeneGO.

Hubs within a gene network were defined using the GeneGO™ software as nodes consisting of more than 5 connections and less than 50% of the edges hidden within the network. Table 5 details all defined hubs within the radiation response network together with the number of edges and the number of hidden edges (along with the probesets used on each platform for each of the hubs).

TABLE 5

Radiation network hub genes.

| Gene Name | Gene Number | Number of Edges | Number of Hidden Edges | HU6800 Probeset | U133Plus Probeset |
|---|---|---|---|---|---|
| Androgen receptor | 1. | 19 | 0 | M23263_at | 211110_s_at |
| c-Jun | 2. | 19 | 4 | J04111_at | 201466_s_at |
| STAT1 | 3. | 15 | 1 | AFFX-HUMISGF3A/M97935_MA_at | AFFX-HUMISGF3A/M97935_MA_at |
| PKC | 4. | 14 | 4 | X06318_at | 207957_s_at |
| RelA (p65) | 5. | 14 | 2 | U33838_at | 201783_s_at |
| c-Abl | 6. | 13 | 0 | X16416_at | 202123_s_at |
| SUMO-1 | 7. | 13 | 0 | U83117_at | 208762_at |
| PAK2 | 8. | 11 | 3 | U24153_at | 205962_at |
| HDAC | 9. | 10 | 0 | D50405_at | 201209_at |
| Integrin | 10. | 7 | 4 | | |
| IRF1 | 11. | 7 | 0 | L05072_s_at | 202531_at |
| PKC-beta | 12. | 6 | 5 | | |
| Caspase-8 | 13. | 5 | 0 | | |
| CDC25C | 14. | 5 | 4 | | |
| Cyclin D1 | 15. | 5 | 0 | | |
| FasR (CD95) | 16. | 5 | 0 | | |
| Galpha(g)-specific peptide GPCRs | 17. | 5 | 5 | | |
| HES1 | 18. | 5 | 0 | | |

The Gather program (Gene Annotation Tool to Help Explain Relationships (Chang and Nevins, Bioinformatics 22(23):2926-2933, 2006) tool was used to identify significant relationships of terms from the 10 genes. A threshold of p<0.005 was used as a cutoff.

All hubs with more than 5 connections and less than 50% of edges hidden within the network were selected as the major hubs for classification purposes. Genes listed in Table 6 were selected. The probes used on each platform (Affymetrix HU6800, HG U133Plus 2.0 and NKI cDNA arrays) are also listed in Table 3. Matches were identified via sequence similarity to the original HU6800 platform.

Table 6 shows the ten "hub" genes on whose expression the radiosensitivity model is built. These genes are also referred to herein as "signature" genes.

TABLE 6

Radiation network hub (signature) genes.

| Gene Name | HU6800 Probeset | U133Plus Probeset | NKI Reporter |
|---|---|---|---|
| Androgen receptor | M23263_at | 211110_s_at | 324293 |
| c-Jun | J04111_at | 201466_s_at | 329987 |
| STAT1 | AFFX-HUMISGF3A/M97935_MA_at | AFFX-HUMISGF3A/M97935_MA_at | 308421 |
| PKC | X06318_at | 207957_s_at | 322907 |
| RelA (p65) | U33838_at | 201783_s_at | 326475 |
| c-Abl | X16416_at | 202123_s_at | 304192 |
| SUMO-1 | U83117_at | 208762_at | 308596 |
| PAK2 | U24153_at | 205962_at | 332859 |
| HDAC1 | D50405_at | 201209_at | 308690 |
| IRF1 | L05072_s_at | 202531_at | 310653 |

The selected genes are biologically important, as they have been reported to be involved in regulating radiation signaling (Deng et al., Nat Genet 2004; 36(8):906-12; Hallahan et al., International Journal of Radiation Oncology*Biology*Physics 1996; 36(2):355-60; Kao et al., J Biol Chem 1999; 274(49):34779-84; Li and Karin, PNAS 1998; 95(22):13012-7; Liu et al., Molecular Cell 2006; 21(4):467-80; Mårten Fryknäs et al., International Journal of Cancer 2007; 120(1):189-95; Nakajima et al., Radiat Res 2004; 161(5):528-34; Pamment et al., Oncogene 2002; 21(51):7776-85; Terzoudi et al., Int J Radiat Biol 2000; 76(5):607-15; Wang et al., Nucleic Acids Res 2005; 33(13):4023-34). In addition, 7/10 (HDAC1, PKC-beta, NFKB, c-Abl, STAT1, AR, PAK2) have been studied as targets for radiosensitizer development (Wang et al., Nucleic Acids Res 2005; 33(13):4023-34; Russell et al., Cancer Res 2003; 63(21):7377-83; Ma et al., J Clin Oncol 2003; 21(14):2760-76; Cerna et al., Current topics in developmental biology 2006; 73:173-204; Milas et al., Head & Neck 2003; 25(2):152-67, Kaminski et al., Int J Radiat Oncol Biol Phys 2003; 57(1):24-8). Furthermore, the Gene Ontology (GO) terms captured by the 10 gene systems model, include DNA damage response, histone deacetylation, regulation of cell cycle, apoptosis and proliferation, all of which play an important role in radiation response (Marples et al., Int J Radiat Oncol Biol Phys 2008; 70(5):1310-8; Chinnaiyan et al., Int J Radiat Oncol Biol Phys 2005; 62(1):223-9) Lindsay et al., Br J Radiol. 2007 September; 80 Spec No 1:S2-6; Ma et al., 2003, supra). One notable exception includes hypoxia (Moeller et al., Cancer Metastasis Rev 2007; 26(2):241-8). However, since the analysis is based on data generated in normoxic conditions, we would not expect the model to capture hypoxia-related genes. In summary, the systems model captures central pathways and genes involved in regulating radiosensitivity.

Eight different cell lines were used to validate the importance of c-jun in the systems model. In each experiment, a pooled siRNA and c-jun siRNA experiment were performed several times (i.e. replicates). One estimate of the impact, per cell line, of c-Jun knockdown is a Wilcoxon signed-rank test between the experiment and control that were run together. Table 7 represents the characteristics of the experiments performed, including the tissue of origin, number of times the experiment was performed, mean values (with standard deviation) and a p-value testing differences between mean values (Wilcoxon signed-rank test for cell line replicate experiments).

TABLE 7

Individual cell line siRNA experiments.

| Tissue of Origin | Cell Line | n | SF2 (Mean ± standard deviation) siRNA pool vs. c-Jun siRNA | p-value |
|---|---|---|---|---|
| Lung Cancer | A549 | 5 | 0.52 ± 0.13; 0.71 ± 0.11 | 0.062 |
| | H460 | 9 | 0.50 ± 0.06; 0.60 ± 0.08 | 0.004 |
| | Hop62 | 8 | 0.41 ± 0.16; 0.50 ± 0.18 | 0.039 |
| Colon Cancer | HCT116 | 7 | 0.23 ± 0.05; 0.30 ± 0.06 | 0.016 |
| | HCT15 | 7 | 0.59 ± 0.09; 0.66 ± 0.13 | 0.156 |
| | HT29 | 5 | 0.85 ± 0.21; 0.96 ± 0.31 | 0.312 |
| Breast Cancer | Hs578 | 10 | 0.62 ± 0.09; 0.61 ± 0.07 | 0.770 |
| | MDA231 | 6 | 0.61 ± 0.09; 0.67 ± 0.11 | 0.156 |

These results demonstrate that at least one of the genes in the model, c-jun, is mechanistically involved in the cellular response to radiation.

Example 2

Development of a Radiosensitivity Predictive Model Based on the Systems Model

A linear regression algorithm to predict radiosensitivity was developed and optimized using gene expression of the 10 genes in the systems model.

Translation of the model to other datasets was an important requirement, therefore the hubs were assigned ranks by expression (gene expression data for the 10 identified genes were rank ordered, so that lowest expression among the ten genes was ranked 1; HDAC gene expression was generally the highest of the ten genes and therefore was often ranked tenth) and the linear regression model was built from ranks (instead of absolute expression) (Xu et al., BMC Bioinformatics 2008; 9:125) based on expression levels in the 48 cell lines using the R statistical software package (available on the world wide web at r-project.org). The model predicts a continuous radiosensitivity index (RSI) that is based on the survival fraction at a given dose, measured for the cell lines in the database. Thus, the radiosensitivity index is directly proportional to radioresistance (high index=radioresistance). Since the 10 hubs were selected from the cell line data, cross-validation of this linear regression model would yield optimistically-biased estimates of accuracy. As a result, additional datasets were used for validation.

A general model based on expression of all 10 hub genes is as follows, including the weighting coefficient for each term representing expression levels of the recited gene:

$$RSI = k_1*AR + k_2*c\text{-jun} + k_3*STAT1 + k_4*PKC + k_5*RelA + k_6*cAbl + k_7*SUMO1 + k_8*PAK2 + k_9*HDAC + k_{10}*IRF1 \quad \text{I}$$

The rank-based linear regression equation for determining RSI at a dose of 2Gy identified using the present methods was the following:

$$RSI = -0.0098009*AR + 0.0128283*c\text{-jun} + 0.0254552*STAT1 - 0.0017589*PKC - 0.0038171*RelA + 0.1070213*cABL - 0.0002509*SUMO1 - 0.0092431*PAK2 - 0.0204469*HDAC - 0.0441683*IRF1 \quad \text{II}$$

Example 3

The Radiosensitivity Model Predicts Pathological Response to Chemoradiation in Rectal and Esophageal Cancer The regression model developed as described in Examples 1-2 was then applied to similarly rank-ordered patient data to generate a Radiation Sensitivity Index (RSI).

The model was applied to the prediction of clinical response to concurrent radiochemotherapy in two independent prospectively-collected pilot cohorts of patients with rectal (n=14) and esophageal cancer (n=12). Pathological response was defined by T stage criteria (see methods).

The Rectal Cancer Cohort consisted of 14 patients enrolled in an IRB-approved prospective Phase 1 trial evaluating escalating doses of oral topotecan as a radiosensitizing agent in patients with rectal cancer. Informed consent was obtained for all patients prior to enrollment. The eligibility criteria included patients with histologically-confirmed rectal cancer with a primary tumor at least 3 cm in size and a clinical stage of $T_2$-$T_4$. An ECOG performance status of 2 or less was required as well as a life expectancy of more than 3 months. The diagnosis could not be more than 90 days from initial clinic visit or from the start of therapy. All study subjects were treated at the H Lee Moffitt Cancer Center and Research Institute. Subjects were clinically-staged by endoscopic ultrasound (EUS). Tumor and adjacent normal mucosa biopsies (a minimun of 5 core biopsies) were obtained for microarray analysis before initiation of therapy and between day 10 and 14 of preoperative radiochemotherapy. For the purposes of this study only the pretreatment tumor tissue microarray was utilized. Biopsies were snap frozen in liquid nitrogen. No macro or microdissection of the biopsies was performed.

All study subjects were treated with preoperative concurrent radiochemotherapy and underwent surgical resection (APR or LAR in 13/14) within 8 weeks of completion of preoperative treatment. The starting dose of oral Topotecan was 0.25 mg/m² and it was administered at least 3 hours before XRT on a daily basis. Patients were treated with 45 Gy per day (prescribed to the isocenter) to a standard pelvic field with either a three field or four field 3-D conformal technique. Table 8 shows a summary of the clinical characteristics of this cohort.

TABLE 8

Clinical Characteristics for Rectal Cancer Trial

| Sex | |
| --- | --- |
| Male | 10 |
| Female | 4 |
| Age (y) | |
| Mean | 69.4 |
| Median (range) | 72 (50-90) |
| Chemotherapy Dose | |
| 0.25 mg/m²/day | 3 (21) |
| 0.4 mg/m2/day | 5 (36) |
| 0.55 mg/m2/day | 6 (43) |
| Ultrasound Tumor Stage | |
| T3 | 14 (100) |
| Pathological Tumor Stage | |
| T0 | 2 (14.3) |
| Tis | 1 (7) |
| T1 | 2 (14.3) |
| T2 | 3 (21.4) |
| T3 | 5 (36) |
| T4 | 1 (7) |
| Downstaging | |
| Yes | 8 (57) |
| No | 6 (43) |

Values are number (percentage) unless otherwise noted.

Pathological response in the rectal cancer cohort was defined by at least a decrease of one T stage in the primary tumor between the pretreatment EUS and the pathological evaluation of the specimen (Janjan et al., Int. J. Rad. Oncol. Biol. Phys. 1999; 44(5):1027-38; Janjan et al., Am J Clin Oncol 2001; 24(2):107-12). Pathological complete response was defined as no evidence of tumor in the surgical specimen (primary and nodes). Based on this definition, 57% (8/14) of the patients were considered responders.

The Esophageal Cancer Cohort consisted of 12 patients enrolled in an IRB-approved prospective tissue collection trial, aimed at defining molecular signatures of prognostic value in esophageal cancer. Clinical management was not dictated by the protocol and left to the clinical judgment of the treating physicians. Treatment details are presented in table 9. Eligibility criteria included a histological diagnosis of esophageal cancer, deemed a reasonable candidate for preoperative radiochemotherapy and/or esophagectomy by the evaluating physician. An ECOG performance below 2 was required. In addition, patients were required to be chemotherapy naïve. Study subjects were clinically staged by EUS. Biopsies of the tumor and normal mucosa were snap frozen in liquid nitrogen for microarray analysis.

All subjects in this cohort were treated with concurrent radiochemotherapy to be followed by planned esophagectomy. 9/12 underwent planned esophagectomy. Three patients completed concurrent radiochemotherapy but were not operated because of patient or physician preference (2 patients) or progressive disease (one patient). The clinical characteristics of this cohort is summarized in Table 9.

TABLE 9

Clinical Characteristics for Esophageal Trial

| Sex | |
| --- | --- |
| Male | 7 (58.3) |
| Female | 5 (41.7) |
| Age (y) | |
| Mean | 67.08 |
| Median (range) | 66 (51-80) |
| Chemotherapy Regimen | |
| CDDP + 5-FU | 3 (25) |
| 5-FU | 2 (16.7) |
| Carbo/Tax + 5-FU | 1 (8.3) |
| NA | 6 (50) |
| Radiation Dose | |
| 45 | 1 (8.3) |
| 50.4 | 4 (33.3) |
| 54 | 2 (16.7) |
| 61.2 | 1 (8.3) |
| NA | 4 (33.3) |
| Clinical Tumor Stage | |
| T2N1 | 1 (8.3) |
| T3N0 | 1 (8.3) |
| T3N1 | 7 (58.4) |
| T4N1 | 3 (25) |
| Pathological Tumor Stage | |
| T0N0 | 4 (33.3) |
| T0N1 | 1 (8.3) |
| T1aN0 | 1 (8.3) |
| T1N1 | 2 (16.7) |
| T2bN1 | 1 (8.3) |
| T2N1 | 1 (8.3) |
| Progressive Dx | 2 (16.7) |
| Downstaging | |
| Yes | 7 (58.3) |
| No | 5 (41.7) |

Values are number (percentage) unless otherwise noted.

Clinical response in the esophageal cancer cohort was defined as a decrease of at least two T stages between the pretreatment EUS evaluation and the pathological evaluation of the specimen (Chirieac et al., Cancer 2005; 103(7):1347-55). Three patients in our cohort did not undergo esophagectomy. One had progressive disease during preoperative therapy; the other two experienced clinical complete responses (documented by PET and/or EUS and biopsy) and had no evidence of disease at least one year after completion of treatment. Based on this definition 50% (6/12) of the patients were considered responders.

The specimen sampled was flash frozen within 15 minutes of resection and the RNA was extracted. Total RNA from the excised tissue was isolated using the TRIZOL™ Reagant (Invitrogen, Carlsbad, Calif.) and the manufacturer's protocol. The aqueous phase containing the RNA separated from the TRIZOL™ reagent was further purified using the RNeasy cleanup procedure (Qiagen Inc., Valencia, Calif.). The quality of total RNA was then assessed by agarose gel electrophoresis and $A_{260}/_{280}$ ratio or by analysis on the Agilent 2100 Bioanalyzer. Five micrograms of total RNA from each sample was processed for microarray analysis. The poly(A) RNA was specifically converted to cDNA and then amplified and labeled with biotin following the procedure initially described by Van Gelder et al. (Proc Natl Acad Sci USA 1990; 87(5):1663-7). Hybridization with the biotin labeled RNA, staining, and scanning of the chips followed the prescribed procedure outlined in the Affymetrix technical manual and has been previously described (Dobbin et al., Clin Cancer Res 2005; 11 (2 Pt 1):565-72).

The oligonucleotide probe arrays used were the Affymetrix U133A 2.0 plus chips. Since the original cell line data was created on the HU6800 GeneChip, while the newer patient expression data was generated on HG-U133Plus chips, it was necessary to translate the hub probesets in Table 6. This was done using the blast program to find the best U133+ probeset match to the consensus sequence from which the 6800 probeset was designed. The Affymetrix NetAffx software was also used for this translation. Scanned output files were visually inspected for hybridization artifacts and then analyzed using the robust multi-array analysis method (RMA) (Irizarry et al., Nucleic Acids Res 2003; 31 (4):e15 (27)). Statistical testing for patient cohorts was determined from predicted RSI values using a one-sided Mann-Whitney test. The test was used to determine if the predicted RSI was significantly higher for non-responders. Bar-charts of patient response were graphed using mean and standard error values for each response group in both the rectal cancer and esophageal cancer data. Relapse-free survival differences between low and high RSI values were calculated using a log-rank test of censored survival times.

Figure 1B:
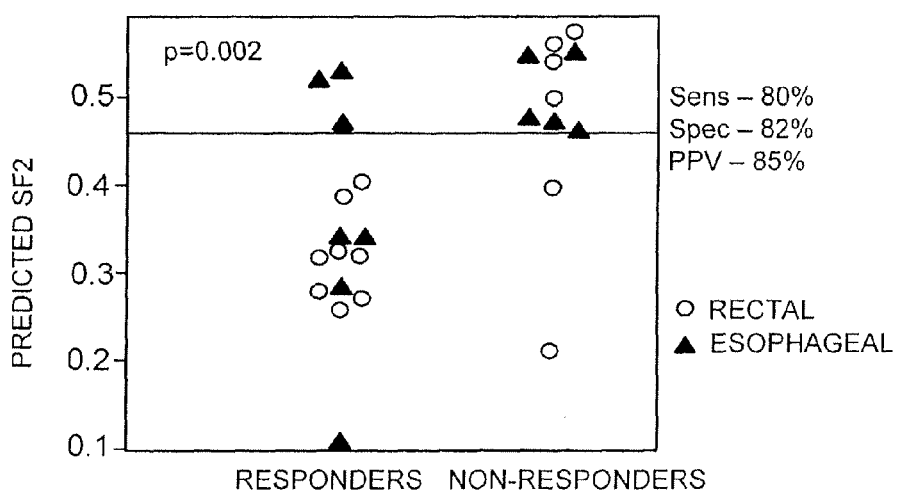

As shown in FIG. 1, the model significantly separated responders (R) from non-responders (NR) in the pilot clinical cohort (all patients, mean predicted radiosensitivity index, R vs. NR 0.34 vs. 0.48, p=0.002). Importantly, the model was accurate in both disease cohorts in spite of the small number of patients (rectal cancer patients, mean predicted radiosensitivity index, R vs. NR 0.32 vs. 0.46, p=0.03) (esophageal cancer patients, mean predicted radiosensitivity index, R vs. NR 0.37 vs. 0.50, p=0.05).

Figure 2:
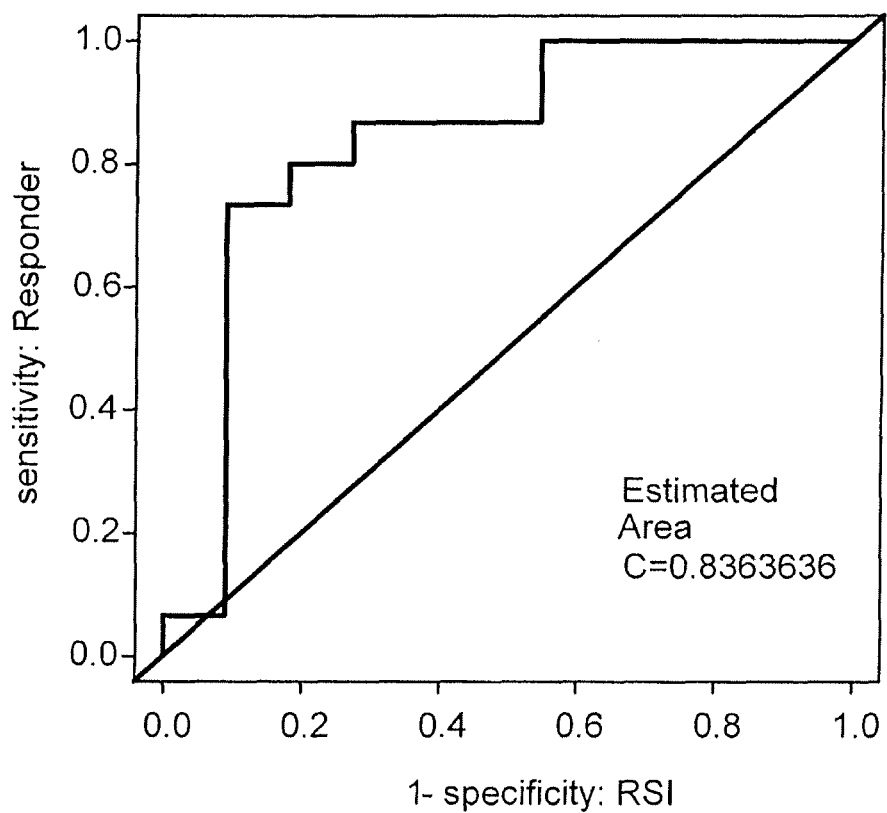
FIG. 2 is a ROC curve that was generated using the predicted RSI values to determine the sensitivity and specificity of the radiosensitivity predictor. Using a threshold RSI value of 0.4619592, the predictor has an 80% sensitivity and 82% specificity, with a positive predictive value (PPV) of 86%. The estimated area under the curve (AUC) is 0.84.

To further describe the model, an ROC curve (FIG. 2) was generated using the predicted radiosensitivity index values to determine the sensitivity and specificity of the predictor. Using a threshold RSI value of 0.46, the model has a sensitivity and specificity of 80 and 82% respectively, with a positive predictive value (PPV) of 86%. In addition, there were 8 patients that experienced a complete pathological response in the two cohorts. 6/8 complete responders had a predicted radiosensitivity index below the threshold. These numbers are encouraging since the predictor was not developed to account for the radiosensitizing effect of chemotherapy and the inclusion of chemotherapy was expected to account for prediction inaccuracies.

These results show that RSI when analyzed as a continuous variable is correlated with pathological response in rectal and esophageal cancer patients treated with preoperative concurrent chemoradiation.

It is important to note that false negatives (predicted radioresistant that responded) were the main inaccuracy when the model was dichotomized in the esophageal and rectal datasets. This population represented 60% of the misclassified cases in the esophageal and rectal cancer cohorts. It is possible that this inaccuracy is due to the radiosensitization effect of chemotherapy. The proportion of individuals within the rectal and esophageal dataset that are classified in this group (11.5%) is consistent with the observed improvement in clinical responses with concurrent chemotherapy over radiotherapy alone (Herskovic et al., The New England Journal of Medicine 1992; 326(24):1593-8; Al-Sarraf et al., J Clin Oncol 1997; 15(1):277-84 (published erratum appears in J Clin Oncol 1997 February; 15(2):866); Bosset et al., The New England journal of medicine 2006; 355(11):1114-23). Therefore, it is possible that this effect can be addressed by analyzing differences between responders and non-responders that share a predicted radioresistant phenotype.

Example 4

The Radiosensitivity Predictive Model is of Prognostic Value in Head and Neck Cancer The model was further tested as a prognostic marker in locally-advanced head and neck cancer patients treated with definitive concurrent radiochemotherapy.

The Head and Neck Cancer Cohort consisted of 92 patients with head and neck cancer treated within prospective randomized Phase II-III trials at The Netherlands Cancer Institute. The majority of tumors were locally-advanced advanced (94% T3 and above, 74% N1 and above). The full clinical details of this cohort were previously published (Pramana et al., Int J Radiat Oncol Biol Phys 2007; 69(5):1544-52). All patients were treated with concurrent radiochemotherapy with cisplatin-based chemotherapy. Total radiation dose was 70Gy in 2Gy daily fractions in all cases. Two different schedules of cisplatin were given: 1. (high dose) 100 mg/m$^2$ IV three times during radiotherapy or 150 mg/m$^2$ given intra-arterially four times during radiotherapy; or 2. (low dose) 20×6 mg/m$^2$ daily. No disease outcome differences were found between chemotherapy schedules.

Gene expression profiles for all patients were generated using the NKI array. These methods were previously published, see Pramana et al., Int J Radiat Oncol Biol Phys 2007; 69(5):1544-52. Probes were mapped from the HU6800 platform to the HG-U133 Plus 2.0 platform and NKI array format by mapping the probe sequences onto a corresponding NCBI refseq ID or genomic region, then identifying the closest probe match on the new microarray platform.

Figure 3:
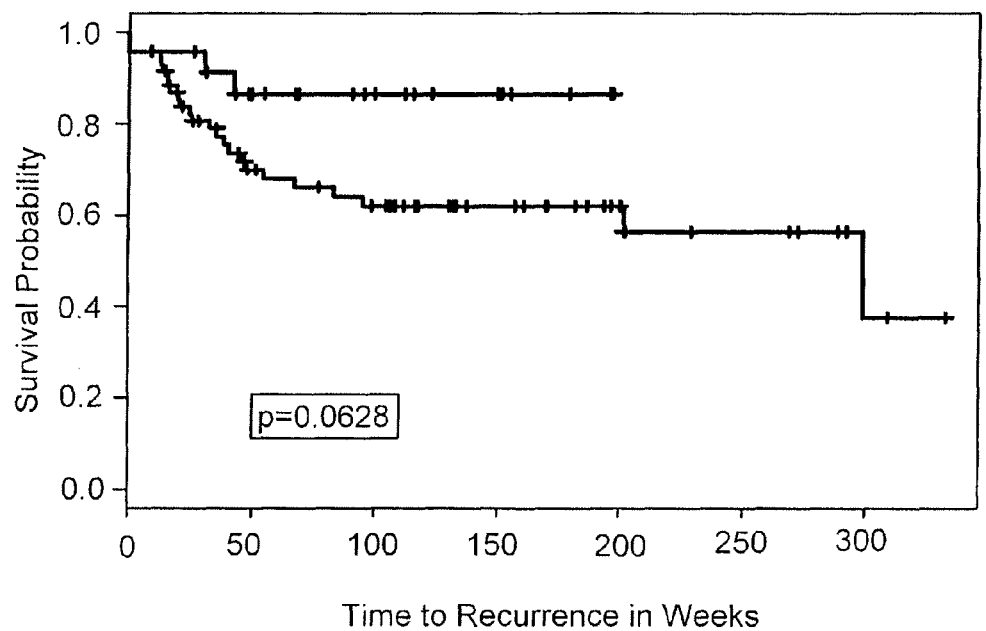
FIG. 3 is a line graph demonstrating that predicted radiosensitivity distinguishes clinical populations with different disease related outcomes in head and neck cancer. Radiosensitivity predictions were generated with the gene expression model as described in 92 patients treated with definitive concurrent radiochemotherapy at the Netherlands Cancer Institute. Using the 25th percentile as cutpoint (RSI<0.023), there is a superior 2 year Recurrence Free Survival (RFS) in the predicted radiosensitive group (86% vs. 62%, p=0.06).

Using the same algorithm developed in cell lines and tested in the rectal and esophageal cohorts, radiosensitivity predictions were generated for this dataset. The average radiosensitivity index prediction was lower in this disease site when compared with rectal and esophagus (predicted radiosensitivity index, head and neck vs. esophagus vs. rectal 0.06 vs. 0.43 vs. 0.39). Although this could be partly a function of radiosensitivity differences between these diseases, it could also be due to platform differences (Affymetrix U133 Plus vs. NKI array). In spite of these differences, the radiosensitivity index was still of prognostic value within the head and neck dataset. The predicted radiosensitive group had an improved 2 year Relapse-Free survival (2 yr RFS 86% vs. 62%, p=0.06), thus arguing that the model is capturing biological commonalities that determine tumor radiosensitivity across disease sites (FIG. 3).

These results show that RSI is of prognostic significance in a cohort of 92 patients with locally-advanced head and neck cancer. The applicability of the model in three different disease sites strongly suggests that the model captures commonalities that define radiosensitivity across disease sites. Therefore the model should be generally applicable to other disease sites (e.g., lung, prostate, or cervical cancer).

In addition, as noted above the gene expression in the head and neck dataset was derived from NKI arrays, which is a two channel based cDNA microarray platform, while the gene expression data in the esophageal and rectal cancer cohorts were derived from Affymetrix U-133 Plus microarrays. This indicates that the algorithm is transferable across platforms.

Example 5

Identification of Subsets of Genes Significantly Associated with Radiation Sensitivity To determine whether all 10 of the above-described signature genes were necessary for a robust prediction, subset analysis was performed using the methods described herein.

Considering the 10 signature genes, subsets of these genes were selected and tested for statistical significance in the patient cohorts described earlier. For each subset, the gene expression data was rank ordered and a linear regression model was built. The coefficients and ranks of these models differ from the 10-gene model. Each new model was evaluated by generating RSI predictions on the esophageal and rectal cancer patient cohort and using a one-sided Wilcox test for significant difference in RSI between responders and non-responders. In addition, a one-sided Student's t test was also used to assess statistical significance.

Likewise, the RSI predictions were generated for the head and neck cancer patient set. Here, the 25th percentile of predicted RSI was used as described above as a threshold for calling a patient's tumor radiosensitive or radioresistant (for the purposes of time to local recurrence). A log-rank statistical test was performed on recurrence free survival times between the predicted radiosensitive and radioresistant groups to assess statistical significance. In addition, the mean predicted RSI was also used a threshold and evaluated.

The rank-based approach to prediction does not allow single genes to be used. In addition, some subsets of two genes lead to identical ranking for all cell lines, thereby limiting the number of possible subsets to be evaluated.

All of the potential gene combinations were evaluated in each of the patient cohorts described above. Table 10 and 11 show results for statistical significant subsets of genes (gene symbols joined by '_') and p-values from tests of significance between responders and non-responders (in the manner described earlier). Many significant subsets were identified, ranging from subsets of 2 genes to 10 genes.

In the head & neck trial there were 12 significant subsets of genes when considering the difference in recurrence free survival split at the $25^{th}$ percentile of predicted RSI, which are listed in Table 10. Using the median of predicted RSI identified the gene subsets shown in Table 11.

TABLE 10

Subsets Significant in Head & Neck Cancer Cohort by $25^{th}$ Percentile

| Number in Subset | Combination | 25th Percentile |
|---|---|---|
| 4 | STAT1_SUMO1_HDAC_IRF1 | 0.053506572 |
| 5 | AR_STAT1_SUMO1_HDAC_IRF1 | 0.050918175 |
| 5 | c-jun_STAT1_RelA_SUMO1_IRF1 | 0.059557472 |
| 6 | AR_c-jun_STAT1_RelA_SUMO1_IRF1 | 0.042062687 |
| 6 | AR_c-jun_STAT1_cAbl_SUMO1_IRF1 | 0.046890608 |
| 6 | AR_c-jun_STAT1_SUMO1_HDAC_IRF1 | 0.053117262 |
| 6 | c-jun_STAT1_RelA_cAbl_SUMO1_IRF1 | 0.059557472 |
| 6 | c-jun_STAT1_RelA_SUMO1_PAK2_IRF1 | 0.059557472 |
| 7 | AR_c-jun_STAT1_RelA_SUMO1_PAK2_IRF1 | 0.042062687 |
| 7 | c-jun_STAT1_PKC_RelA_cAbl_HDAC_IRF1 | 0.046900514 |
| 8 | AR_c-jun_STAT1_PKC_RelA_cAbl_HDAC_IRF1 | 0.032529876 |
| 10 | AR_c-jun_STAT1_PKC_RelA_cAbl_SUMO1_PAK2_HDAC_IRF1 | 0.062801635 |

TABLE 11

Subsets Significant in Head & Neck Cancer Cohort by Median

| Number in Subset | Combination | Median |
|---|---|---|
| 5 | AR_PKC_cAbl_SUMO1_IRF1 | 0.039215827 |
| 5 | c-jun_STAT1_RelA_SUMO1_IRF1 | 0.059557472 |
| 6 | AR_c-jun_STAT1_RelA_SUMO1_IRF1 | 0.046890608 |
| 6 | AR_c-jun_STAT1_cAbl_SUMO1_IRF1 | 0.046890608 |
| 6 | c-jun_STAT1_RelA_cAbl_SUMO1_IRF1 | 0.059557472 |
| 6 | c-jun_STAT1_RelA_SUMO1_PAK2_IRF1 | 0.059557472 |
| 7 | AR_c-jun_STAT1_RelA_SUMO1_PAK2_IRF1 | 0.046890608 |
| 7 | AR_c-jun_STAT1_RelA_cAbl_SUMO1_IRF1 | 0.046890608 |
| 8 | AR_c-jun_STAT1_PKC_RelA_cAbl_SUMO1_IRF1 | 0.043331767 |

The Rectal & Esophageal trial had 259 significant subsets, ranging from two hubs to all ten; FIGS. 4A-4G present a list of those subsets.

There were five gene subsets that generated RSI predictions that were of statistical significance in both the head/neck and rectal and esophageal cancer patient cohorts. All included c-jun, STAT1, cAbl, IRF1, and are listed in Table 12:

TABLE 12

Subsets Significant in
Head & Neck, Esophageal, and Rectal Cancer Cohorts

| Number of Genes in Profile | Genes in Profile |
|---|---|
| 6 | AR + c-jun + STAT1 + cAbl + SUMO1 + IRF1 |
| 6 | c-jun + STAT1 + RelA + cAbl + SUMO1 + IRF1 |
| 7 | c-jun + STAT1 + PKC + RelA + cAbl + HDAC + IRF1 |
| 8 | AR + c-jun + STAT1 + PKC + RelA + cAbl + HDAC + IRF1 |
| 10 | AR + c-jun + STAT1 + PKC + RelA + cAbl + SUMO1 + PAK2 + HDAC + IRF1 |

This indicates that these subsets of genes can be used in the present methods in place of the ten signature gene profile.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a subject having a breast tumor, the method comprising:
    determining expression levels of signature genes comprising Androgen receptor (AR); Jun oncogene (c-Jun); Signal transducer and activator of transcription 1 (STAT1); Protein kinase C, beta (PRKCB or PKC); V-rel reticuloendotheliosis viral oncogene homolog A (avian) (RELA or p65); c-Abl oncogene 1, receptor tyrosine kinase (ABL1 or c-Abl); SMT3 suppressor of mif two 3 homolog 1 (*S. cerevisiae*) (SUMO1); p21 (CDKN1A)-activated kinase 2 (PAK2); Histone deacetylase 1 (HDAC1); and Interferon regulatory factor 1 (IRF1) in a cell from the tumor;
    assigning a radiation sensitivity index to the tumor based on expression levels of the signature genes;
    selecting a treatment regimen for the subject based on the radiation sensitivity index; and
    administering the selected treatment to the subject.

2. The method of claim 1, wherein a radiation sensitivity index below a threshold indicates that radiation therapy is likely to be effective in treating the tumor, and the method includes selecting a treatment regimen including radiation therapy; and
    wherein a radiation sensitivity index above a threshold indicates that radiation therapy is not likely to be effective in treating the tumor, and the method includes selecting a treatment regimen excluding radiation therapy, or a treatment regime including a high dose of radiation therapy.

3. The method of claim 1, comprising selecting a dose of radiation that is the greater than the preselected dose of radiation, if the radiation sensitivity index is above a threshold.

4. The method of claim 1, wherein assigning a radiation sensitivity index comprises applying a linear regression model to the gene expression levels.

5. The method of claim 4, wherein the model is a rank-based linear regression model.

6. The method of claim 1, wherein the two or more signature genes are weighted.

7. The method of claim 5, wherein the linear regression model is represented by the following algorithm:

$$RSI = k_1 \ast AR + k_2 \ast c\text{-jun} + k_3 \ast STAT1 + k_4 \ast PKC + k_5 \ast RelA + k_6 \ast cAbl + k_7 \ast SUMO1 + k_8 \ast PAK2 + k_9 \ast HDAC + k_{10} \ast IRF1. \qquad I$$

8. The method of claim 1, wherein the method is computer-implemented.

* * * * *

UNITED STATES PATENT AND TRADEMARK OFFICE
CERTIFICATE OF CORRECTION

PATENT NO. : 8,660,801 B2  
APPLICATION NO. : 13/037153  
DATED : February 25, 2014  
INVENTOR(S) : Javier F. Torres-Roca et al.

Page 1 of 1

It is certified that error appears in the above-identified patent and that said Letters Patent is hereby corrected as shown below:

In the Specification

Column 1, Line 17 through Line 24 should read:
FEDERALLY SPONSORED RESEARCH FOR DEVELOPMENT
This invention was made with government support under grant numbers CA108926 and CA101355 awarded by the National Institutes of Health and Grant No. DAMD 17-02-2-0051 awarded by the US Army Medical Research and Materiel Command (ARMY/MRMC). The Government has certain rights in the invention.

Signed and Sealed this
Twentieth Day of August, 2019

Andrei Iancu
*Director of the United States Patent and Trademark Office*